United States Patent
Jeong et al.

(10) Patent No.: US 9,556,275 B2
(45) Date of Patent: Jan. 31, 2017

(54) COMBINATION THERAPY USING ANTI-C-MET ANTIBODY AND ANTI-ANG-2 ANTIBODY

(71) Applicant: Samsung Electronics Co., Ltd., Suwon-si, Gyeonggi-do (KR)

(72) Inventors: Yun Ju Jeong, Hwaseong-si (KR); Kyung Ah Kim, Seongnam-si (KR); Kyung Eun Kim, Yongin-si (KR); Chungho Kim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 78 days.

(21) Appl. No.: 14/244,709

(22) Filed: Apr. 3, 2014

(65) Prior Publication Data
US 2014/0302039 A1 Oct. 9, 2014

(30) Foreign Application Priority Data

Apr. 3, 2013 (KR) ........................ 10-2013-0036506

(51) Int. Cl.
*A61K 39/00* (2006.01)
*C07K 16/28* (2006.01)
*C07K 16/22* (2006.01)

(52) U.S. Cl.
CPC .......... *C07K 16/2863* (2013.01); *C07K 16/22* (2013.01); *A61K 2039/507* (2013.01); *C07K 2317/24* (2013.01); *C07K 2317/622* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,942,602 A * | 8/1999 | Wels | A61K 47/48561 424/1.49 |
| 8,486,404 B2 | 7/2013 | Ryu et al. | |
| 8,546,544 B2 | 10/2013 | Cheong et al. | |
| 8,563,696 B2 | 10/2013 | Cheong et al. | |
| 8,617,554 B2 * | 12/2013 | Roberts | C07K 16/2893 424/130.1 |
| 9,101,610 B2 * | 8/2015 | Cheong | C07K 16/2863 |
| 2004/0052785 A1 | 3/2004 | Goodman et al. | |
| 2009/0123474 A1 | 5/2009 | Blakey et al. | |
| 2009/0226443 A1 | 9/2009 | Filvaroff et al. | |
| 2009/0274693 A1 | 11/2009 | Gilmer et al. | |
| 2009/0304694 A1 | 12/2009 | Oliner et al. | |
| 2011/0044998 A1 | 2/2011 | Bedian et al. | |
| 2011/0097262 A1 | 4/2011 | Goetsch et al. | |
| 2011/0104176 A1 | 5/2011 | Cheong et al. | |
| 2011/0129481 A1 | 6/2011 | Cheong et al. | |
| 2011/0150895 A1 | 6/2011 | Ryu et al. | |
| 2012/0065380 A1 | 3/2012 | Yoo et al. | |
| 2012/0100166 A1 | 4/2012 | Roschke et al. | |
| 2012/0148607 A1 * | 6/2012 | Hultberg | C07K 16/2863 424/174.1 |
| 2012/0189635 A1 | 7/2012 | Thurston et al. | |
| 2013/0089542 A1 * | 4/2013 | Lee | C07K 16/2863 424/133.1 |
| 2013/0089557 A1 * | 4/2013 | Cheong | C07K 16/2863 424/138.1 |
| 2013/0129722 A1 * | 5/2013 | Lowy | C07K 16/22 424/133.1 |
| 2014/0086926 A1 * | 3/2014 | Jeong | A61K 39/3955 424/139.1 |
| 2014/0105901 A1 * | 4/2014 | Lee | A61K 39/39558 424/139.1 |
| 2014/0105902 A1 * | 4/2014 | Lee | G01N 33/57492 424/139.1 |
| 2014/0212414 A1 * | 7/2014 | Oh | A61K 45/06 424/133.1 |
| 2014/0294830 A1 * | 10/2014 | Lee | A61K 39/3955 424/135.1 |
| 2014/0294837 A1 * | 10/2014 | Song | C07K 14/71 424/136.1 |
| 2014/0294838 A1 * | 10/2014 | Cho | C07K 16/2863 424/136.1 |
| 2014/0302029 A1 * | 10/2014 | Cho | C07K 16/2863 424/135.1 |
| 2014/0302030 A1 * | 10/2014 | Kim | A61K 39/39558 424/135.1 |
| 2014/0302517 A1 * | 10/2014 | Jung | C07K 16/4258 435/7.1 |

(Continued)

FOREIGN PATENT DOCUMENTS

| | | |
|---|---|---|
| EP | 2341067 A1 | 7/2011 |
| KR | 2010-0125033 A | 5/2009 |

(Continued)

OTHER PUBLICATIONS

US 8,481,689, 07/2013, Cheong et al. (withdrawn)
Rudikoff et al. (Proceedings of the National Academy of Sciences, 1982, 79:1979-1983).*
MacCallum et al. (Journal of Molecular Biology, 1996, 262:732-745).*
De Pascalis et al. (Journal of Immunology, 2002, 169:3076-3084).*
Casset et al. (Biochemical and Biophysical Research Communications, 2003, 307:198-205).*
Vajdos et al. (Journal of Molecular Biology, 2002, 320:415-428).*
Holm et al. (Molecular Immunology, 2007:1075-1084).*
Chen et al. (Journal of Molecular Biology, 1999, 293:865-881).*

(Continued)

*Primary Examiner* — Julie Wu
(74) *Attorney, Agent, or Firm* — Leydig, Voit & Mayer, Ltd.

(57) ABSTRACT

A method for inhibiting angiogenesis and treating angiogenesis related diseases comprising administering an anti-c-Met antibody or an antigen-binding fragment thereof, and an anti-Ang-2 antibody or an antigen-binding fragment thereof, in combination simultaneously or sequentially; as well as related compositions and methods.

6 Claims, 3 Drawing Sheets

(56) References Cited

U.S. PATENT DOCUMENTS

2014/0303357 A1* 10/2014 Lim ................ A61K 39/39591
530/387.7
2014/0308284 A1* 10/2014 Kim ..................... C07K 16/30
424/135.1

FOREIGN PATENT DOCUMENTS

| KR | 2011-0047698 A | 5/2011 |
| KR | 2011-0059261 A | 6/2011 |
| KR | 2011-0068184 A | 6/2011 |

OTHER PUBLICATIONS

Augustin et al., "Control of vascular morphogenesis and homeostasis through the angiopoietin-Tie system", *Nature Reviews Molecular Cell Biology*, 10:165-177 (2009).

Gherardi et al., "Targeting MET in cancer: rationale and progress", *Nature Reviews Cancer*, 12: 89-103 (2012).

Hara et al., "Hypoxia enhances c-Met/HGF receptor expression and signaling by activating HIF-1 in human salivary gland cancer cells", *Oral Oncology*, 42:593-598 (2006).

Holopainen et al., "Effects of Angiopoietin-2-Blocking Antibody on Endothelial Cell-Cell Junctions and Lung Metastasis", *Journal National Cancer Institute*, 104: 461-475 (2012).

Maisonpierre et al., Angiopoietin-2, a Natural Antagonist for Tie2 That Disrupts in vivo Angiogenesis, *Science*, 277:55-60 (1997).

Matsumoto et al., NK4 (HGF-antagonist/angiogenesis inhibitor) in cancer biology and therapeutics, *Cancer Science*, 94(4): 321-327 (2003).

\* cited by examiner

SEQUENCE LISTING

<160> NUMBER OF SEQ ID NOS: 212

<210> SEQ ID NO 1
<211> LENGTH: 5
<212> TYPE: PRT
<213> ORGANISM: Artificial Sequence
<220> FEATURE:
<223> OTHER INFORMATION: heavy chain CDR1 of AbF46

<400> SEQUENCE: 1

Asp Tyr Tyr Met Ser
 1               5

<210> SEQ ID NO 2
<211> LENGTH: 19
<212> TYPE: PRT
<213> ORGANISM: Artificial Sequence
<220> FEATURE:
<223> OTHER INFORMATION: heavy chain CDR2 of AbF46

<400> SEQUENCE: 2

Phe Ile Arg Asn Lys Ala Asn Gly Tyr Thr Thr Glu Tyr Ser Ala Ser
 1               5                  10                  15

Val Lys Gly

<210> SEQ ID NO 3
<211> LENGTH: 6
<212> TYPE: PRT
<213> ORGANISM: Artificial Sequence
<220> FEATURE:
<223> OTHER INFORMATION: heavy chain CDR3 of AbF46

<400> SEQUENCE: 3

Asp Asn Trp Phe Ala Tyr
 1               5

<210> SEQ ID NO 4
<211> LENGTH: 6
<212> TYPE: PRT
<213> ORGANISM: Artificial Sequence
<220> FEATURE:
<223> OTHER INFORMATION: heavy chain CDR1 of c-Met antibody
<220> FEATURE:
<221> NAME/KEY: UNSURE
<222> LOCATION: (1)
<223> OTHER INFORMATION: X is Pro or Ser or absent
<220> FEATURE:
<221> NAME/KEY: UNSURE
<222> LOCATION: (2)
<223> OTHER INFORMATION: X is Glu or Asp

<400> SEQUENCE: 4

Xaa Xaa Tyr Tyr Met Ser
 1               5

<210> SEQ ID NO 5
<211> LENGTH: 8
<212> TYPE: PRT
<213> ORGANISM: Artificial Sequence
<220> FEATURE:
<223> OTHER INFORMATION: heavy chain CDR2 of c-Met antibody
<220> FEATURE:
<221> NAME/KEY: UNSURE
<222> LOCATION: (3)
<223> OTHER INFORMATION: X is Asn or Lys
<220> FEATURE:
<221> NAME/KEY: UNSURE
<222> LOCATION: (4)
<223> OTHER INFORMATION: X is Ala or Val

```
<220> FEATURE:
<221> NAME/KEY: UNSURE
<222> LOCATION: (7)
<223> OTHER INFORMATION: X is Asn or Thr

<400> SEQUENCE: 5

Arg Asn Xaa Xaa Asn Gly Xaa Thr
  1               5

<210> SEQ ID NO 6
<211> LENGTH: 6
<212> TYPE: PRT
<213> ORGANISM: Artificial Sequence
<220> FEATURE:
<223> OTHER INFORMATION: heavy chain CDR3 of c-Met antibody
<220> FEATURE:
<221> NAME/KEY: UNSURE
<222> LOCATION: (5)
<223> OTHER INFORMATION: X is Ser or Thr

<400> SEQUENCE: 6

Asp Asn Trp Leu Xaa Tyr
  1               5

<210> SEQ ID NO 7
<211> LENGTH: 17
<212> TYPE: PRT
<213> ORGANISM: Artificial Sequence
<220> FEATURE:
<223> OTHER INFORMATION: light chain CDR1 of c-Met antibody
<220> FEATURE:
<221> NAME/KEY: UNSURE
<222> LOCATION: (4)
<223> OTHER INFORMATION: X is His, Arg, Gln or Lys
<220> FEATURE:
<221> NAME/KEY: UNSURE
<222> LOCATION: (12)
<223> OTHER INFORMATION: X is His or Gln
<220> FEATURE:
<221> NAME/KEY: UNSURE
<222> LOCATION: (13)
<223> OTHER INFORMATION: X is Lys or Asn
<220> FEATURE:
<221> NAME/KEY: UNSURE
<222> LOCATION: (9)
<223> OTHER INFORMATION: X is Ser or Trp

<400> SEQUENCE: 7

Lys Ser Ser Xaa Ser Leu Leu Ala Xaa Gly Asn Xaa Xaa Asn Tyr Leu
  1               5                  10                  15

Ala

<210> SEQ ID NO 8
<211> LENGTH: 7
<212> TYPE: PRT
<213> ORGANISM: Artificial Sequence
<220> FEATURE:
<223> OTHER INFORMATION: light chain CDR2 of c-Met antibody
<220> FEATURE:
<221> NAME/KEY: UNSURE
<222> LOCATION: (2)
<223> OTHER INFORMATION: X is Ala or Gly
<220> FEATURE:
<221> NAME/KEY: UNSURE
<222> LOCATION: (4)
<223> OTHER INFORMATION: X is Thr or Lys
<220> FEATURE:
<221> NAME/KEY: UNSURE
<222> LOCATION: (7)
<223> OTHER INFORMATION: X is Ser or Pro

<400> SEQUENCE: 8
```

```
Trp Xaa Ser Xaa Arg Val Xaa
  1               5
```

<210> SEQ ID NO 9
<211> LENGTH: 9
<212> TYPE: PRT
<213> ORGANISM: Artificial Sequence
<220> FEATURE:
<223> OTHER INFORMATION: light chain CDR3 of c-Met antibody
<220> FEATURE:
<221> NAME/KEY: UNSURE
<222> LOCATION: (1)
<223> OTHER INFORMATION: X is Gly, Ala or Gln
<220> FEATURE:
<221> NAME/KEY: UNSURE
<222> LOCATION: (6)
<223> OTHER INFORMATION: X is Arg, His, Ser, Ala, Gly or Lys
<220> FEATURE:
<221> NAME/KEY: UNSURE
<222> LOCATION: (8)
<223> OTHER INFORMATION: X is Leu, Tyr, Phe or Met

<400> SEQUENCE: 9

```
Xaa Gln Ser Tyr Ser Xaa Pro Xaa Thr
  1               5
```

<210> SEQ ID NO 10
<211> LENGTH: 17
<212> TYPE: PRT
<213> ORGANISM: Artificial Sequence
<220> FEATURE:
<223> OTHER INFORMATION: light chain CDR1 of AbF46

<400> SEQUENCE: 10

```
Lys Ser Ser Gln Ser Leu Leu Ala Ser Gly Asn Gln Asn Asn Tyr Leu
  1               5                  10                  15

Ala
```

<210> SEQ ID NO 11
<211> LENGTH: 7
<212> TYPE: PRT
<213> ORGANISM: Artificial Sequence
<220> FEATURE:
<223> OTHER INFORMATION: light chain CDR2 of AbF46

<400> SEQUENCE: 11

```
Trp Ala Ser Thr Arg Val Ser
  1               5
```

<210> SEQ ID NO 12
<211> LENGTH: 9
<212> TYPE: PRT
<213> ORGANISM: Artificial Sequence
<220> FEATURE:
<223> OTHER INFORMATION: light chain CDR3 of AbF46

<400> SEQUENCE: 12

```
Gln Gln Ser Tyr Ser Ala Pro Leu Thr
  1               5
```

<210> SEQ ID NO 13
<211> LENGTH: 9
<212> TYPE: PRT
<213> ORGANISM: Artificial Sequence
<220> FEATURE:
<223> OTHER INFORMATION: CDR-L3 derived from L3-1 clone

<400> SEQUENCE: 13

```
Gln Gln Ser Tyr Ser Arg Pro Tyr Thr
  1               5

<210> SEQ ID NO 14
<211> LENGTH: 9
<212> TYPE: PRT
<213> ORGANISM: Artificial Sequence
<220> FEATURE:
<223> OTHER INFORMATION: CDR-L3 derived from L3-2 clone

<400> SEQUENCE: 14

Gly Gln Ser Tyr Ser Arg Pro Leu Thr
  1               5

<210> SEQ ID NO 15
<211> LENGTH: 9
<212> TYPE: PRT
<213> ORGANISM: Artificial Sequence
<220> FEATURE:
<223> OTHER INFORMATION: CDR-L3 derived from L3-3 clone

<400> SEQUENCE: 15

Ala Gln Ser Tyr Ser His Pro Phe Ser
  1               5

<210> SEQ ID NO 16
<211> LENGTH: 9
<212> TYPE: PRT
<213> ORGANISM: Artificial Sequence
<220> FEATURE:
<223> OTHER INFORMATION: CDR-L3 derived from L3-5 clone

<400> SEQUENCE: 16

Gln Gln Ser Tyr Ser Arg Pro Phe Thr
  1               5

<210> SEQ ID NO 17
<211> LENGTH: 117
<212> TYPE: PRT
<213> ORGANISM: Artificial Sequence
<220> FEATURE:
<223> OTHER INFORMATION: heavy chain variable region of anti c-Met
      humanized antibody(huAbF46-H4)

<400> SEQUENCE: 17

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Asp Tyr
             20                  25                  30

Tyr Met Ser Trp Val Arg Gln Ala Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Asp Asn Trp Phe Ala Tyr Trp Gly Gln Gly Thr Leu
            100                 105                 110

Val Thr Val Ser Ser
            115
```

<210> SEQ ID NO 18
<211> LENGTH: 114
<212> TYPE: PRT
<213> ORGANISM: Artificial Sequence
<220> FEATURE:
<223> OTHER INFORMATION: light chain variable region of anti c-Met
      humanized antibody(huAbF46-H4)

<400> SEQUENCE: 18

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg

<210> SEQ ID NO 19
<211> LENGTH: 114
<212> TYPE: PRT
<213> ORGANISM: Artificial Sequence
<220> FEATURE:
<223> OTHER INFORMATION: light chain variable region of anti c-Met
      humanized antibody(huAbF46-H4)

<400> SEQUENCE: 19

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gly Gln
                85                  90                  95

Ser Tyr Ser Arg Pro Leu Thr Phe Gly Gln Gly Thr Lys Val Glu Ile
            100                 105                 110

Lys Arg

<210> SEQ ID NO 20
<211> LENGTH: 114
<212> TYPE: PRT
<213> ORGANISM: Artificial Sequence
<220> FEATURE:
<223> OTHER INFORMATION: light chain variable region of anti c-Met
      humanized antibody(huAbF46-H4)

<400> SEQUENCE: 20

```
Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
             20                  25                  30

Gly Asn Gln Asn Asn Tyr Leu Ala Trp His Gln Lys Pro Gly Lys
         35                  40                  45

Ala Pro Lys Met Leu Ile Ile Trp Ala Ser Thr Arg Val Ser Gly Val
         50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Ala Gln
                 85                  90                  95

Ser Tyr Ser His Pro Phe Ser Phe Gly Gln Gly Thr Lys Val Glu Ile
             100                 105                 110

Lys Arg
```

```
<210> SEQ ID NO 21
<211> LENGTH: 114
<212> TYPE: PRT
<213> ORGANISM: Artificial Sequence
<220> FEATURE:
<223> OTHER INFORMATION: light chain variable region of anti c-Met
      humanized antibody(huAbF46-H4)

<400> SEQUENCE: 21
```

```
Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
             20                  25                  30

Gly Asn Gln Asn Asn Tyr Leu Ala Trp His Gln Lys Pro Gly Lys
         35                  40                  45

Ala Pro Lys Met Leu Ile Ile Trp Ala Ser Thr Arg Val Ser Gly Val
         50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Phe Thr Phe Gly Gln Gly Thr Lys Val Glu Ile
             100                 105                 110

Lys Arg
```

```
<210> SEQ ID NO 22
<211> LENGTH: 6
<212> TYPE: PRT
<213> ORGANISM: Artificial Sequence
<220> FEATURE:
<223> OTHER INFORMATION: CDR-H1 derived from H11-4 clone

<400> SEQUENCE: 22

Pro Glu Tyr Tyr Met Ser
 1               5
```

```
<210> SEQ ID NO 23
<211> LENGTH: 6
<212> TYPE: PRT
<213> ORGANISM: Artificial Sequence
<220> FEATURE:
<223> OTHER INFORMATION: CDR-H1 derived from YC151 clone
```

```
<400> SEQUENCE: 23

Pro Asp Tyr Tyr Met Ser
 1               5

<210> SEQ ID NO 24
<211> LENGTH: 6
<212> TYPE: PRT
<213> ORGANISM: Artificial Sequence
<220> FEATURE:
<223> OTHER INFORMATION: CDR-H1 derived from YC193 clone

<400> SEQUENCE: 24

Ser Asp Tyr Tyr Met Ser
 1               5

<210> SEQ ID NO 25
<211> LENGTH: 8
<212> TYPE: PRT
<213> ORGANISM: Artificial Sequence
<220> FEATURE:
<223> OTHER INFORMATION: CDR-H2 derived from YC244 clone

<400> SEQUENCE: 25

Arg Asn Asn Ala Asn Gly Asn Thr
 1               5

<210> SEQ ID NO 26
<211> LENGTH: 8
<212> TYPE: PRT
<213> ORGANISM: Artificial Sequence
<220> FEATURE:
<223> OTHER INFORMATION: CDR-H2 derived from YC321 clone

<400> SEQUENCE: 26

Arg Asn Lys Val Asn Gly Tyr Thr
 1               5

<210> SEQ ID NO 27
<211> LENGTH: 6
<212> TYPE: PRT
<213> ORGANISM: Artificial Sequence
<220> FEATURE:
<223> OTHER INFORMATION: CDR-H3 derived from YC354 clone

<400> SEQUENCE: 27

Asp Asn Trp Leu Ser Tyr
 1               5

<210> SEQ ID NO 28
<211> LENGTH: 6
<212> TYPE: PRT
<213> ORGANISM: Artificial Sequence
<220> FEATURE:
<223> OTHER INFORMATION: CDR-H3 derived from YC374 clone

<400> SEQUENCE: 28

Asp Asn Trp Leu Thr Tyr
 1               5

<210> SEQ ID NO 29
<211> LENGTH: 17
<212> TYPE: PRT
<213> ORGANISM: Artificial Sequence
<220> FEATURE:
<223> OTHER INFORMATION: CDR-L1 derived from L1-1 clone

<400> SEQUENCE: 29
```

Lys Ser Ser His Ser Leu Leu Ala Ser Gly Asn Gln Asn Asn Tyr Leu
 1               5                  10                  15
Ala

<210> SEQ ID NO 30
<211> LENGTH: 17
<212> TYPE: PRT
<213> ORGANISM: Artificial Sequence
<220> FEATURE:
<223> OTHER INFORMATION: CDR-L1 derived from L1-3 clone

<400> SEQUENCE: 30

Lys Ser Ser Arg Ser Leu Leu Ser Gly Asn His Lys Asn Tyr Leu
 1               5                  10                  15
Ala

<210> SEQ ID NO 31
<211> LENGTH: 17
<212> TYPE: PRT
<213> ORGANISM: Artificial Sequence
<220> FEATURE:
<223> OTHER INFORMATION: CDR-L1 derived from L1-4 clone

<400> SEQUENCE: 31

Lys Ser Ser Lys Ser Leu Leu Ala Ser Gly Asn Gln Asn Asn Tyr Leu
 1               5                  10                  15
Ala

<210> SEQ ID NO 32
<211> LENGTH: 17
<212> TYPE: PRT
<213> ORGANISM: Artificial Sequence
<220> FEATURE:
<223> OTHER INFORMATION: CDR-L1 derived from L1-12 clone

<400> SEQUENCE: 32

Lys Ser Ser Arg Ser Leu Leu Ala Ser Gly Asn Gln Asn Asn Tyr Leu
 1               5                  10                  15
Ala

<210> SEQ ID NO 33
<211> LENGTH: 17
<212> TYPE: PRT
<213> ORGANISM: Artificial Sequence
<220> FEATURE:
<223> OTHER INFORMATION: CDR-L1 derived from L1-22 clone

<400> SEQUENCE: 33

Lys Ser Ser His Ser Leu Leu Ala Ser Gly Asn Gln Asn Asn Tyr Leu
 1               5                  10                  15
Ala

<210> SEQ ID NO 34
<211> LENGTH: 7
<212> TYPE: PRT
<213> ORGANISM: Artificial Sequence
<220> FEATURE:
<223> OTHER INFORMATION: CDR-L2 derived from L2-9 clone

<400> SEQUENCE: 34

Trp Ala Ser Lys Arg Val Ser
 1               5

```
<210> SEQ ID NO 35
<211> LENGTH: 7
<212> TYPE: PRT
<213> ORGANISM: Artificial Sequence
<220> FEATURE:
<223> OTHER INFORMATION: CDR-L2 derived from L2-12 clone

<400> SEQUENCE: 35

Trp Gly Ser Thr Arg Val Ser
 1               5

<210> SEQ ID NO 36
<211> LENGTH: 7
<212> TYPE: PRT
<213> ORGANISM: Artificial Sequence
<220> FEATURE:
<223> OTHER INFORMATION: CDR-L2 derived from L2-16 clone

<400> SEQUENCE: 36

Trp Gly Ser Thr Arg Val Pro
 1               5

<210> SEQ ID NO 37
<211> LENGTH: 9
<212> TYPE: PRT
<213> ORGANISM: Artificial Sequence
<220> FEATURE:
<223> OTHER INFORMATION: CDR-L3 derived from L3-32 clone

<400> SEQUENCE: 37

Gln Gln Ser Tyr Ser Lys Pro Phe Thr
 1               5

<210> SEQ ID NO 38
<211> LENGTH: 1416
<212> TYPE: DNA
<213> ORGANISM: Artificial Sequence
<220> FEATURE:
<223> OTHER INFORMATION: nucleotide sequence of heavy chain of chAbF46
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop sodon
<220> FEATURE:
<221> NAME/KEY: misc_feature
<222> LOCATION: (1411)..(1416)
<223> OTHER INFORMATION: XhoI restriction site

<400> SEQUENCE: 38
gaattcgccg ccaccatgga atggagctgg gttttttctcg taacactttt aaatggtatc    60
```

```
cagtgtgagg tgaagctggt ggagtctgga ggaggcttgg tacagcctgg gggttctctg      120
agactctcct gtgcaacttc tgggttcacc ttcactgatt actacatgag ctgggtccgc      180
cagcctccag gaaaggcact tgagtggttg ggttttatta gaaacaaagc taatggttac      240
acaacagagt acagtgcatc tgtgaagggt cggttcacca tctccagaga taattcccaa      300
agcatcctct atcttcaaat ggacaccctg agagctgagg acagtgccac ttattactgt      360
gcaagagata actggtttgc ttactggggc caagggactc tggtcactgt ctctgcagct      420
agcaccaagg gcccatcggt cttccccctg gcaccctcct ccaagagcac ctctgggggc      480
acagcggccc tgggctgcct ggtcaaggac tacttccccg aaccggtgac ggtgtcgtgg      540
aactcaggcg ccctgaccag cggcgtgcac accttcccgg ctgtcctaca gtcctcagga      600
ctctactccc tcagcagcgt ggtgaccgtg ccctccagca gcttgggcac ccagacctac      660
atctgcaacg tgaatcacaa gcccagcaac accaaggtgg acaagaaagt tgagcccaaa      720
tcttgtgaca aaactcacac atgcccaccg tgcccagcac ctgaactcct ggggggaccg      780
tcagtcttcc tcttccccccc aaaacccaag gacaccctca tgatctcccg gacccctgag      840
gtcacatgcg tggtggtgga cgtgagccac gaagaccctg aggtcaagtt caactggtac      900
gtggacggcg tggaggtgca taatgccaag acaaagccgc gggaggagca gtacaacagc      960
acgtaccgtg tggtcagcgt cctcaccgtc ctgcaccagg actggctgaa tggcaaggag     1020
tacaagtgca aggtctccaa caaagccctc ccagcccccca tcgagaaaac catctccaaa     1080
gccaaagggc agccccgaga accacaggtg tacaccctgc ccccatcccg ggaggagatg     1140
accaagaacc aggtcagcct gacctgcctg gtcaaaggct tctatcccag cgacatcgcc     1200
gtggagtggg agagcaatgg gcagccggag aacaactaca agaccacgcc tcccgtgctg     1260
gactccgacg gctccttctt cctctacagc aagctcaccg tggacaagag caggtggcag     1320
caggggaacg tcttctcatg ctccgtgatg catgaggctc tgcacaacca ctacacgcag     1380
aagagcctct ccctgtctcc gggtaaatga ctcgag                                1416
```

```
<210> SEQ ID NO 39
<211> LENGTH: 759
<212> TYPE: DNA
<213> ORGANISM: Artificial Sequence
<220> FEATURE:
<223> OTHER INFORMATION: nucleotide sequence of light chain of chAbF46
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
```

```
<222> LOCATION: (754)..(759)
<223> OTHER INFORMATION: XhoI restriction site

<400> SEQUENCE: 39
gaattcacta gtgattaatt cgccgccacc atggattcac aggcccaggt cctcatgttg      60
ctgctgctat cggtatctgg tacctgtgga gacattttga tgacccagtc tccatcctcc     120
ctgactgtgt cagcaggaga gaaggtcact atgagctgca agtccagtca gagtctttta     180
gctagtggca accaaaataa ctacttggcc tggcaccagc agaaaccagg acgatctcct     240
aaaatgctga taatttgggc atccactagg gtatctggag tccctgatcg cttcataggc     300
agtggatctg ggacggattt cactctgacc atcaacagtg tgcaggctga agatctggct     360
gtttattact gtcagcagtc ctacagcgct ccgctcacgt tcggtgctgg gaccaagctg     420
gagctgaaac gtacggtggc tgcaccatct gtcttcatct tcccgccatc tgatgagcag     480
ttgaaatctg gaactgcctc tgttgtgtgc ctgctgaata acttctatcc cagagaggcc     540
aaagtacagt ggaaggtgga taacgccctc caatcgggta actcccagga gagtgtcaca     600
gagcaggaca gcaaggacag cacctacagc ctcagcagca ccctgacgct gagcaaagca     660
gactacgaga aacacaaagt ctacgcctgc gaagtcaccc atcagggcct gagctcgccc     720
gtcacaaaga gcttcaacag gggagagtgt tgactcgag                            759

<210> SEQ ID NO 40
<211> LENGTH: 447
<212> TYPE: PRT
<213> ORGANISM: Artificial Sequence
<220> FEATURE:
<223> OTHER INFORMATION: amino acid sequence of H1-heavy

<400> SEQUENCE: 40
```

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
        260                 265                 270

Val Lys Phe Asn Trp Tyr Val Asp Gly Val Glu Val His Asn Ala Lys
    275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Arg Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys
    435                 440                 445

<210> SEQ ID NO 41
<211> LENGTH: 447
<212> TYPE: PRT
<213> ORGANISM: Artificial Sequence
<220> FEATURE:
<223> OTHER INFORMATION: amino acid sequence of H3-heavy

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

```
Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 42
<211> LENGTH: 447
<212> TYPE: PRT
<213> ORGANISM: Artificial Sequence
<220> FEATURE:
<223> OTHER INFORMATION: amino acid sequence of H4-heavy

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45
```

```
Gly Phe Ile Arg Asn Lys Ala Asn Gly Tyr Thr Thr Glu Tyr Ser Ala
 50                  55                  60
Ser Val Lys Gly Arg Phe Thr Ile Ser Arg Asp Asn Ser Lys Asn Thr
 65                  70                  75                  80
Leu Tyr Leu Gln Met Asn Ser Leu Arg Ala Glu Asp Thr Ala Val Tyr
                 85                  90                  95
Tyr Cys Ala Arg Asp Asn Trp Phe Ala Tyr Trp Gly Gln Gly Thr Leu
                100                 105                 110
Val Thr Val Ser Ser Ala Ser Thr Lys Gly Pro Ser Val Phe Pro Leu
             115                 120                 125
Ala Pro Ser Ser Lys Ser Thr Ser Gly Gly Thr Ala Ala Leu Gly Cys
130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Lys Val Glu Pro Lys Ser Cys Asp Lys Thr His
    210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445

<210> SEQ ID NO 43
<211> LENGTH: 220
```

```
<212> TYPE: PRT
<213> ORGANISM: Artificial Sequence
<220> FEATURE:
<223> OTHER INFORMATION: amino acid sequence of H1-light

<400> SEQUENCE: 43

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 44
<211> LENGTH: 220
<212> TYPE: PRT
<213> ORGANISM: Artificial Sequence
<220> FEATURE:
<223> OTHER INFORMATION: amino acid sequence of H2-light

<400> SEQUENCE: 44

Asp Ile Val Met Thr Gln Thr Pro Leu Ser Leu Pro Val Thr Pro Gly
 1               5                  10                  15

Glu Pro Ala Ser Ile Ser Cys Lys Ser Ser Gln Ser Leu Leu Ala Ser
            20                  25                  30

Gly Asn Gln Asn Asn Tyr Leu Ala Trp His Leu Gln Lys Pro Gly Gln
        35                  40                  45

Ser Pro Gln Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

Ser Tyr Ser Ala Pro Leu Thr Phe Gly Gln Gly Thr Lys Leu Glu Leu
            100                 105                 110
```

```
Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 45
<211> LENGTH: 220
<212> TYPE: PRT
<213> ORGANISM: Artificial Sequence
<220> FEATURE:
<223> OTHER INFORMATION: amino acid sequence of H3-light

<400> SEQUENCE: 45

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp Tyr Gln Gln Lys Pro Gly Gln
        35                  40                  45

Pro Pro Lys Leu Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 46
<211> LENGTH: 219
<212> TYPE: PRT
<213> ORGANISM: Artificial Sequence
```

```
<220> FEATURE:
<223> OTHER INFORMATION: amino acid sequence of H4-light

<400> SEQUENCE: 46

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
 65                 70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu
    210                 215

<210> SEQ ID NO 47
<211> LENGTH: 1350
<212> TYPE: DNA
<213> ORGANISM: Artificial Sequence
<220> FEATURE:
<223> OTHER INFORMATION: nucleotide sequence of H1-heavy

<400> SEQUENCE: 47
gaggtgcagc tggtggagtc tgggggaggc ttggtccagc ctggagggtc cctgagactc      60
tcctgtgcag cctctggatt caccttcact gactactaca tgagctgggt ccgccaggct     120
ccagggaagg ggctggagtg gttgggcttt attagaaaca agctaacgg ttacaccaca      180 gaatacagtg cgtctgtgaa aggcagattc accatctcaa gagataattc aaagaactca     240
ctgtatctgc aaatgaacag cctgaaaacc gaggacacgg ccgtgtatta ctgtgctaga     300
gataactggt tgcttactg ggtcaagga accctggtca ccgtctcctc ggctagcacc       360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt     660
```

| | |
|---|---|
| gacaaaactc acacatgccc accgtgccca gcacctgaac tcctgggggg accgtcagtc | 720 |
| ttcctcttcc ccccaaaacc caaggacacc ctcatgatct cccggacccc tgaggtcaca | 780 |
| tgcgtggtgg tggacgtgag ccacgaagac cctgaggtca agttcaactg gtacgtggac | 840 |
| ggcgtggagg tgcataatgc caagacaaag ccgcgggagg agcagtacaa cagcacgtac | 900 |
| cgtgtggtca gcgtcctcac cgtcctgcac caggactggc tgaatggcaa ggagtacaag | 960 |
| tgcaaggtct ccaacaaagc cctcccagcc cccatcgaga aaaccatctc caaagccaaa | 1020 |
| gggcagcccc gagaaccaca ggtgtacacc ctgcccccat cccgggagga gatgaccaag | 1080 |
| aaccaggtca gcctgacctg cctggtcaaa ggcttctatc ccagcgacat cgccgtggag | 1140 |
| tgggagagca atgggcagcc ggagaacaac tacaagacca cgcctcccgt gctggactcc | 1200 |
| gacggctcct tcttcctcta cagcaagctc accgtggaca agagcaggtg gcagcagggg | 1260 |
| aacgtcttct catgctccgt gatgcatgag gctctgcaca accactacac gcagaagagc | 1320 |
| ctctccctgt ctccgggtaa atgactcgag | 1350 |

<210> SEQ ID NO 48
<211> LENGTH: 1350
<212> TYPE: DNA
<213> ORGANISM: Artificial Sequence
<220> FEATURE:
<223> OTHER INFORMATION: nucleotide sequence of H3-heavy

<400> SEQUENCE: 48

| | |
|---|---|
| gaggtgcagc tggtggagtc tgggggaggc ttggtccagc ctggagggtc cctgagactc | 60 |
| tcctgtgcag cctctggatt caccttcact gactactaca tgagctgggt ccgccaggct | 120 |
| ccagggaagg ggctggagtg ggttgggctt attagaaaca agctaacgg ttacaccaca | 180 |
| gaatacagtg cgtctgtgaa aggcagattc accatctcaa gagataattc aaagaactca | 240 |
| ctgtatctgc aaatgaacag cctgcgtgct gaggacacgg ccgtgtatta ctgtgctaga | 300 |
| gataactggt tgcttactg gggtcaagga accctggtca ccgtctcctc ggctagcacc | 360 |
| aagggcccat cggtcttccc cctggcaccc tcctccaaga gcacctctgg gggcacagcg | 420 |
| gccctgggct gcctggtcaa ggactacttc cccgaaccgg tgacggtgtc gtggaactca | 480 |
| ggcgccctga ccagcggcgt gcacaccttc ccggctgtcc tacagtcctc aggactctac | 540 |
| tccctcagca gcgtggtgac cgtgccctcc agcagcttgg gcacccagac ctacatctgc | 600 |
| aacgtgaatc acaagcccag caacaccaag gtggacaaga agttgagcc caaatcttgt | 660 |
| gacaaaactc acacatgccc accgtgccca gcacctgaac tcctgggggg accgtcagtc | 720 |
| ttcctcttcc ccccaaaacc caaggacacc ctcatgatct cccggacccc tgaggtcaca | 780 |
| tgcgtggtgg tggacgtgag ccacgaagac cctgaggtca agttcaactg gtacgtggac | 840 |
| ggcgtggagg tgcataatgc caagacaaag ccgcgggagg agcagtacaa cagcacgtac | 900 |
| cgtgtggtca gcgtcctcac cgtcctgcac caggactggc tgaatggcaa ggagtacaag | 960 |
| tgcaaggtct ccaacaaagc cctcccagcc cccatcgaga aaaccatctc caaagccaaa | 1020 |
| gggcagcccc gagaaccaca ggtgtacacc ctgcccccat cccgggagga gatgaccaag | 1080 |
| aaccaggtca gcctgacctg cctggtcaaa ggcttctatc ccagcgacat cgccgtggag | 1140 |
| tgggagagca atgggcagcc ggagaacaac tacaagacca cgcctcccgt gctggactcc | 1200 |
| gacggctcct tcttcctcta cagcaagctc accgtggaca agagcaggtg gcagcagggg | 1260 |
| aacgtcttct catgctccgt gatgcatgag gctctgcaca accactacac gcagaagagc | 1320 |
| ctctccctgt ctccgggtaa atgactcgag | 1350 |

<210> SEQ ID NO 49
<211> LENGTH: 1350
<212> TYPE: DNA
<213> ORGANISM: Artificial Sequence
<220> FEATURE:
<223> OTHER INFORMATION: nucleotide sequence of H4-heavy

<400> SEQUENCE: 49

```
gaggttcagc tggtggagtc tggcggtggc ctggtgcagc cagggggctc actccgtttg      60
tcctgtgcag cttctggctt caccttcact gattactaca tgagctgggt gcgtcaggcc     120
ccgggtaagg gcctggaatg gttgggtttt attagaaaca agctaatgg ttacacaaca      180
gagtacagtg catctgtgaa gggtcgtttc actataagca gagataattc caaaaacaca     240
ctgtacctgc agatgaacag cctgcgtgct gaggacactg ccgtctatta ttgtgctaga     300
gataactggt ttgcttactg gggccaaggg actctggtca ccgtctcctc ggctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt      660
gacaaaactc acacatgccc accgtgccca gcacctgaac tcctgggggg accgtcagtc     720
ttcctcttcc cccaaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcggagg agcagtacaa cagcacgtac      900
cgtgtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
gggcagcccc gagaaccaca ggtgtacacc ctgcccccat cccgggagga gatgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca agagcaggtg gcagcagggg    1260
aacgtcttct catgctccgt gatgcatgag gctctgcaca accactacac gcagaagagc    1320
ctctccctgt ctccgggtaa atgactcgag                                      1350
```

<210> SEQ ID NO 50
<211> LENGTH: 669
<212> TYPE: DNA
<213> ORGANISM: Artificial Sequence
<220> FEATURE:
<223> OTHER INFORMATION: nucleotide sequence of H1-light

<400> SEQUENCE: 50

```
gacatcgtga tgacccagtc tccagactcc ctggctgtgt ctctgggcga gagggccacc      60
atcaactgca gtccagcca gagtcttta gctagcggca accaaaataa ctacttagct      120
tggcaccagc agaaaccagg acagcctcct aagatgctca tatttgggc atctacccgg      180
gtatccgggg tccctgaccg attcagtggc agcgggtctg ggacagattt cactctcacc      240
atcagcagcc tgcaggctga agatgtggca gtttattact gtcagcaatc ctatagtgct      300
cctctcacgt tcggaggcgg taccaaggtg gagatcaaac gtacggtggc tgcaccatct      360
```

```
gtcttcatct tcccgccatc tgatgagcag ttgaaatctg aactgcctc tgttgtgtgc      420 ctgctgaata acttctatcc cagagaggcc aaagtacagt ggaaggtgga taacgccctc      480
caatcgggta actcccagga gagtgtcaca gagcaggaca gcaaggacag cacctacagc      540
ctcagcagca ccctgacgct gagcaaagca gactacgaga acacaaagt ctacgcctgc       600 gaagtcaccc atcagggcct gagctcgccc gtcacaaaga gcttcaacag gggagagtgt      660
tgactcgag                                                              669

<210> SEQ ID NO 51
<211> LENGTH: 669
<212> TYPE: DNA
<213> ORGANISM: Artificial Sequence
<220> FEATURE:
<223> OTHER INFORMATION: nucleotide sequence of H2-light

<400> SEQUENCE: 51
gatattgtga tgacccagac tccactctcc ctgcccgtca cccctggaga gccggcctcc       60
atctcctgca gtccagtca gagtctttta gctagtggaa ccaaaataa ctacttggcc        120 tggcacctgc agaagccagg gcagtctcca cagatgctga tcatttgggc atccactagg      180
gtatctggag tcccagacag gttcagtggc agtgggtcag gcactgattt cacactgaaa      240
atcagcaggg tggaggctga ggatgttgga gtttattact gccagcagtc ctacagcgct      300
ccgctcacgt tcggacaggg taccaagctg gagctcaaac gtacggtggc tgcaccatct      360
gtcttcatct tcccgccatc tgatgagcag ttgaaatctg gaactgcctc tgttgtgtgc      420
ctgctgaata acttctatcc cagagaggcc aaagtacagt ggaaggtgga taacgccctc      480
caatcgggta actcccagga gagtgtcaca gagcaggaca gcaaggacag cacctacagc      540
ctcagcagca ccctgacgct gagcaaagca gactacgaga acacaaagt ctacgcctgc       600 gaagtcaccc atcagggcct gagctcgccc gtcacaaaga gcttcaacag gggagagtgt      660
tgactcgag                                                              669

<210> SEQ ID NO 52
<211> LENGTH: 669
<212> TYPE: DNA
<213> ORGANISM: Artificial Sequence
<220> FEATURE:
<223> OTHER INFORMATION: nucleotide sequence of H3-light

<400> SEQUENCE: 52
gacatcgtga tgacccagtc tccagactcc ctggctgtgt ctctgggcga gagggccacc      60
atcaactgca gtccagcca gagtctttta gctagcggca accaaaataa ctacttagct       120
tggtaccagc agaaaccagg acagcctcct aagctgctca tatttgggc atctacccgg       180 gtatccgggg tccctgaccg attcagtggc agcgggtctg ggacagattt cactctcacc      240
atcagcagcc tgcaggctga agatgtggca gtttattact gtcagcaatc ctatagtgct      300
cctctcacgt tcggaggcgg taccaaggtg gagatcaaac gtacggtggc tgcaccatct      360
gtcttcatct tcccgccatc tgatgagcag ttgaaatctg gaactgcctc tgttgtgtgc      420
ctgctgaata acttctatcc cagagaggcc aaagtacagt ggaaggtgga taacgccctc      480
caatcgggta actcccagga gagtgtcaca gagcaggaca gcaaggacag cacctacagc      540
ctcagcagca ccctgacgct gagcaaagca gactacgaga acacaaagt ctacgcctgc       600 gaagtcaccc atcagggcct gagctcgccc gtcacaaaga gcttcaacag gggagagtgt      660
tgactcgag                                                              669
```

<210> SEQ ID NO 53
<211> LENGTH: 669
<212> TYPE: DNA
<213> ORGANISM: Artificial Sequence
<220> FEATURE:
<223> OTHER INFORMATION: nucleotide sequence of H4-light

<400> SEQUENCE: 53

```
gatatccaga tgacccagtc cccgagctcc ctgtccgcct ctgtgggcga tagggtcacc        60
atcacctgca agtccagtca gagtctttta gctagtggca accaaaataa ctacttggcc       120
tggcaccaac agaaaccagg aaaagctccg aaaatgctga ttatttgggc atccactagg       180
gtatctggag tccttctcg cttctctgga tccgggtctg ggacggattt cactctgacc        240
atcagcagtc tgcagccgga agacttcgca acttattact gtcagcagtc ctacagcgct       300
ccgctcacgt tcggacaggg taccaaggtg gagatcaaac gtacggtggc tgcaccatct       360
gtcttcatct tcccgccatc tgatgagcag ttgaaatctg gaactgcctc tgttgtgtgc       420
ctgctgaata acttctatcc cagagaggcc aaagtacagt ggaaggtgga taacgccctc       480
caatcgggta actcccagga gagtgtcaca gagcaggaca gcaaggacag cacctacagc       540
ctcagcagca ccctgacgct gagcaaagca gactacgaga acacaaagt ctacgcctgc        600 gaagtcaccc atcagggcct gagctcgccc gtcacaaaga gcttcaacag gggagagtgt       660
tgactcgag                                                               669
```

<210> SEQ ID NO 54
<211> LENGTH: 23
<212> TYPE: PRT
<213> ORGANISM: Artificial Sequence
<220> FEATURE:
<223> OTHER INFORMATION: linker between VH and VL

<400> SEQUENCE: 54

```
Gly Leu Gly Gly Leu Gly Gly Gly Ser Gly Gly Gly Ser Gly
 1               5                  10                  15

Gly Ser Ser Gly Val Gly Ser
            20
```

<210> SEQ ID NO 55
<211> LENGTH: 1088
<212> TYPE: DNA
<213> ORGANISM: Artificial Sequence
<220> FEATURE:
<223> OTHER INFORMATION: polynucleotide encoding scFv of huAbF46
      antibody

<400> SEQUENCE: 55

```
gctagcgttt tagcagaagt tcaattggtt gaatctggtg gtggtttggt tcaaccaggt        60
ggttctttga gattgtcttg tgctgcttct ggttttactt tcaccgatta ttacatgtcc       120
tgggttagac aagctccagg taaaggtttg aatggttgg gtttcattag aaacaaggct        180
aacggttaca ctaccgaata ttctgcttct gttaaggta gattcaccat ttctagagac       240
aactctaaga cacccttgta cttgcaaatg aactccttga gagctgaaga tactgctgtt       300
tattactgcg ctagagataa ttggtttgct tattgggtc aaggtacttt ggttactgtt       360
tcttctggcc tcgggggcct cggaggagga ggtagtggcg gaggaggctc cggtggatcc       420
agcggtgtgg gttccgatat tcaaatgacc caatctccat cttctttgtc tgcttcagtt       480
ggtgatagag ttaccattac ttgtaagtcc tcccaatctt tgttggcttc tggtaatcag       540
```

```
aacaattact tggcttggca tcaacaaaaa ccaggtaaag ctccaaagat gttgattatt    600
tgggcttcta ccagagtttc tggtgttcca tctagatttt ctggttctgg ttccggtact    660
gattttactt tgaccatttc atccttgcaa ccagaagatt tcgctactta ctactgtcaa    720
caatcttact ctgctccatt gacttttggt caaggtacaa aggtcgaaat caagagagaa    780
ttcggtaagc ctatccctaa ccctctcctc ggtctcgatt ctacgggtgg tggtggatct    840
ggtggtggtg ttctggtgg tggtggttct caggaactga caactatatg cgagcaaatc     900
ccctcaccaa ctttagaatc gacgccgtac tctttgtcaa cgactactat tttggccaac    960
gggaaggcaa tgcaaggagt ttttgaatat tacaaatcag taacgtttgt cagtaattgc   1020
ggttctcacc cctcaacaac tagcaaaggc agccccataa acacacagta tgtttttttga  1080 gtttaaac                                                            1088
```

<210> SEQ ID NO 56
<211> LENGTH: 5597
<212> TYPE: DNA
<213> ORGANISM: Artificial Sequence
<220> FEATURE:
<223> OTHER INFORMATION: expression vector including polynucleotide
      encoding scFv of huAbF46 antibody
<220> FEATURE:
<221> NAME/KEY: misc_difference
<222> LOCATION: (573)..(578)
<223> OTHER INFORMATION: NheI restriction site
<220> FEATURE:
<221> NAME/KEY: misc_difference
<222> LOCATION: (588)..(938)
<223> OTHER INFORMATION: huAbF46 VH
<220> FEATURE:
<221> NAME/KEY: misc_difference
<222> LOCATION: (939)..(1007)
<223> OTHER INFORMATION: linker
<220> FEATURE:
<221> NAME/KEY: misc_difference
<222> LOCATION: (1008)..(1349)
<223> OTHER INFORMATION: huAbF46 VL
<220> FEATURE:
<221> NAME/KEY: misc_difference
<222> LOCATION: (1350)..(1355)
<223> OTHER INFORMATION: EcoRI restriction site
<220> FEATURE:
<221> NAME/KEY: misc_difference
<222> LOCATION: (1356)..(1397)
<223> OTHER INFORMATION: V5 epitope
<220> FEATURE:
<221> NAME/KEY: misc_difference
<222> LOCATION: (1398)..(1442)
<223> OTHER INFORMATION: (G4S)3 linker
<220> FEATURE:
<221> NAME/KEY: misc_difference
<222> LOCATION: (1443)..(1649)
<223> OTHER INFORMATION: Aga2
<220> FEATURE:
<221> NAME/KEY: misc_difference
<222> LOCATION: (1650)..(1652)
<223> OTHER INFORMATION: TGA(stop codon)
<220> FEATURE:
<221> NAME/KEY: misc_difference
<222> LOCATION: (1653)..(1660)
<223> OTHER INFORMATION: PmeI restriction site

<400> SEQUENCE: 56

```
acggattaga agccgccgag cgggtgacag ccctccgaag gaagactctc ctccgtgcgt     60
cctcgtcttc accggtcgcg ttcctgaaac gcagatgtgc ctcgcgccgc actgctccga   120
acaataaaga ttctacaata ctagctttta tggttatgaa gaggaaaaat tggcagtaac   180
ctggccccac aaaccttcaa atgaacgaat caaattaaca accataggat gataatgcga   240
```

```
ttagtttttt agccttattt ctggggtaat taatcagcga agcgatgatt tttgatctat        300
taacagatat ataaatgcaa aaactgcata accactttaa ctaatacttt caacattttc        360
ggtttgtatt acttcttatt caaatgtaat aaaagtatca acaaaaaatt gttaatatac        420
ctctatactt taacgtcaag gagaaaaaac cccggatcgg actactagca gctgtaatac        480
gactcactat agggaatatt aagctaattc tacttcatac attttcaatt aagatgcagt        540
tacttcgctg ttttcaata ttttctgtta ttgctagcgt tttagcagaa gttcaattgg        600
ttgaatctgg tggtggtttg gttcaaccag gtggttcttt gagattgtct tgtgctgctt        660
ctggttttac tttcaccgat tattacatgt cctgggttag acaagctcca ggtaaaggtt        720
tggaatggtt gggtttcatt agaaacaagg ctaacggtta cactaccgaa tattctgctt        780
ctgttaaggg tagattcacc atttctagag acaactctaa gaacaccttg tacttgcaaa        840
tgaactcctt gagagctgaa gatactgctg tttattactg cgctagagat aattggtttg        900
cttattgggg tcaaggtact ttggttactg tttcttctgg cctcggggc ctcggaggag        960 gaggtagtgg cggaggaggc tccggtggat ccagcggtgt gggttccgat attcaaatga       1020
cccaatctcc atcttctttg tctgcttcag ttggtgatag agttaccatt acttgtaagt       1080
cctcccaatc tttgttggct tctggtaatc agaacaatta cttggcttgg catcaacaaa       1140
aaccaggtaa agctccaaag atgttgatta tttgggcttc taccagagtt tctggtgttc       1200
catctagatt ttctggttct ggttccggta ctgattttac tttgaccatt tcatccttgc       1260
aaccagaaga tttcgctact tactactgtc aacaatctta ctctgctcca ttgacttttg       1320
gtcaaggtac aaaggtcgaa atcaagagag aattcggtaa gcctatccct aaccctctcc       1380
tcggtctcga ttctacgggt ggtggtggat ctggtggtgg tggttctggt ggtggtggtt       1440
ctcaggaact gacaactata tgcgagcaaa tcccctcacc aactttagaa tcgacgccgt       1500
actctttgtc aacgactact attttggcca acgggaaggc aatgcaagga ttttttgaat       1560
attacaaatc agtaacgttt gtcagtaatt gcggttctca cccctcaaca actagcaaag       1620
gcagccccat aaacacacag tatgtttttt gagtttaaac ccgctgatct gataacaaca       1680
gtgtagatgt aacaaaatcg actttgttcc cactgtactt ttagctcgta caaaatacaa       1740 tatactttc atttctccgt aaacaacatg ttttcccatg taatatcctt ttctattttt       1800
cgttccgtta ccaactttac acatacttta tatagctatt cacttctata cactaaaaaa       1860
ctaagacaat tttaattttg ctgcctgcca tatttcaatt tgttataaat tcctataatt       1920
tatcctatta gtagctaaaa aaagatgaat gtgaatcgaa tcctaagaga attgggcaag       1980
tgcacaaaca atacttaaat aaatactact cagtaataac ctatttctta gcattttga       2040 cgaaatttgc tattttgtta gagtctttta ccacatttgt ctccacacct ccgcttacat       2100
caacaccaat aacgccattt aatctaagcg catcaccaac attttctggc gtcagtccac       2160
cagctaacat aaaatgtaag ctctcggggc tctcttgcct tccaacccag tcagaaatcg       2220
agttccaatc caaaagttca cctgtcccac ctgcttctga atcaaacaag ggaataaacg       2280
aatgaggttt ctgtgaagct gcactgagta gtatgttgca gtcttttgga aatacgagtc       2340
ttttaataac tggcaaaccg aggaactctt ggtattcttg ccacgactca tctccgtgca       2400
gttggacgat atcaatgccg taatcattga ccagagccaa acatcctcc ttaggttgat       2460 tacgaaacac gccaaccaag tatttcggag tgcctgaact attttttatat gcttttacaa       2520 gacttgaaat tttccttgca ataaccgggt caattgttct ctttctattg ggcacacata       2580
```

```
taatacccag caagtcagca tcggaatcta gagcacattc tgcggcctct gtgctctgca    2640
agccgcaaac tttcaccaat ggaccagaac tacctgtgaa attaataaca gacatactcc    2700
aagctgcctt tgtgtgctta atcacgtata ctcacgtgct caatagtcac caatgccctc    2760
cctcttggcc ctctccttt ctttttcga ccgaatttct tgaagacgaa agggcctcgt      2820
gatacgccta ttttatagg ttaatgtcat gataataatg gtttcttagg acggatcgct     2880
tgcctgtaac ttacacgcgc ctcgtatctt ttaatgatgg aataatttgg gaatttactc    2940
tgtgtttatt tattttatg ttttgtattt ggattttaga aagtaaataa agaaggtaga     3000
agagttacgg aatgaagaaa aaaaaataaa caaaggttta aaaatttca acaaaaagcg     3060 tactttacat atatatttat tagacaagaa aagcagatta aatagatata cattcgatta    3120
acgataagta aaatgtaaaa tcacaggatt ttcgtgtgtg gtcttctaca cagacaagat    3180
gaaacaattc ggcattaata cctgagagca ggaagagcaa gataaaggt agtatttgtt    3240 ggcgatcccc ctagagtctt ttacatcttc ggaaaacaaa aactatttt tcttaatt      3300 cttttttac tttctatttt taatttatat atttatatta aaaatttaa attataatta     3360 ttttatagc acgtgatgaa aaggacccag gtggcactt tcggggaaat gtgcgcggaa    3420
cccctatttg tttattttc taaatacatt caaatatgta tccgctcatg agacaataac    3480
cctgataaat gcttcaataa tattgaaaaa ggaagagtat gagtattcaa catttccgtg    3540
tcgcccttat tccctttt gcggcatttt gccttcctgt ttttgctcac ccagaaacgc     3600
tggtgaaagt aaaagatgct gaagatcagt tgggtgcacg agtgggttac atcgaactgg    3660
atctcaacag cggtaagatc cttgagagtt ttcgccccga agaacgtttt ccaatgatga    3720
gcacttttaa agttctgcta tgtggcgcgg tattatcccg tgttgacgcc gggcaagagc    3780
aactcggtcg ccgcatacac tattctcaga atgacttggt tgagtactca ccagtcacag    3840
aaaagcatct tacggatggc atgacagtaa gagaattatg cagtgctgcc ataaccatga    3900
gtgataacac tgcggccaac ttacttctga caacgatcgg aggaccgaag gagctaaccg    3960
cttttttgca caacatgggg gatcatgtaa ctcgccttga tcgttgggaa ccggagctga    4020
atgaagccat accaaacgac gagcgtgaca ccacgatgcc tgtagcaatg gcaacaacgt    4080
tgcgcaaact attaactggc gaactactta ctctagcttc ccggcaacaa ttaatagact    4140
ggatggaggc ggataaagtt gcaggaccac ttctgcgctc ggcccttccg gctggctggt    4200
ttattgctga taaatctgga gccggtgagc gtgggtctcg cggtatcatt gcagcactgg    4260
ggccagatgg taagccctcc cgtatcgtag ttatctacac gacgggcagt caggcaacta    4320
tggatgaacg aaatagacag atcgctgaga taggtgcctc actgattaag cattggtaac    4380
tgtcagacca agtttactca tatatacttt agattgattt aaaacttcat ttttaattta    4440
aaaggatcta ggtgaagatc cttttttgata atctcatgac caaaatccct taacgtgagt    4500
tttcgttcca ctgagcgtca gaccccgtag aaaagatcaa aggatcttct tgagatcctt    4560
tttttctgcg cgtaatctgc tgcttgcaaa caaaaaaacc accgctacca gcggtggttt    4620
gtttgccgga tcaagagcta ccaactcttt ttccgaaggt aactggcttc agcagagcgc    4680
agataccaaa tactgtcctt ctagtgtagc cgtagttagg ccaccacttc aagaactctg    4740
tagcaccgcc tacatacctc gctctgctaa tcctgttacc agtggctgct gccagtggcg    4800
ataagtcgtg tcttaccggg ttggactcaa gacgatagtt accggataag gcgcagcggt    4860
cgggctgaac ggggggttcg tgcacacagc ccagcttgga gcgaacgacc tacaccgaac    4920
tgagatacct acagcgtgag cattgagaaa gcgccacgct tcccgaaggg agaaaggcgg    4980
```

-continued

```
acaggtatcc ggtaagcggc agggtcggaa caggagagcg cacgagggag cttccagggg    5040
ggaacgcctg gtatctttat agtcctgtcg ggtttcgcca cctctgactt gagcgtcgat    5100
ttttgtgatg ctcgtcaggg gggccgagcc tatggaaaaa cgccagcaac gcggccttt    5160 tacggttcct ggccttttgc tggccttttg ctcacatgtt ctttcctgcg ttatcccctg    5220
attctgtgga taaccgtatt accgcctttg agtgagctga taccgctcgc cgcagccgaa    5280
cgaccgagcg cagcgagtca gtgagcgagg aagcggaaga cgcccaata cgcaaaccgc     5340 ctctccccgc gcgttggccg attcattaat gcagctggca cgacaggttt cccgactgga    5400
aagcgggcag tgagcgcaac gcaattaatg tgagttacct cactcattag gcaccccagg    5460
ctttacactt tatgcttccg gctcctatgt tgtgtggaat tgtgagcgga taacaatttc    5520
acacaggaaa cagctatgac catgattacg ccaagctcgg aattaaccct cactaaaggg    5580
aacaaaagct ggctagt                                                   5597
```

<210> SEQ ID NO 57
<211> LENGTH: 13
<212> TYPE: PRT
<213> ORGANISM: Artificial Sequence
<220> FEATURE:
<223> OTHER INFORMATION: U6-HC7 hinge

<400> SEQUENCE: 57

Glu Pro Lys Ser Cys Asp Cys His Cys Pro Pro Cys Pro
 1               5                  10

<210> SEQ ID NO 58
<211> LENGTH: 435
<212> TYPE: DNA
<213> ORGANISM: Artificial Sequence
<220> FEATURE:
<223> OTHER INFORMATION: polynucleotide encoding CDR-L3 derived from
      L3-1 clone

<400> SEQUENCE: 58

```
gaattcacta gtgattaatt cgccgccacc atggattcac aggcccaggt cctcatgttg    60
ctgctgctat cggtatctgg tacctgtgga gatatccaga tgacccagtc cccgagctcc    120
ctgtccgcct ctgtgggcga tagggtcacc atcacctgca gtccagtca gagtctttta    180 gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg gacggattt cactctgacc atcagcagtc tgcagccgga agacttcgca    360
acttattact gtcagcagtc ctacagccgc ccgtacacgt tcggacaggg taccaaggtg    420
gagatcaaac gtacg                                                     435
```

<210> SEQ ID NO 59
<211> LENGTH: 435
<212> TYPE: DNA
<213> ORGANISM: Artificial Sequence
<220> FEATURE:
<223> OTHER INFORMATION: polynucleotide encoding CDR-L3 derived from
      L3-2 clone

<400> SEQUENCE: 59

```
gaattcacta gtgattaatt cgccgccacc atggattcac aggcccaggt cctcatgttg    60
ctgctgctat cggtatctgg tacctgtgga gatatccaga tgacccagtc cccgagctcc    120
ctgtccgcct ctgtgggcga tagggtcacc atcacctgca gtccagtca gagtctttta    180
```

```
gctagtggca accaaaataa ctacttggcc tggcaccaac agaaaccagg aaaagctccg      240
aaaatgctga ttatttgggc atccactagg gtatctggag tcccttctcg cttctctgga      300
tccgggtctg ggacggattt cactctgacc atcagcagtc tgcagccgga agacttcgca      360
acttattact gtgggcagtc ctacagccgt ccgctcacgt tcggacaggg taccaaggtg      420
gagatcaaac gtacg                                                       435

<210> SEQ ID NO 60
<211> LENGTH: 435
<212> TYPE: DNA
<213> ORGANISM: Artificial Sequence
<220> FEATURE:
<223> OTHER INFORMATION: polynucleotide encoding CDR-L3 derived from
      L3-3 clone

<400> SEQUENCE: 60
gaattcacta gtgattaatt cgccgccacc atggattcac aggcccaggt cctcatgttg       60
ctgctgctat cggtatctgg tacctgtgga gatatccaga tgacccagtc cccgagctcc      120
ctgtccgcct ctgtgggcga tagggtcacc atcacctgca gtccagtca gagtcttta       180 gctagtggca accaaaataa ctacttggcc tggcaccaac agaaaccagg aaaagctccg      240
aaaatgctga ttatttgggc atccactagg gtatctggag tcccttctcg cttctctgga      300
tccgggtctg ggacggattt cactctgacc atcagcagtc tgcagccgga agacttcgca      360
acttattact gtgcacagtc ctacagccat ccgttctctt tcggacaggg taccaaggtg      420
gagatcaaac gtacg                                                       435

<210> SEQ ID NO 61
<211> LENGTH: 435
<212> TYPE: DNA
<213> ORGANISM: Artificial Sequence
<220> FEATURE:
<223> OTHER INFORMATION: polynucleotide encoding CDR-L3 derived from
      L3-5 clone

<400> SEQUENCE: 61
gaattcacta gtgattaatt cgccgccacc atggattcac aggcccaggt cctcatgttg       60
ctgctgctat cggtatctgg tacctgtgga gatatccaga tgacccagtc cccgagctcc      120
ctgtccgcct ctgtgggcga tagggtcacc atcacctgca gtccagtca gagtcttta       180 gctagtggca accaaaataa ctacttggcc tggcaccaac agaaaccagg aaaagctccg      240
aaaatgctga ttatttgggc atccactagg gtatctggag tcccttctcg cttctctgga      300
tccgggtctg ggacggattt cactctgacc atcagcagtc tgcagccgga agacttcgca      360
acttattact gtcagcagtc ctacagccgc ccgtttacgt tcggacaggg taccaaggtg      420
gagatcaaac gtacg                                                       435

<210> SEQ ID NO 62
<211> LENGTH: 462
<212> TYPE: PRT
<213> ORGANISM: Artificial Sequence
<220> FEATURE:
<223> OTHER INFORMATION: polypeptide consisting of heavy chain variable
      region of huAbF46-H4-A1,U6-HC7 hinge and constant
      region of human IgG1

<400> SEQUENCE: 62

Met Glu Trp Ser Trp Val Phe Leu Val Thr Leu Leu Asn Gly Ile Gln
 1               5                  10                  15
```

Cys Glu Val Gln Leu Val Glu Ser Gly Gly Leu Val Gln Pro Gly
            20                  25                  30

Gly Ser Leu Arg Leu Ser Cys Ala Ala Ser Gly Phe Thr Phe Thr Asp
            35                  40                  45

Tyr Tyr Met Ser Trp Val Arg Gln Ala Pro Gly Lys Gly Leu Glu Trp
50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
            85                  90                  95

Thr Leu Tyr Leu Gln Met Asn Ser Leu Arg Ala Glu Thr Ala Val
            100                 105                 110

Tyr Tyr Cys Ala Arg Asp Asn Trp Phe Ala Tyr Trp Gly Gln Gly Thr
            115                 120                 125

Leu Val Thr Val Ser Ser Ala Ser Thr Lys Gly Pro Ser Val Phe Pro
130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
            165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
            195                 200                 205

Ser Leu Gly Thr Gln Thr Tyr Ile Cys Asn Val Asn His Lys Pro Ser
            210                 215                 220

Asn Thr Lys Val Asp Lys Lys Val Glu Pro Lys Ser Cys Asp Cys His
225                 230                 235                 240

Cys Pro Pro Cys Pro Ala Pro Glu Leu Leu Gly Gly Pro Ser Val Phe
            245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
            290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
            325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
            355                 360                 365

Ser Arg Glu Glu Met Thr Lys Asn Gln Val Ser Leu Thr Cys Leu Val
            370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
            405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
    450                 455                 460

<210> SEQ ID NO 63
<211> LENGTH: 1410
<212> TYPE: DNA
<213> ORGANISM: Artificial Sequence
<220> FEATURE:
<223> OTHER INFORMATION: polynucleotide encoding polypeptide consisting
      of heavy chain variable region of huAbF46-H4-A1, U6-HC7
      hinge and constant region of human IgG1

<400> SEQUENCE: 63

```
gaattcgccg ccaccatgga atggagctgg gttttctcg taacactttt aaatggtatc      60
cagtgtgagg ttcagctggt ggagtctggc ggtggcctgg tgcagccagg gggctcactc    120
cgtttgtcct gtgcagcttc tggcttcacc ttcactgatt actacatgag ctgggtgcgt    180
caggccccgg gtaagggcct ggaatggttg gttttatta gaaacaaagc taatggttac    240
acaacagagt acagtgcatc tgtgaagggt cgtttcacta taagcagaga taattccaaa    300
aacacactgt acctgcagat gaacagcctg cgtgctgagg acactgccgt ctattattgt    360
gctagagata actggtttgc ttactggggc caagggactc tggtcaccgt ctcctcggct    420
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
agctgcgatt gccactgtcc tccatgtcca gcacctgaac tcctgggggg accgtcagtc    780
ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc ccatcgaga aaaccatctc caaagccaaa    1080
gggcagcccc gagaaccaca ggtgtacacc ctgcccccat cccgggagga gatgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta cagcaagctc accgtggaca agagcaggtg gcagcagggg   1320
aacgtcttct catgctccgt gatgcatgag gctctgcaca accactacac gcagaagagc   1380
ctctccctgt ctccgggtaa atgactcgag                                    1410
```

<210> SEQ ID NO 64
<211> LENGTH: 461
<212> TYPE: PRT
<213> ORGANISM: Artificial Sequence
<220> FEATURE:
<223> OTHER INFORMATION: polypeptide consisting of heavy chain variable
      region of huAbF46-H4-A1, human IgG2 hinge and
      constant region of human IgG1

<400> SEQUENCE: 64

Met Glu Trp Ser Trp Val Phe Leu Val Thr Leu Leu Asn Gly Ile Gln

```
  1               5                   10                  15
Cys Glu Val Gln Leu Val Glu Ser Gly Gly Gly Leu Val Gln Pro Gly
                 20                  25                  30

Gly Ser Leu Arg Leu Ser Cys Ala Ala Ser Gly Phe Thr Phe Thr Asp
                 35                  40                  45

Tyr Tyr Met Ser Trp Val Arg Gln Ala Pro Gly Lys Gly Leu Glu Trp
 50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
                 100                 105                 110

Tyr Tyr Cys Ala Arg Asp Asn Trp Phe Ala Tyr Trp Gly Gln Gly Thr
                 115                 120                 125

Leu Val Thr Val Ser Ser Ala Ser Thr Lys Gly Pro Ser Val Phe Pro
                 130                 135                 140

Leu Ala Pro Ser Ser Lys Ser Thr Ser Gly Gly Thr Ala Ala Leu Gly
145                  150                 155                 160

Cys Leu Val Lys Asp Tyr Phe Pro Glu Pro Val Thr Val Ser Trp Asn
                 165                 170                 175

Ser Gly Ala Leu Thr Ser Gly Val His Thr Phe Pro Ala Val Leu Gln
                 180                 185                 190

Ser Ser Gly Leu Tyr Ser Leu Ser Ser Val Val Thr Val Pro Ser Ser
                 195                 200                 205

Ser Leu Gly Thr Gln Thr Tyr Ile Cys Asn Val Asn His Lys Pro Ser
                 210                 215                 220

Asn Thr Lys Val Asp Lys Lys Val Glu Arg Lys Cys Cys Val Glu Cys
225                  230                 235                 240

Pro Pro Cys Pro Ala Pro Glu Leu Leu Gly Gly Pro Ser Val Phe Leu
                 245                 250                 255

Phe Pro Pro Lys Pro Lys Asp Thr Leu Met Ile Ser Arg Thr Pro Glu
                 260                 265                 270

Val Thr Cys Val Val Val Asp Val Ser His Glu Asp Pro Glu Val Lys
                 275                 280                 285

Phe Asn Trp Tyr Val Asp Gly Val Glu Val His Asn Ala Lys Thr Lys
                 290                 295                 300

Pro Arg Glu Glu Gln Tyr Asn Ser Thr Tyr Arg Val Val Ser Val Leu
305                  310                 315                 320

Thr Val Leu His Gln Asp Trp Leu Asn Gly Lys Glu Tyr Lys Cys Lys
                 325                 330                 335

Val Ser Asn Lys Ala Leu Pro Ala Pro Ile Glu Lys Thr Ile Ser Lys
                 340                 345                 350

Ala Lys Gly Gln Pro Arg Glu Pro Gln Val Tyr Thr Leu Pro Pro Ser
                 355                 360                 365

Arg Glu Glu Met Thr Lys Asn Gln Val Ser Leu Thr Cys Leu Val Lys
                 370                 375                 380

Gly Phe Tyr Pro Ser Asp Ile Ala Val Glu Trp Glu Ser Asn Gly Gln
385                  390                 395                 400

Pro Glu Asn Asn Tyr Lys Thr Thr Pro Pro Val Leu Asp Ser Asp Gly
                 405                 410                 415

Ser Phe Phe Leu Tyr Ser Lys Leu Thr Val Asp Lys Ser Arg Trp Gln
                 420                 425                 430
```

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460

<210> SEQ ID NO 65
<211> LENGTH: 1407
<212> TYPE: DNA
<213> ORGANISM: Artificial Sequence
<220> FEATURE:
<223> OTHER INFORMATION: polynucleotide encoding polypeptide consisting
      of heavy chain variable region of huAbF46-H4-A1, human
      IgG2 hinge and constant region of human IgG1

<400> SEQUENCE: 65

| | | | | |
|---|---|---|---|---|
| gaattcgccg | ccaccatgga | atggagctgg | gttttctcg | taacactttt aaatggtatc | 60 |
| cagtgtgagg | ttcagctggt | ggagtctggc | ggtggcctgg | tgcagccagg gggctcactc | 120 |
| cgtttgtcct | gtgcagcttc | tggcttcacc | ttcactgatt | actacatgag ctgggtgcgt | 180 |
| caggccccgg | gtaagggcct | ggaatggttg | ggttttatta | gaaacaaagc taatggttac | 240 |
| acaacagagt | acagtgcatc | tgtgaagggt | cgtttcacta | taagcagaga taattccaaa | 300 |
| aacacactgt | acctgcagat | gaacagcctg | cgtgctgagg | acactgccgt ctattattgt | 360 |
| gctagagata | actggtttgc | ttactggggc | caagggactc | tggtcaccgt ctcctcggct | 420 |
| agcaccaagg | gcccatcggt | cttccccctg | gcaccctcct | ccaagagcac ctctgggggc | 480 |
| acagcggccc | tgggctgcct | ggtcaaggac | tacttcccg | aaccggtgac ggtgtcgtgg | 540 |
| aactcaggcg | ccctgaccag | cggcgtgcac | accttcccgg | ctgtcctaca gtcctcagga | 600 |
| ctctactccc | tcagcagcgt | ggtgaccgtg | ccctccagca | gcttgggcac ccagacctac | 660 |
| atctgcaacg | tgaatcacaa | gcccagcaac | accaaggtgg | acaagaaagt tgagaggaag | 720 |
| tgctgtgtgg | agtgcccccc | ctgcccagca | cctgaactcc | tggggggacc gtcagtcttc | 780 |
| ctcttccccc | caaaacccaa | ggacaccctc | atgatctccc | ggaccctga ggtcacatgc | 840 |
| gtggtggtgg | acgtgagcca | cgaagaccct | gaggtcaagt | tcaactggta cgtggacggc | 900 |
| gtggaggtgc | ataatgccaa | gacaaagccg | cgggaggagc | agtacaacag cacgtaccgt | 960 |
| gtggtcagcg | tcctcaccgt | cctgcaccag | gactggctga | atggcaagga gtacaagtgc | 1020 |
| aaggtctcca | acaaagccct | cccagccccc | atcgagaaaa | ccatctccaa agccaaaggg | 1080 |
| cagccccgag | aaccacaggt | gtacaccctg | cccccatccc | gggaggagat gaccaagaac | 1140 |
| caggtcagcc | tgacctgcct | ggtcaaaggc | ttctatccca | gcgacatcgc cgtggagtgg | 1200 |
| gagagcaatg | ggcagccgga | gaacaactac | aagaccacgc | ctcccgtgct ggactccgac | 1260 |
| ggctccttct | tcctctacag | caagctcacc | gtggacaaga | gcaggtggca gcaggggaac | 1320 |
| gtcttctcat | gctccgtgat | gcatgaggct | ctgcacaacc | actacacgca gaagagcctc | 1380 |
| tccctgtctc | cgggtaaatg | actcgag | | | 1407 |

<210> SEQ ID NO 66
<211> LENGTH: 460
<212> TYPE: PRT
<213> ORGANISM: Artificial Sequence
<220> FEATURE:
<223> OTHER INFORMATION: polypeptide consisting of heavy chain variable
      region of huAbF46-H4-A1, human IgG2 hinge and constant
      region of human IgG2

<400> SEQUENCE: 66

-continued

```
Met Glu Trp Ser Trp Val Phe Leu Val Thr Leu Leu Asn Gly Ile Gln
 1               5                  10                  15

Cys Glu Val Gln Leu Val Glu Ser Gly Gly Gly Leu Val Gln Pro Gly
             20                  25                  30

Gly Ser Leu Arg Leu Ser Cys Ala Ala Ser Gly Phe Thr Phe Thr Asp
         35                  40                  45

Tyr Tyr Met Ser Trp Val Arg Gln Ala Pro Gly Lys Gly Leu Glu Trp
     50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
             100                 105                 110

Tyr Tyr Cys Ala Arg Asp Asn Trp Phe Ala Tyr Trp Gly Gln Gly Thr
         115                 120                 125

Leu Val Thr Val Ser Ser Ala Ser Thr Lys Gly Pro Ser Val Phe Pro
     130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                 165                 170                 175

Ser Gly Ala Leu Thr Ser Gly Val His Thr Phe Pro Ala Val Leu Gln
             180                 185                 190

Ser Ser Gly Leu Tyr Ser Leu Ser Ser Val Val Thr Val Pro Ser Ser
         195                 200                 205

Asn Phe Gly Thr Gln Thr Tyr Thr Cys Asn Val Asp His Lys Pro Ser
     210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
                 245                 250                 255

Pro Pro Lys Pro Lys Asp Thr Leu Met Ile Ser Arg Thr Pro Glu Val
             260                 265                 270

Thr Cys Val Val Val Asp Val Ser His Glu Asp Pro Glu Val Gln Phe
         275                 280                 285

Asn Trp Tyr Val Asp Gly Val Glu Val His Asn Ala Lys Thr Lys Pro
     290                 295                 300

Arg Glu Glu Gln Phe Asn Ser Thr Phe Arg Val Val Ser Val Leu Thr
305                 310                 315                 320

Val Val His Gln Asp Trp Leu Asn Gly Lys Glu Tyr Lys Cys Lys Val
                 325                 330                 335

Ser Asn Lys Gly Leu Pro Ala Pro Ile Glu Lys Thr Ile Ser Lys Thr
             340                 345                 350

Lys Gly Gln Pro Arg Glu Pro Gln Val Tyr Thr Leu Pro Pro Ser Arg
         355                 360                 365

Glu Glu Met Thr Lys Asn Gln Val Ser Leu Thr Cys Leu Val Lys Gly
     370                 375                 380

Phe Tyr Pro Ser Asp Ile Ala Val Glu Trp Ser Asn Gly Gln Pro
385                 390                 395                 400

Glu Asn Asn Tyr Lys Thr Thr Pro Pro Met Leu Asp Ser Asp Gly Ser
                 405                 410                 415

Phe Phe Leu Tyr Ser Lys Leu Thr Val Asp Lys Ser Arg Trp Gln Gln
```

```
                420           425           430
Gly Asn Val Phe Ser Cys Ser Val Met His Glu Ala Leu His Asn His
            435               440                   445

Tyr Thr Gln Lys Ser Leu Ser Leu Ser Pro Gly Lys
    450               455               460
```

<210> SEQ ID NO 67
<211> LENGTH: 1404
<212> TYPE: DNA
<213> ORGANISM: Artificial Sequence
<220> FEATURE:
<223> OTHER INFORMATION: polynucleotide encoding polypeptide consisting
      of heavy chain variable region of huAbF46-H4-A1, human
      IgG2 hinge and constant region of human IgG2

<400> SEQUENCE: 67

```
gaattcgccg ccaccatgga atggagctgg gttttttctcg taacactttt aaatggtatc    60
cagtgtgagg ttcagctggt ggagtctggc ggtggcctgg tgcagccagg gggctcactc   120
cgtttgtcct gtgcagcttc tggcttcacc ttcactgatt actacatgag ctgggtgcgt   180
caggccccgg gtaagggcct ggaatggttg ggttttatta gaaacaaagc taatggttac   240
acaacagagt acagtgcatc tgtgaagggt cgtttcacta agcagagata attccaaa    300
aacacactgt acctgcagat gaacagcctg cgtgctgagg acactgccgt ctattattgt   360
gctagagata actggtttgc ttactggggc aagggactc tggtcaccgt ctcctcggct    420
agcaccaagg gcccatcggt cttccccctg gcgccctgct ccaggagcac ctccgagagc   480
acagcggccc tgggctgcct ggtcaaggac tacttccccg aaccggtgac ggtgtcgtgg   540
aactcaggcg ctctgaccag cggcgtgcac accttcccag ctgtcctaca gtcctcagga   600
ctctactccc tcagcagcgt ggtgaccgtg ccctccagca cttcggcac ccagacctac    660
acctgcaacg tagatcacaa gcccagcaac accaaggtgg acaagacagt tgagcgcaaa   720
tgttgtgtcg agtgcccacc gtgcccagca ccacctgtgg caggaccgtc agtcttcctc   780
ttccccccaa aacccaagga caccctcatg atctcccgga cccctgaggt cacgtgcgtg   840
gtggtggacg tgagccacga agaccccgag gtccagttca actggtacgt ggacggcgtg   900
gaggtgcata atgccaagac aaagccacgg gaggagcagt tcaacagcac gttccgtgtg   960
gtcagcgtcc tcaccgttgt gcaccaggac tggctgaacg gcaaggagta caagtgcaag  1020
gtctccaaca aaggcctccc agcccccatc gagaaaacca tctccaaaac caaagggcag  1080
ccccgagaac acaggtgtga cccctgccc ccatcccggg aggagatgac caagaaccag  1140
gtcagcctga cctgcctggt caaaggcttc taccccagcg acatcgccgt ggagtgggag  1200
agcaatgggc agccggagaa caactacaag accacgcctc ccatgctgga ctccgacggc  1260
tccttcttcc tctacagcaa gctcaccgtg gacaagagca ggtggcagca ggggaacgtc  1320
ttctcatgct ccgtgatgca tgaggctctg cacaaccact acacgcagaa gagcctctcc  1380
ctgtctccgg gtaaatgact cgag                                          1404
```

<210> SEQ ID NO 68
<211> LENGTH: 240
<212> TYPE: PRT
<213> ORGANISM: Artificial Sequence
<220> FEATURE:
<223> OTHER INFORMATION: polypeptide consisting of light chain variable
      region of huAbF46-H4-A1(H36Y) and human kappa
      constant region

<400> SEQUENCE: 68

```
Met Asp Ser Gln Ala Gln Val Leu Met Leu Leu Leu Ser Val Ser
 1               5                  10                  15

Gly Thr Cys Gly Asp Ile Gln Met Thr Gln Ser Pro Ser Ser Leu Ser
                 20                  25                  30

Ala Ser Val Gly Asp Arg Val Thr Ile Thr Cys Lys Ser Ser Gln Ser
            35                  40                  45

Leu Leu Ala Ser Gly Asn Gln Asn Asn Tyr Leu Ala Trp Tyr Gln Gln
        50                  55                  60

Lys Pro Gly Lys Ala Pro Lys Met Leu Ile Ile Trp Ala Ser Thr Arg
 65                  70                  75                  80

Val Ser Gly Val Pro Ser Arg Phe Ser Gly Ser Gly Ser Gly Thr Asp
                 85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 69
<211> LENGTH: 758
<212> TYPE: DNA
<213> ORGANISM: Artificial Sequence
<220> FEATURE:
<223> OTHER INFORMATION: polynucleotide encoding polypeptide consisting of light chain variable region of huAbF46-H4-A1(H36Y) and human kappa constant region

<400> SEQUENCE: 69

```
aattcactag tgattaattc gccgccacca tggattcaca ggcccaggtc ctcatgttgc     60
tgctgctatc ggtatctggt acctgtggag atatccagat gacccagtcc ccgagctccc    120
tgtccgcctc tgtgggcgat agggtcacca tcacctgcaa gtccagtcag agtcttttag    180
ctagtggcaa ccaaaataac tacttggcct ggtaccaaca gaaaccagga aaagctccga    240
aaatgctgat tatttgggca tccactaggg tatctggagt cccttctcgc ttctctggat    300
ccgggtctgg gacggatttc actctgacca tcagcagtct gcagccggaa gacttcgcaa    360
cttattactg tcagcagtcc tacagccgcc cgtacacgtt cggacagggt accaaggtgg    420
agatcaaacg tacggtggct gcaccatctg tcttcatctt cccgccatct gatgagcagt    480
tgaaatctgg aactgcctct gttgtgtgcc tgctgaataa cttctatccc agagaggcca    540
aagtacagtg gaaggtggat aacgcccctcc aatcgggtaa ctcccaggag agtgtcacag    600
agcaggacag caaggacagc acctacagcc tcagcagcac cctgacgctg agcaaagcag    660
```

```
actacgagaa acacaaagtc tacgcctgcg aagtcaccca tcagggcctg agctcgcccg    720
tcacaaagag cttcaacagg ggagagtgtt gactcgag                            758
```

<210> SEQ ID NO 70
<211> LENGTH: 240
<212> TYPE: PRT
<213> ORGANISM: Artificial Sequence
<220> FEATURE:
<223> OTHER INFORMATION: polypeptide consisting of light chain variable
      region of huAbF46-H4-A1 and human kappa constant
      region

<400> SEQUENCE: 70

```
Met Asp Ser Gln Ala Gln Val Leu Met Leu Leu Leu Leu Ser Val Ser
 1               5                  10                  15

Gly Thr Cys Gly Asp Ile Gln Met Thr Gln Ser Pro Ser Ser Leu Ser
             20                  25                  30

Ala Ser Val Gly Asp Arg Val Thr Ile Thr Cys Lys Ser Ser Gln Ser
         35                  40                  45

Leu Leu Ala Ser Gly Asn Gln Asn Asn Tyr Leu Ala Trp His Gln Gln
     50                  55                  60

Lys Pro Gly Lys Ala Pro Lys Met Leu Ile Ile Trp Ala Ser Thr Arg
 65                  70                  75                  80

Val Ser Gly Val Pro Ser Arg Phe Ser Gly Ser Gly Ser Gly Thr Asp
                 85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 71
<211> LENGTH: 19
<212> TYPE: PRT
<213> ORGANISM: Artificial Sequence
<220> FEATURE:
<223> OTHER INFORMATION: epitope in SEMA domain of c-Met

<400> SEQUENCE: 71

```
Phe Ser Pro Gln Ile Glu Glu Pro Ser Gln Cys Pro Asp Cys Val Val
 1               5                  10                  15

Ser Ala Leu
```

<210> SEQ ID NO 72

```
<211> LENGTH: 10
<212> TYPE: PRT
<213> ORGANISM: Artificial Sequence
<220> FEATURE:
<223> OTHER INFORMATION: epitope in SEMA domain of c-Met

<400> SEQUENCE: 72

Pro Gln Ile Glu Glu Pro Ser Gln Cys Pro
 1               5                  10

<210> SEQ ID NO 73
<211> LENGTH: 5
<212> TYPE: PRT
<213> ORGANISM: Artificial Sequence
<220> FEATURE:
<223> OTHER INFORMATION: epitope in SEMA domain of c-Met

<400> SEQUENCE: 73

Glu Glu Pro Ser Gln
 1               5

<210> SEQ ID NO 74
<211> LENGTH: 117
<212> TYPE: PRT
<213> ORGANISM: Artificial Sequence
<220> FEATURE:
<223> OTHER INFORMATION: heavy chain variable region of anti-c-Met
      antibody(AbF46 or huAbF46-H1)

<400> SEQUENCE: 74

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 75
<211> LENGTH: 114
<212> TYPE: PRT
<213> ORGANISM: Artificial Sequence
<220> FEATURE:
<223> OTHER INFORMATION: light chain variable region of anti-c-Met
      antibody(AbF46 or huAbF46-H1)

<400> SEQUENCE: 75

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45
```

```
Pro Pro Lys Met Leu Ile Ile Trp Ala Ser Thr Arg Val Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg

<210> SEQ ID NO 76
<211> LENGTH: 1416
<212> TYPE: DNA
<213> ORGANISM: Artificial Sequence
<220> FEATURE:
<223> OTHER INFORMATION: nucleotide sequence of heavy chain of
      nti-c-Met antibody (AbF46 or huAbF46-H1)
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop sodon
<220> FEATURE:
<221> NAME/KEY: misc_feature
<222> LOCATION: (1411)..(1416)
<223> OTHER INFORMATION: XhoI restriction site

<400> SEQUENCE: 76
gaattcgccg ccaccatgga atggagctgg gttttctcg taacactttt aaatggtatc      60
cagtgtgagg tgaagctggt ggagtctgga ggaggcttgg tacagcctgg gggttctctg    120
agactctcct gtgcaacttc tgggttcacc ttcactgatt actacatgag ctgggtccgc    180
cagcctccag gaaaggcact tgagtggttg ggttttatta gaaacaaagc taatggttac    240
acaacagagt acagtgcatc tgtgaagggt cggttcacca tctccagaga taattcccaa    300
agcatcctct atcttcaaat ggacaccctg agagctgagg acagtgccac ttattactgt    360
gcaagagata actggtttgc ttactggggc caagggactc tggtcactgt ctctgcagct    420
agcaccaagg gcccatcggt cttccccctg gcaccctcct ccaagagcac ctctgggggc    480
acagcggccc tgggctgcct ggtcaaggac tacttcccg aaccggtgac ggtgtcgtgg     540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
tcttgtgaca aaactcacac atgcccaccg tgcccagcac ctgaactcct ggggggaccg    780
```

```
tcagtcttcc tcttcccccc aaaacccaag dcaccctca tgatctcccg dccccctgag    840
gtcacatgcg tggtggtgga cgtgagccac gaagaccctg aggtcaagtt caactggtac    900
gtggacggcg tggaggtgca taatgccaag acaaagccgc gggaggagca gtacaacagc    960
acgtaccgtg tggtcagcgt cctcaccgtc ctgcaccagg actggctgaa tggcaaggag   1020
tacaagtgca aggtctccaa caaagccctc ccagccccca tcgagaaaac catctccaaa   1080
gccaaagggc agccccgaga accacaggtg tacaccctgc ccccatcccg ggaggagatg   1140
accaagaacc aggtcagcct gacctgcctg gtcaaaggct tctatcccag cgacatcgcc   1200
gtggagtggg agagcaatgg gcagccggag aacaactaca agaccacgcc tcccgtgctg   1260
gactccgacg gctccttctt cctctacagc aagctcaccg tggacaagag caggtggcag   1320
caggggaacg tcttctcatg ctccgtgatg catgaggctc tgcacaacca ctacacgcag   1380
aagagcctct ccctgtctcc gggtaaatga ctcgag                             1416
```

<210> SEQ ID NO 77
<211> LENGTH: 759
<212> TYPE: DNA
<213> ORGANISM: Artificial Sequence
<220> FEATURE:
<223> OTHER INFORMATION: nucleotide sequence of light chain of
      anti-c-Met antibody(AbF46 or huAbF46-H1)
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 77

```
gaattcacta gtgattaatt cgccgccacc atgattcac aggcccaggt cctcatgttg     60
ctgctgctat cggtatctgg tacctgtgga gacattttga tgacccagtc tccatcctcc    120
ctgactgtgt cagcaggaga gaaggtcact atgagctgca gtccagtca gagtctttta    180 gctagtggca accaaaataa ctacttggcc tggcaccagc agaaaccagg acgatctcct    240
aaaatgctga taaatttggggc atccactagg gtatctggag tccctgatcg cttcataggc    300
agtggatctg ggacggattt cactctgacc atcaacagtg tgcaggctga agatctggct    360
gtttattact gtcagcagtc ctacagcgct ccgctcacgt tcggtgctgg gaccaagctg    420
gagctgaaac gtacggtggc tgcaccatct gtcttcatct tcccgccatc tgatgagcag    480
ttgaaatctg gaactgcctc tgttgtgtgc ctgctgaata acttctatcc cagagaggcc    540
```

```
aaagtacagt ggaaggtgga taacgccctc caatcgggta actcccagga gagtgtcaca    600
gagcaggaca gcaaggacag cacctacagc ctcagcagca ccctgacgct gagcaaagca    660
gactacgaga acacaaagt  ctacgcctgc gaagtcaccc atcagggcct gagctcgccc    720
gtcacaaaga gcttcaacag gggagagtgt tgactcgag                           759

<210> SEQ ID NO 78
<211> LENGTH: 4170
<212> TYPE: DNA
<213> ORGANISM: Artificial Sequence
<220> FEATURE:
<223> OTHER INFORMATION: polynucleotide encoding c-Met protein

<400> SEQUENCE: 78
atgaaggccc ccgctgtgct tgcacctggc atcctcgtgc tcctgtttac cttggtgcag     60
aggagcaatg gggagtgtaa agaggcacta gcaaagtccg agatgaatgt gaatatgaag    120
tatcagcttc ccaacttcac cgcggaaaca cccatccaga atgtcattct acatgagcat    180
cacatttttc ttggtgccac taactacatt tatgttttaa atgaggaaga ccttcagaag    240
gttgctgagt acaagactgg gcctgtgctg gaacacccag attgtttccc atgtcaggac    300
tgcagcagca agccaatttt atcaggaggt gtttggaaag ataacatcaa catggctcta    360
gttgtcgaca cctactatga tgatcaactc attagctgtg gcagcgtcaa cagagggacc    420
tgccagcgac atgtctttcc ccacaatcat actgctgaca tacagtcgga ggttcactgc    480
atattctccc cacagataga agagcccagc cagtgtcctg actgtgtggt gagcgccctg    540
ggagccaaag tccttcatc tgtaaaggac cggttcatca acttctttgt aggcaatacc    600
ataaattctt cttattccc agatcatcca ttgcattcga tatcagtgag aaggctaaag    660
gaaacgaaag atggttttat gttttgacg gaccagtcct acattgatgt tttacctgag    720
ttcagagatt cttaccccat taagtatgtc catgcctttg aaagcaacaa ttttatttac    780
ttcttgacgg tccaaaggga aactctagat gctcagactt tcacacaag  aataatcagg    840 ttctgttcca taaactctgg attgcattcc tacatggaaa tgcctctgga gtgtattctc    900
acagaaaaga gaaaaagag  atccacaaag aaggaagtgt ttaatatact tcaggctgcg    960
tatgtcagca agcctggggc ccagcttgct agacaaatag gagccagcct gaatgatgac   1020
attcttttcg gggtgttcgc acaaagcaag ccagattctg ccgaaccaat ggatcgatct   1080
gccatgtgtg cattccctat caaatatgtc aacgacttct caacaagat  cgtcaacaaa   1140 aacaatgtga atgtctcca  gcatttttac ggacccaatc atgagcactg ctttaatagg   1200
acacttctga gaaattcatc aggctgtgaa gcgcgccgtg atgaatatcg aacagagttt   1260
accacagctt tgcagcgcgt tgacttattc atgggtcaat tcagcgaagt cctcttaaca   1320
tctatatcca ccttcattaa aggagacctc accatagcta atcttgggac atcagagggt   1380
cgcttcatgc aggttgtggt ttctcgatca ggaccatcaa cccctcatgt gaatttcctc   1440
ctggactccc atccagtgtc tccagaagtg attgtggagc atacattaaa ccaaaatggc   1500
tacacactgg ttatcactgg gaagaagatc acgaagatcc cattgaatgg cttgggctgc   1560
agacatttcc agtcctgcag tcaatgcctc tctgccccac cctttgttca gtgtggctgg   1620
tgccacgaca atgtgtgcg  atcggaggaa tgcctgagcg ggacatggac tcaacagatc   1680
tgtctgcctg caatctacaa ggttttccca aatagtgcac ccttgaagg  agggacaagg   1740 ctgaccatat gtggctggga ctttggattt cggaggaata taaatttga  tttaaagaaa   1800 actagagttc tccttggaaa tgagagctgc accttgactt taagtgagag cacgatgaat   1860
```

```
acattgaaat gcacagttgg tcctgccatg aataagcatt tcaatatgtc cataattatt    1920
tcaaatggcc acgggacaac acaatacagt acattctcct atgtggatcc tgtaataaca    1980
agtatttcgc cgaaatacgg tcctatggct ggtggcactt tacttacttt aactggaaat    2040
tacctaaaca gtgggaattc tagacacatt tcaattggtg aaaaacatg tactttaaaa     2100 agtgtgtcaa acagtattct tgaatgttat accccagccc aaaccatttc aactgagttt    2160
gctgttaaat tgaaaattga cttagccaac cgagagacaa gcatcttcag ttaccgtgaa    2220
gatcccattg tctatgaaat tcatccaacc aaatctttta ttagtggtgg gagcacaata    2280
acaggtgttg ggaaaaacct gaattcagtt agtgtcccga gaatggtcat aaatgtgcat    2340
gaagcaggaa ggaactttac agtggcatgt caacatcgct ctaattcaga gataatctgt    2400
tgtaccactc cttccctgca acagctgaat ctgcaactcc ccctgaaaac caaagccttt    2460
ttcatgttag atgggatcct ttccaaatac tttgatctca tttatgtaca taatcctgtg    2520
tttaagcctt ttgaaaagcc agtgatgatc tcaatgggca atgaaaatgt actggaaatt    2580
aagggaaatg atattgaccc tgaagcagtt aaaggtgaag tgttaaaagt tggaaataag    2640
agctgtgaga atatacactt acattctgaa gccgttttat gcacggtccc caatgacctg    2700
ctgaaattga cagcgagct aaatatagag tggaagcaag caatttcttc aaccgtcctt     2760
ggaaaagtaa tagttcaacc agatcagaat ttcacaggat tgattgctgg tgttgtctca    2820
atatcaacag cactgttatt actacttggg ttttttcctgt ggctgaaaaa gagaaagcaa    2880
attaaagatc tgggcagtga attagttcgc tacgatgcaa gagtacacac tcctcatttg    2940
gataggcttg taagtgcccg aagtgtaagc ccaactacag aaatggtttc aaatgaatct    3000
gtagactacc gagctacttt tccagaagat cagtttccta attcatctca gaacggttca    3060
tgccgacaag tgcagtatcc tctgacagac atgtccccca tcctaactag tggggactct    3120
gatatatcca gtccattact gcaaaatact gtccacattg acctcagtgc tctaaatcca    3180
gagctggtcc aggcagtgca gcatgtagtg attgggccca gtagcctgat tgtgcatttc    3240
aatgaagtca taggaagagg gcatttggt tgtgtatatc atgggacttt gttgacaat      3300 gatggcaaga aaattcactg tgctgtgaaa tccttgaaca gaatcactga cataggagaa    3360
gtttcccaat ttctgaccga gggaatcatc atgaaagatt ttagtcatcc caatgtcctc    3420
tcgctcctgg gaatctgcct gcgaagtgaa gggtctccgc tggtggtcct accatacatg    3480
aaacatggag atcttcgaaa tttcattcga aatgagactc ataatccaac tgtaaaagat    3540
cttattggct ttggtcttca agtagccaaa ggcatgaaat atcttgcaag caaaagtttg    3600
gtccacagag acttggctgc aagaaactgt atgctggatg aaaaattcac agtcaaggtt    3660
gctgattttg gtcttgccag agacatgtat gataaagaat actatagtgt acacaacaaa    3720
acaggtgcaa agctgccagt gaagtggatg gctttggaaa gtctgcaaac tcaaaagttt    3780
accaccaagt cagatgtgtg gtccttggc gtgctcctct gggagctgat gacaagagga    3840
gccccacctt atcctgacgt aaacaccttt gatataactg tttacttgtt gcaagggaga    3900
agactcctac aacccgaata ctgcccagac ccttatatg aagtaatgct aaaatgctgg    3960
caccctaaag ccgaaatgcg cccatccttt tctgaactgg tgtcccggat atcagcgatc    4020
ttctctactt tcattgggga gcactatgtc catgtgaacg ctacttatgt gaacgtaaaa    4080
tgtgtcgctc cgtatccttc tctgttgtca tcagaagata acgctgatga tgaggtggac    4140
acacgaccag cctccttctg ggagacatca                                     4170
```

<210> SEQ ID NO 79
<211> LENGTH: 444
<212> TYPE: PRT
<213> ORGANISM: Artificial Sequence
<220> FEATURE:
<223> OTHER INFORMATION: SEMA domain of c-Met

<400> SEQUENCE: 79

```
Leu His Glu His His Ile Phe Leu Gly Ala Thr Asn Tyr Ile Tyr Val
 1               5                  10                  15

Leu Asn Glu Glu Asp Leu Gln Lys Val Ala Glu Tyr Lys Thr Gly Pro
                20                  25                  30

Val Leu Glu His Pro Asp Cys Phe Pro Cys Gln Asp Cys Ser Ser Lys
            35                  40                  45

Ala Asn Leu Ser Gly Gly Val Trp Lys Asp Asn Ile Asn Met Ala Leu
        50                  55                  60

Val Val Asp Thr Tyr Tyr Asp Asp Gln Leu Ile Ser Cys Gly Ser Val
65                  70                  75                  80

Asn Arg Gly Thr Cys Gln Arg His Val Phe Pro His Asn His Thr Ala
                85                  90                  95

Asp Ile Gln Ser Glu Val His Cys Ile Phe Ser Pro Gln Ile Glu Glu
            100                 105                 110

Pro Ser Gln Cys Pro Asp Cys Val Val Ser Ala Leu Gly Ala Lys Val
        115                 120                 125

Leu Ser Ser Val Lys Asp Arg Phe Ile Asn Phe Phe Val Gly Asn Thr
    130                 135                 140

Ile Asn Ser Ser Tyr Phe Pro Asp His Pro Leu His Ser Ile Ser Val
145                 150                 155                 160

Arg Arg Leu Lys Glu Thr Lys Asp Gly Phe Met Phe Leu Thr Asp Gln
                165                 170                 175

Ser Tyr Ile Asp Val Leu Pro Glu Phe Arg Asp Ser Tyr Pro Ile Lys
            180                 185                 190

Tyr Val His Ala Phe Glu Ser Asn Asn Phe Ile Tyr Phe Leu Thr Val
        195                 200                 205

Gln Arg Glu Thr Leu Asp Ala Gln Thr Phe His Thr Arg Ile Ile Arg
    210                 215                 220

Phe Cys Ser Ile Asn Ser Gly Leu His Ser Tyr Met Glu Met Pro Leu
225                 230                 235                 240

Glu Cys Ile Leu Thr Glu Lys Arg Lys Arg Ser Thr Lys Lys Glu
                245                 250                 255

Val Phe Asn Ile Leu Gln Ala Ala Tyr Val Ser Lys Pro Gly Ala Gln
            260                 265                 270

Leu Ala Arg Gln Ile Gly Ala Ser Leu Asn Asp Asp Ile Leu Phe Gly
        275                 280                 285

Val Phe Ala Gln Ser Lys Pro Asp Ser Ala Glu Pro Met Asp Arg Ser
    290                 295                 300

Ala Met Cys Ala Phe Pro Ile Lys Tyr Val Asn Asp Phe Phe Asn Lys
305                 310                 315                 320

Ile Val Asn Lys Asn Asn Val Arg Cys Leu Gln His Phe Tyr Gly Pro
                325                 330                 335

Asn His Glu His Cys Phe Asn Arg Thr Leu Leu Arg Asn Ser Ser Gly
            340                 345                 350

Cys Glu Ala Arg Arg Asp Glu Tyr Arg Thr Glu Phe Thr Thr Ala Leu
        355                 360                 365
```

```
Gln Arg Val Asp Leu Phe Met Gly Gln Phe Ser Glu Val Leu Leu Thr
    370                 375                 380

Ser Ile Ser Thr Phe Ile Lys Gly Asp Leu Thr Ile Ala Asn Leu Gly
385                 390                 395                 400

Thr Ser Glu Gly Arg Phe Met Gln Val Val Ser Arg Ser Gly Pro
                405                 410                 415

Ser Thr Pro His Val Asn Phe Leu Leu Asp Ser His Pro Val Ser Pro
            420                 425                 430

Glu Val Ile Val Glu His Thr Leu Asn Gln Asn Gly
            435                 440

<210> SEQ ID NO 80
<211> LENGTH: 451
<212> TYPE: PRT
<213> ORGANISM: Artificial Sequence
<220> FEATURE:
<223> OTHER INFORMATION: PSI-IPT domain of c-Met

<400> SEQUENCE: 80

Tyr Thr Leu Val Ile Thr Gly Lys Lys Ile Thr Lys Ile Pro Leu Asn
  1               5                  10                  15

Gly Leu Gly Cys Arg His Phe Gln Ser Cys Ser Gln Cys Leu Ser Ala
                20                  25                  30

Pro Pro Phe Val Gln Cys Gly Trp Cys His Asp Lys Cys Val Arg Ser
            35                  40                  45

Glu Glu Cys Leu Ser Gly Thr Trp Thr Gln Gln Ile Cys Leu Pro Ala
 50                  55                  60

Ile Tyr Lys Val Phe Pro Asn Ser Ala Pro Leu Glu Gly Gly Thr Arg
 65                  70                  75                  80

Leu Thr Ile Cys Gly Trp Asp Phe Gly Phe Arg Arg Asn Asn Lys Phe
                85                  90                  95

Asp Leu Lys Lys Thr Arg Val Leu Leu Gly Asn Glu Ser Cys Thr Leu
                100                 105                 110

Thr Leu Ser Glu Ser Thr Met Asn Thr Leu Lys Cys Thr Val Gly Pro
            115                 120                 125

Ala Met Asn Lys His Phe Asn Met Ser Ile Ile Ile Ser Asn Gly His
130                 135                 140

Gly Thr Thr Gln Tyr Ser Thr Phe Ser Tyr Val Asp Pro Val Ile Thr
145                 150                 155                 160

Ser Ile Ser Pro Lys Tyr Gly Pro Met Ala Gly Gly Thr Leu Leu Thr
                165                 170                 175

Leu Thr Gly Asn Tyr Leu Asn Ser Gly Asn Ser Arg His Ile Ser Ile
                180                 185                 190

Gly Gly Lys Thr Cys Thr Leu Lys Ser Val Ser Asn Ser Ile Leu Glu
            195                 200                 205

Cys Tyr Thr Pro Ala Gln Thr Ile Ser Thr Glu Phe Ala Val Lys Leu
210                 215                 220

Lys Ile Asp Leu Ala Asn Arg Glu Thr Ser Ile Phe Ser Tyr Arg Glu
225                 230                 235                 240

Asp Pro Ile Val Tyr Glu Ile His Pro Thr Lys Ser Phe Ile Ser Thr
                245                 250                 255

Trp Trp Lys Glu Pro Leu Asn Ile Val Ser Phe Leu Phe Cys Phe Ala
                260                 265                 270

Ser Gly Gly Ser Thr Ile Thr Gly Val Gly Lys Asn Leu Asn Ser Val
            275                 280                 285
```

```
Ser Val Pro Arg Met Val Ile Asn Val His Glu Ala Gly Arg Asn Phe
    290                 295                 300
Thr Val Ala Cys Gln His Arg Ser Asn Ser Glu Ile Ile Cys Cys Thr
305                 310                 315                 320
Thr Pro Ser Leu Gln Gln Leu Asn Leu Gln Leu Pro Leu Lys Thr Lys
                325                 330                 335
Ala Phe Phe Met Leu Asp Gly Ile Leu Ser Lys Tyr Phe Asp Leu Ile
                340                 345                 350
Tyr Val His Asn Pro Val Phe Lys Pro Phe Glu Lys Pro Val Met Ile
                355                 360                 365
Ser Met Gly Asn Glu Asn Val Leu Glu Ile Lys Gly Asn Asp Ile Asp
    370                 375                 380
Pro Glu Ala Val Lys Gly Glu Val Leu Lys Val Gly Asn Lys Ser Cys
385                 390                 395                 400
Glu Asn Ile His Leu His Ser Glu Ala Val Leu Cys Thr Val Pro Asn
                405                 410                 415
Asp Leu Leu Lys Leu Asn Ser Glu Leu Asn Ile Glu Trp Lys Gln Ala
                420                 425                 430
Ile Ser Ser Thr Val Leu Gly Lys Val Ile Val Gln Pro Asp Gln Asn
                435                 440                 445
Phe Thr Gly
    450

<210> SEQ ID NO 81
<211> LENGTH: 313
<212> TYPE: PRT
<213> ORGANISM: Artificial Sequence
<220> FEATURE:
<223> OTHER INFORMATION: TyrKc domain of c-Met

<400> SEQUENCE: 81

Val His Phe Asn Glu Val Ile Gly Arg Gly His Phe Gly Cys Val Tyr
  1               5                  10                  15
His Gly Thr Leu Leu Asp Asn Asp Gly Lys Lys Ile His Cys Ala Val
                 20                  25                  30
Lys Ser Leu Asn Arg Ile Thr Asp Ile Gly Glu Val Ser Gln Phe Leu
             35                  40                  45
Thr Glu Gly Ile Ile Met Lys Asp Phe Ser His Pro Asn Val Leu Ser
         50                  55                  60
Leu Leu Gly Ile Cys Leu Arg Ser Glu Gly Ser Pro Leu Val Val Leu
 65                  70                  75                  80
Pro Tyr Met Lys His Gly Asp Leu Arg Asn Phe Ile Arg Asn Glu Thr
                 85                  90                  95
His Asn Pro Thr Val Lys Asp Leu Ile Gly Phe Gly Leu Gln Val Ala
                100                 105                 110
Lys Gly Met Lys Tyr Leu Ala Ser Lys Lys Phe Val His Arg Asp Leu
            115                 120                 125
Ala Ala Arg Asn Cys Met Leu Asp Glu Lys Phe Thr Val Lys Val Ala
        130                 135                 140
Asp Phe Gly Leu Ala Arg Asp Met Tyr Asp Lys Glu Tyr Tyr Ser Val
145                 150                 155                 160
His Asn Lys Thr Gly Ala Lys Leu Pro Val Lys Trp Met Ala Leu Glu
                165                 170                 175
Ser Leu Gln Thr Gln Lys Phe Thr Lys Ser Asp Val Trp Ser Phe
                180                 185                 190
```

```
Gly Val Leu Leu Trp Glu Leu Met Thr Arg Gly Ala Pro Pro Tyr Pro
            195                 200                 205

Asp Val Asn Thr Phe Asp Ile Thr Val Tyr Leu Leu Gln Gly Arg Arg
    210                 215                 220

Leu Leu Gln Pro Glu Tyr Cys Pro Asp Pro Leu Tyr Glu Val Met Leu
225                 230                 235                 240

Lys Cys Trp His Pro Lys Ala Glu Met Arg Pro Ser Phe Ser Glu Leu
                245                 250                 255

Val Ser Arg Ile Ser Ala Ile Phe Ser Thr Phe Ile Gly Glu His Tyr
            260                 265                 270

Val His Val Asn Ala Thr Tyr Val Asn Val Lys Cys Val Ala Pro Tyr
        275                 280                 285

Pro Ser Leu Leu Ser Ser Glu Asp Asn Ala Asp Asp Glu Val Asp Thr
    290                 295                 300

Arg Pro Ala Ser Phe Trp Glu Thr Ser
305                 310

<210> SEQ ID NO 82
<211> LENGTH: 1332
<212> TYPE: DNA
<213> ORGANISM: Artificial Sequence
<220> FEATURE:
<223> OTHER INFORMATION: polynucleotide encoding SEMA domain of c-Met

<400> SEQUENCE: 82
ctacatgagc atcacatttt ccttggtgcc actaactaca tttatgtttt aaatgaggaa      60
gaccttcaga aggttgctga gtacaagact gggcctgtgc tggaacaccc agattgtttc     120
ccatgtcagg actgcagcag caaagccaat ttatcaggag gtgtttggaa agataacatc     180
aacatggctc tagttgtcga cacctactat gatgatcaac tcattagctg tggcagcgtc     240
aacagaggga cctgccagcg acatgtcttt ccccacaatc atactgctga catacagtcg     300
gaggttcact gcatattctc cccacagata gaagagccca gccagtgtcc tgactgtgtg     360
gtgagcgccc tgggagccaa agtccttttca tctgtaaagg accggttcat caacttcttt     420
gtaggcaata ccataaaatc ttcttatttc ccagatcatc cattgcattc gatatcagtg     480
agaaggctaa aggaaacgaa gatggtttt atgtttttga cggaccagtc ctacattgat     540
gttttacctg agtcagaga ttcttacccc attaagtatg tccatgcctt tgaaagcaac     600
aattttattt acttcttgac ggtccaaagg gaaactctag atgctcagac ttttcacaca     660
agaataatca ggttctgttc cataaactct ggattgcatt cctacatgga aatgcctctg     720
gagtgtattc tcacagaaaa gagaaaaaag agatccacaa agaggaagt gtttaatata     780 cttcaggctg cgtatgtcag caagcctggg gcccagcttg ctagacaaat aggagccagc     840
ctgaatgatg acattctttt cggggtgttc gcacaaagca gccagattc tgccgaacca     900 atggatcgat ctgccatgtg tgcattccct atcaaatatg tcaacgactt cttcaacaag     960
atcgtcaaca aaaacaatgt gagatgtctc cagcattttt acggacccaa tcatgagcac    1020
tgctttaata ggacacttct gagaaattca tcaggctgtg aagcgcgccg tgatgaatat    1080
cgaacagagt ttaccacagc tttgcagcgc gttgacttat tcatgggtca attcagcgaa    1140
gtcctcttaa catctatatc caccttcatt aaaggagacc tcaccatagc taatcttggg    1200
acatcagagg gtcgcttcat gcaggttgtg gtttctcgat caggaccatc aacccctcat    1260
gtgaattttc tcctggactc ccatccagtg tctccagaag tgattgtgga gcatacatta    1320
aaccaaaatg gc                                                        1332
```

<210> SEQ ID NO 83
<211> LENGTH: 1299
<212> TYPE: DNA
<213> ORGANISM: Artificial Sequence
<220> FEATURE:
<223> OTHER INFORMATION: polynucleotide encoding PSI-IPT domain of c-Met

<400> SEQUENCE: 83

```
tacacactgg ttatcactgg gaagaagatc acgaagatcc cattgaatgg cttgggctgc        60
agacatttcc agtcctgcag tcaatgcctc tctgccccac cctttgttca gtgtggctgg       120
tgccacgaca aatgtgtgcg atcggaggaa tgcctgagcg ggacatggac tcaacagatc       180
tgtctgcctg caatctacaa ggttttccca aatagtgcac cccttgaagg agggacaagg       240
ctgaccatat gtggctggga ctttggattt cggaggaata taaatttga tttaaagaaa        300
actagagttc tccttggaaa tgagagctgc accttgactt aagtgagag cacgatgaat        360
acattgaaat gcacagttgg tcctgccatg aataagcatt tcaatatgtc cataattatt       420
tcaaatggcc acgggacaac acaatacagt acattctcct atgtggatcc tgtaataaca       480
agtatttcgc cgaaatacgg tcctatggct ggtggcactt tacttacttt aactggaaat       540
tacctaaaca gtgggaattc tagacacatt tcaattggtg aaaaacatg tactttaaaa        600
agtgtgtcaa acagtattct tgaatgttat accccagccc aaaccatttc aactgagttt       660
gctgttaaat tgaaaattga cttagccaac cgagagacaa gcatcttcag ttaccgtgaa       720
gatcccattg tctatgaaat tcatccaacc aaatctttta ttagtggtgg agcacaata        780
acaggtgttg ggaaaaacct gaattcagtt agtgtcccga gaatggtcat aaatgtgcat       840
gaagcaggaa ggaactttac agtggcatgt caacatcgct ctaattcaga gataatctgt       900
tgtaccactc cttccctgca acagctgaat ctgcaactcc ccctgaaaac caaagccttt       960
ttcatgttag atgggatcct ttccaaatac tttgatctca tttatgtaca taatcctgtg      1020
tttaagcctt ttgaaaagcc agtgatgatc tcaatgggca atgaaaatgt actggaaatt      1080
aagggaaatg atattgaccc tgaagcagtt aaaggtgaag tgttaaaagt tggaaataag      1140
agctgtgaga atatacactt acattctgaa gccgttttat gcacggtccc caatgacctg      1200
ctgaaattga acagcgagct aaatatagag tggaagcaag caatttcttc aaccgtcctt      1260
ggaaaagtaa tagttcaacc agatcagaat ttcacagga                              1299
```

<210> SEQ ID NO 84
<211> LENGTH: 939
<212> TYPE: DNA
<213> ORGANISM: Artificial Sequence
<220> FEATURE:
<223> OTHER INFORMATION: polynucleotide encoding TyrKc domain of c-Met

<400> SEQUENCE: 84

```
gtgcatttca atgaagtcat aggaagaggg catttttggtt gtgtatatca tgggactttg        60
ttggacaatg atggcaagaa aattcactgt gctgtgaaat ccttgaacag atcactgac        120
ataggagaag tttcccaatt tctgaccgag ggaatcatca tgaaagattt tagtcatccc       180
aatgtcctct cgctcctggg aatctgcctg cgaagtgaag ggtctccgct ggtggtccta       240
ccatacatga aacatggaga tcttcgaaat ttcattcgaa atgagactca taatccaact       300
gtaaagatc ttattggctt tggtcttcaa gtagccaaag gcatgaaata tcttgcaagc       360
aaaaagtttg tccacagaga cttggctgca agaaactgta tgctggatga aaaattcaca       420
```

```
gtcaaggttg ctgattttgg tcttgccaga gacatgtatg ataaagaata ctatagtgta    480
cacaacaaaa caggtgcaaa gctgccagtg aagtggatgg ctttggaaag tctgcaaact    540
caaaagttta ccaccaagtc agatgtgtgg tcctttggcg tgctcctctg ggagctgatg    600
acaagaggag ccccacctta tcctgacgta aacacctttg atataactgt ttacttgttg    660
caagggagaa gactcctaca acccgaatac tgcccagacc ccttatatga agtaatgcta    720
aaatgctggc accctaaagc cgaaatcgcc ccatccttt ctgaactggt gtcccggata    780
tcagcgatct tctctacttt cattggggag cactatgtcc atgtgaacgc tacttatgtg    840
aacgtaaaat gtgtcgctcc gtatccttct ctgttgtcat cagaagataa cgctgatgat    900
gaggtggaca cacgaccagc ctccttctgg gagacatca                           939
```

<210> SEQ ID NO 85
<211> LENGTH: 13
<212> TYPE: PRT
<213> ORGANISM: Artificial Sequence
<220> FEATURE:
<223> OTHER INFORMATION: heavy chain CDR3 of anti-c-Met antibody

<400> SEQUENCE: 85

Asp Asn Trp Phe Ala Tyr Trp Gly Gln Gly Thr Leu Val
 1               5                  10

<210> SEQ ID NO 86
<211> LENGTH: 10
<212> TYPE: PRT
<213> ORGANISM: Artificial Sequence
<220> FEATURE:
<223> OTHER INFORMATION: light chain CDR3 of anti-c-Met antibody

<400> SEQUENCE: 86

Leu Thr Phe Gly Ala Gly Thr Lys Leu Glu
 1               5                  10

<210> SEQ ID NO 87
<211> LENGTH: 117
<212> TYPE: PRT
<213> ORGANISM: Artificial Sequence
<220> FEATURE:
<223> OTHER INFORMATION: heavy chain variable region of monoclonal
      antibody AbF46

<400> SEQUENCE: 87

Glu Val Lys Leu Val Glu Ser Gly Gly Gly Leu Val Gln Pro Gly Gly
 1               5                  10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asp Thr Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ala
        115

```
<210> SEQ ID NO 88
<211> LENGTH: 114
<212> TYPE: PRT
<213> ORGANISM: Artificial Sequence
<220> FEATURE:
<223> OTHER INFORMATION: light chain variable region of anti-c-Met
      antibody

<400> SEQUENCE: 88

Asp Ile Leu Met Thr Gln Ser Pro Ser Ser Leu Thr Val Ser Ala Gly
 1               5                  10                  15

Glu Lys Val Thr Met Ser Cys Lys Ser Gln Ser Leu Leu Ala Ser
                20                  25                  30

Gly Asn Gln Asn Asn Tyr Leu Ala Trp His Gln Gln Lys Pro Gly Arg
            35                  40                  45

Ser Pro Lys Met Leu Ile Ile Trp Ala Ser Thr Arg Val Ser Gly Val
        50                  55                  60

Pro Asp Arg Phe Ile Gly Ser Gly Ser Gly Thr Asp Phe Thr Leu Thr
 65                  70                  75                  80

Ile Asn Ser Val Gln Ala Glu Asp Leu Ala Val Tyr Tyr Cys Gln Gln
                85                  90                  95

Ser Tyr Ser Ala Pro Leu Thr Phe Gly Ala Gly Thr Lys Leu Glu Leu
            100                 105                 110

Lys Arg

<210> SEQ ID NO 89
<211> LENGTH: 17
<212> TYPE: PRT
<213> ORGANISM: Artificial Sequence
<220> FEATURE:
<223> OTHER INFORMATION: light chain CDR3 of anti-c-Met antibody

<400> SEQUENCE: 89

Gln Gln Ser Tyr Ser Ala Pro Leu Thr Phe Gly Ala Gly Thr Lys Leu
 1               5                  10                  15

Glu

<210> SEQ ID NO 90
<211> LENGTH: 117
<212> TYPE: PRT
<213> ORGANISM: Artificial Sequence
<220> FEATURE:
<223> OTHER INFORMATION: heavy chain variable region of AT-VH1

<400> SEQUENCE: 90

Glu Val Lys Leu Val Glu Ser Gly Gly Gly Leu Val Gln Pro Gly Gly
 1               5                  10                  15

Ser Leu Arg Leu Ser Cys Ala Thr Ser Gly Phe Thr Phe Thr Asp Tyr
                20                  25                  30

Tyr Met Ser Trp Val Arg Gln Pro Pro Gly Lys Gly Leu Glu Trp Leu
            35                  40                  45

Gly Phe Ile Arg Asn Lys Ala Asn Gly Tyr Thr Thr Glu Tyr Ser Ala
        50                  55                  60

Ser Val Lys Gly Arg Phe Thr Ile Ser Arg Asp Asn Ser Lys Ser Thr
 65                  70                  75                  80

Leu Tyr Leu Gln Met Asn Ser Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110
```

```
Val Thr Val Ser Ser
        115

<210> SEQ ID NO 91
<211> LENGTH: 117
<212> TYPE: PRT
<213> ORGANISM: Artificial Sequence
<220> FEATURE:
<223> OTHER INFORMATION: heavy chain variable region of AT-VH2

<400> SEQUENCE: 91

Glu Val Lys Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Tyr
             20                  25                  30

Tyr Met Ser Trp Val Arg Gln Pro Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Ser Thr
 65                  70                  75                  80

Leu Tyr Leu Gln Met Asn Ser Leu Arg Ala Glu Asp Thr Ala Thr Tyr
                 85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 92
<211> LENGTH: 117
<212> TYPE: PRT
<213> ORGANISM: Artificial Sequence
<220> FEATURE:
<223> OTHER INFORMATION: heavy chain variable region of AT-VH3

<400> SEQUENCE: 92

Glu Val Gln Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Tyr
             20                  25                  30

Tyr Met Ser Trp Val Arg Gln Pro Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Ser Thr
 65                  70                  75                  80

Leu Tyr Leu Gln Met Asn Ser Leu Arg Ala Glu Asp Thr Ala Thr Tyr
                 85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 93
<211> LENGTH: 117
<212> TYPE: PRT
<213> ORGANISM: Artificial Sequence
<220> FEATURE:
<223> OTHER INFORMATION: heavy chain variable region of AT-VH4
```

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Thr Tyr
            85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 94
<211> LENGTH: 117
<212> TYPE: PRT
<213> ORGANISM: Artificial Sequence
<220> FEATURE:
<223> OTHER INFORMATION: heavy chain variable region of AT-VH5

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
            85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 95
<211> LENGTH: 114
<212> TYPE: PRT
<213> ORGANISM: Artificial Sequence
<220> FEATURE:
<223> OTHER INFORMATION: light chain variable region of anti c-Met
      humanized antibody(huAbF46-H4)

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys

```
                35                  40                  45
Ala Pro Lys Met Leu Ile Ile Trp Ala Ser Thr Arg Val Ser Gly Val
         50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Ala Pro Leu Thr Phe Gly Gln Gly Thr Lys Val Glu Ile
            100                 105                 110

Lys Arg

<210> SEQ ID NO 96
<211> LENGTH: 113
<212> TYPE: PRT
<213> ORGANISM: Artificial Sequence
<220> FEATURE:
<223> OTHER INFORMATION: light chain variable region of AT-Vk1

<400> SEQUENCE: 96

Asp Ile Leu Met Thr Gln Ser Pro Ser Ser Leu Thr Ala Ser Val Gly
  1               5                  10                  15

Asp Arg Val Thr Met Thr Cys Lys Ser Ser Gln Ser Leu Leu Ala Ser
                 20                  25                  30

Gly Asn Gln Asn Asn Tyr Leu Ala Trp His Gln Lys Pro Gly Lys
             35                  40                  45

Ala Pro Lys Met Leu Ile Ile Trp Ala Ser Thr Arg Val Ser Gly Val
         50                  55                  60

Pro Asp Arg Phe Ile Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Ser Ala Pro Leu Thr Phe Gly Gln Gly Thr Lys Leu Glu Ile
            100                 105                 110

Lys

<210> SEQ ID NO 97
<211> LENGTH: 113
<212> TYPE: PRT
<213> ORGANISM: Artificial Sequence
<220> FEATURE:
<223> OTHER INFORMATION: light chain variable region of AT-Vk2

<400> SEQUENCE: 97

Asp Ile Leu Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Ser
                 20                  25                  30

Gly Asn Gln Asn Asn Tyr Leu Ala Trp His Gln Lys Pro Gly Lys
             35                  40                  45

Ala Pro Lys Met Leu Ile Ile Trp Ala Ser Thr Arg Val Ser Gly Val
         50                  55                  60

Pro Asp Arg Phe Ile Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Ser Ala Pro Leu Thr Phe Gly Gln Gly Thr Lys Leu Glu Ile
            100                 105                 110
```

Lys

<210> SEQ ID NO 98
<211> LENGTH: 113
<212> TYPE: PRT
<213> ORGANISM: Artificial Sequence
<220> FEATURE:
<223> OTHER INFORMATION: light chain variable region of AT-Vk3

<400> SEQUENCE: 98

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 99
<211> LENGTH: 113
<212> TYPE: PRT
<213> ORGANISM: Artificial Sequence
<220> FEATURE:
<223> OTHER INFORMATION: light chain variable region of AT-Vk4

<400> SEQUENCE: 99

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 100
<211> LENGTH: 13
<212> TYPE: PRT
<213> ORGANISM: Artificial Sequence
<220> FEATURE:
<223> OTHER INFORMATION: modified hinge region(U7-HC6)

<400> SEQUENCE: 100

Glu Pro Ser Cys Asp Lys His Cys Cys Pro Pro Cys Pro
1               5                   10

<210> SEQ ID NO 101
<211> LENGTH: 13
<212> TYPE: PRT
<213> ORGANISM: Artificial Sequence
<220> FEATURE:
<223> OTHER INFORMATION: modified hinge region(U6-HC7)

<400> SEQUENCE: 101

Glu Pro Lys Ser Cys Asp Cys His Cys Pro Pro Cys Pro
1               5                   10

<210> SEQ ID NO 102
<211> LENGTH: 12
<212> TYPE: PRT
<213> ORGANISM: Artificial Sequence
<220> FEATURE:
<223> OTHER INFORMATION: modified hinge region(U3-HC9)

<400> SEQUENCE: 102

Glu Arg Lys Cys Cys Val Glu Cys Pro Pro Cys Pro
1               5                   10

<210> SEQ ID NO 103
<211> LENGTH: 14
<212> TYPE: PRT
<213> ORGANISM: Artificial Sequence
<220> FEATURE:
<223> OTHER INFORMATION: modified hinge region(U6-HC8)

<400> SEQUENCE: 103

Glu Pro Arg Asp Cys Gly Cys Lys Pro Cys Pro Pro Cys Pro
1               5                   10

<210> SEQ ID NO 104
<211> LENGTH: 13
<212> TYPE: PRT
<213> ORGANISM: Artificial Sequence
<220> FEATURE:
<223> OTHER INFORMATION: modified hinge region(U8-HC5)

<400> SEQUENCE: 104

Glu Lys Cys Asp Lys Thr His Thr Cys Pro Pro Cys Pro
1               5                   10

<210> SEQ ID NO 105
<211> LENGTH: 15
<212> TYPE: PRT
<213> ORGANISM: Artificial Sequence
<220> FEATURE:
<223> OTHER INFORMATION: human hinge region

<400> SEQUENCE: 105

Glu Pro Lys Ser Cys Asp Lys Thr His Thr Cys Pro Pro Cys Pro
1               5                   10                  15

<210> SEQ ID NO 106
<211> LENGTH: 17
<212> TYPE: PRT
<213> ORGANISM: Artificial Sequence
<220> FEATURE:
<223> OTHER INFORMATION: CDR-L1 of antibody L3-11Y

<400> SEQUENCE: 106

Lys Ser Ser Gln Ser Leu Leu Ala Trp Gly Asn Gln Asn Asn Tyr Leu

-continued

```
              1               5                  10                 15

Ala
```

<210> SEQ ID NO 107
<211> LENGTH: 114
<212> TYPE: PRT
<213> ORGANISM: Artificial Sequence
<220> FEATURE:
<223> OTHER INFORMATION: amino acid sequence of light chain variable
      region of antibody L3-11Y

<400> SEQUENCE: 107

```
Asp Ile Gln Met Thr Gln Ser Pro Ser Ser Leu Ser Ala Ser Val Gly
  1               5                  10                  15

Asp Arg Val Thr Ile Thr Cys Lys Ser Gln Ser Leu Leu Ala Trp
             20                  25                  30

Gly Asn Gln Asn Asn Tyr Leu Ala Trp Tyr Gln Gln Lys Pro Gly Lys
         35                  40                  45

Ala Pro Lys Met Leu Ile Ile Trp Ala Ser Thr Arg Val Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Tyr Thr Phe Gly Gln Gly Thr Lys Val Glu Ile
                100                 105                 110

Lys Arg
```

<210> SEQ ID NO 108
<211> LENGTH: 220
<212> TYPE: PRT
<213> ORGANISM: Artificial Sequence
<220> FEATURE:
<223> OTHER INFORMATION: amino acid sequence of light chain of antibody
      L3-11Y

<400> SEQUENCE: 108

```
Asp Ile Gln Met Thr Gln Ser Pro Ser Ser Leu Ser Ala Ser Val Gly
  1               5                  10                  15

Asp Arg Val Thr Ile Thr Cys Lys Ser Gln Ser Leu Leu Ala Trp
             20                  25                  30

Gly Asn Gln Asn Asn Tyr Leu Ala Trp Tyr Gln Gln Lys Pro Gly Lys
         35                  40                  45

Ala Pro Lys Met Leu Ile Ile Trp Ala Ser Thr Arg Val Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Tyr Thr Phe Gly Gln Gly Thr Lys Val Glu Ile
                100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160
```

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 109
<211> LENGTH: 5
<212> TYPE: PRT
<213> ORGANISM: Artificial Sequence
<220> FEATURE:
<223> OTHER INFORMATION: CDR-H1 of anti-Ang2 antibody

<400> SEQUENCE: 109

Asp Tyr Ala Met Ser
 1               5

<210> SEQ ID NO 110
<211> LENGTH: 5
<212> TYPE: PRT
<213> ORGANISM: Artificial Sequence
<220> FEATURE:
<223> OTHER INFORMATION: CDR-H1 of anti-Ang2 antibody

<400> SEQUENCE: 110

Asp Tyr Tyr Met Ser
 1               5

<210> SEQ ID NO 111
<211> LENGTH: 5
<212> TYPE: PRT
<213> ORGANISM: Artificial Sequence
<220> FEATURE:
<223> OTHER INFORMATION: CDR-H1 of anti-Ang2 antibody

<400> SEQUENCE: 111

Asn Tyr Ala Met Ser
 1               5

<210> SEQ ID NO 112
<211> LENGTH: 5
<212> TYPE: PRT
<213> ORGANISM: Artificial Sequence
<220> FEATURE:
<223> OTHER INFORMATION: CDR-H1 of anti-Ang2 antibody

<400> SEQUENCE: 112

Asp Tyr Ala Met Ser
 1               5

<210> SEQ ID NO 113
<211> LENGTH: 5
<212> TYPE: PRT
<213> ORGANISM: Artificial Sequence
<220> FEATURE:
<223> OTHER INFORMATION: CDR-H1 of anti-Ang2 antibody

<400> SEQUENCE: 113

Asp Tyr Asp Met Ser
 1               5

<210> SEQ ID NO 114

```
<211> LENGTH: 5
<212> TYPE: PRT
<213> ORGANISM: Artificial Sequence
<220> FEATURE:
<223> OTHER INFORMATION: CDR-H1 of anti-Ang2 antibody

<400> SEQUENCE: 114

Asp Tyr Ala Met Ser
  1               5

<210> SEQ ID NO 115
<211> LENGTH: 5
<212> TYPE: PRT
<213> ORGANISM: Artificial Sequence
<220> FEATURE:
<223> OTHER INFORMATION: CDR-H1 of anti-Ang2 antibody

<400> SEQUENCE: 115

Ser Tyr Asp Met Ser
  1               5

<210> SEQ ID NO 116
<211> LENGTH: 5
<212> TYPE: PRT
<213> ORGANISM: Artificial Sequence
<220> FEATURE:
<223> OTHER INFORMATION: CDR-H1 of anti-Ang2 antibody

<400> SEQUENCE: 116

Asp Tyr Asp Met Ser
  1               5

<210> SEQ ID NO 117
<211> LENGTH: 17
<212> TYPE: PRT
<213> ORGANISM: Artificial Sequence
<220> FEATURE:
<223> OTHER INFORMATION: CDR-H2 of anti-Ang2 antibody

<400> SEQUENCE: 117

Ala Ile Tyr Pro Asp Ser Gly Asn Lys Tyr Tyr Ala Asp Ser Val Lys
  1               5                  10                  15

Gly

<210> SEQ ID NO 118
<211> LENGTH: 17
<212> TYPE: PRT
<213> ORGANISM: Artificial Sequence
<220> FEATURE:
<223> OTHER INFORMATION: CDR-H2 of anti-Ang2 antibody

<400> SEQUENCE: 118

Gly Ile Tyr Pro Ser Gly Gly Ser Thr Tyr Tyr Ala Asp Ser Val Lys
  1               5                  10                  15

Gly

<210> SEQ ID NO 119
<211> LENGTH: 17
<212> TYPE: PRT
<213> ORGANISM: Artificial Sequence
<220> FEATURE:
<223> OTHER INFORMATION: CDR-H2 of anti-Ang2 antibody

<400> SEQUENCE: 119

Ala Ile Ser Ser Gly Gly Gly Asn Ile Tyr Tyr Ala Asp Ser Val Lys
  1               5                  10                  15
```

Gly

```
<210> SEQ ID NO 120
<211> LENGTH: 17
<212> TYPE: PRT
<213> ORGANISM: Artificial Sequence
<220> FEATURE:
<223> OTHER INFORMATION: CDR-H2 of anti-Ang2 antibody

<400> SEQUENCE: 120
```

Ser Ile Tyr Pro Asp Asp Gly Asn Thr Tyr Tyr Ala Asp Ser Val Lys
 1               5                  10                  15

Gly

```
<210> SEQ ID NO 121
<211> LENGTH: 17
<212> TYPE: PRT
<213> ORGANISM: Artificial Sequence
<220> FEATURE:
<223> OTHER INFORMATION: CDR-H2 of anti-Ang2 antibody

<400> SEQUENCE: 121
```

Ser Ile Ser His Gly Asp Ser Asn Lys Tyr Tyr Ala Asp Ser Val Lys
 1               5                  10                  15

Gly

```
<210> SEQ ID NO 122
<211> LENGTH: 17
<212> TYPE: PRT
<213> ORGANISM: Artificial Sequence
<220> FEATURE:
<223> OTHER INFORMATION: CDR-H2 of anti-Ang2 antibody

<400> SEQUENCE: 122
```

Ser Ile Tyr Pro Asp Asp Gly Asn Thr Tyr Tyr Ala Asp Ser Val Lys
 1               5                  10                  15

Gly

```
<210> SEQ ID NO 123
<211> LENGTH: 17
<212> TYPE: PRT
<213> ORGANISM: Artificial Sequence
<220> FEATURE:
<223> OTHER INFORMATION: CDR-H2 of anti-Ang2 antibody

<400> SEQUENCE: 123
```

Leu Ile Ser Pro Asp Ser Ser Ser Ile Tyr Tyr Ala Asp Ser Val Lys
 1               5                  10                  15

Gly

```
<210> SEQ ID NO 124
<211> LENGTH: 17
<212> TYPE: PRT
<213> ORGANISM: Artificial Sequence
<220> FEATURE:
<223> OTHER INFORMATION: CDR-H2 of anti-Ang2 antibody

<400> SEQUENCE: 124
```

Gly Ile Ser Ser Asp Asp Gly Asn Thr Tyr Tyr Ala Asp Ser Val Lys
 1               5                  10                  15

Gly

```
<210> SEQ ID NO 125
<211> LENGTH: 20
<212> TYPE: PRT
<213> ORGANISM: Artificial Sequence
<220> FEATURE:
<223> OTHER INFORMATION: CDR-H3 of anti-Ang2 antibody

<400> SEQUENCE: 125

Ala Arg His Ser Ser Asp Pro Lys Val Lys Ser Gly Tyr Tyr Asp Asp
 1               5                  10                  15

Gly Met Asp Val
         20

<210> SEQ ID NO 126
<211> LENGTH: 14
<212> TYPE: PRT
<213> ORGANISM: Artificial Sequence
<220> FEATURE:
<223> OTHER INFORMATION: CDR-H3 of anti-Ang2 antibody

<400> SEQUENCE: 126

Ala Arg Asp Pro Ser Thr Leu Thr Tyr Ala Gly Phe Asp Tyr
 1               5                  10

<210> SEQ ID NO 127
<211> LENGTH: 20
<212> TYPE: PRT
<213> ORGANISM: Artificial Sequence
<220> FEATURE:
<223> OTHER INFORMATION: CDR-H3 of anti-Ang2 antibody

<400> SEQUENCE: 127

Ala Lys Ser Gly Ile Gln Pro Ser Pro Pro Ser Met Ser Ser Ala Tyr
 1               5                  10                  15

Ala Met Asp Val
         20

<210> SEQ ID NO 128
<211> LENGTH: 20
<212> TYPE: PRT
<213> ORGANISM: Artificial Sequence
<220> FEATURE:
<223> OTHER INFORMATION: CDR-H3 of anti-Ang2 antibody

<400> SEQUENCE: 128

Ala Arg His Thr Ser His His Thr Ser Ile Asp Gly Tyr Tyr Tyr Tyr
 1               5                  10                  15

Gly Met Asp Gly
         20

<210> SEQ ID NO 129
<211> LENGTH: 20
<212> TYPE: PRT
<213> ORGANISM: Artificial Sequence
<220> FEATURE:
<223> OTHER INFORMATION: CDR-H3 of anti-Ang2 antibody

<400> SEQUENCE: 129

Ala Lys Ser Ser Gly Ile Gln Glu Ser Pro Pro Thr Tyr Tyr Tyr Tyr
 1               5                  10                  15

Gly Met Asp Val
         20

<210> SEQ ID NO 130
<211> LENGTH: 20
```

```
<212> TYPE: PRT
<213> ORGANISM: Artificial Sequence
<220> FEATURE:
<223> OTHER INFORMATION: CDR-H3 of anti-Ang2 antibody

<400> SEQUENCE: 130

Ala Lys His Pro Val Arg Leu Asn Leu His Pro Met Tyr Tyr Tyr Tyr
 1               5                  10                  15

Gly Met Asp Val
            20

<210> SEQ ID NO 131
<211> LENGTH: 14
<212> TYPE: PRT
<213> ORGANISM: Artificial Sequence
<220> FEATURE:
<223> OTHER INFORMATION: CDR-H3 of anti-Ang2 antibody

<400> SEQUENCE: 131

Ala Lys Asp Leu Ile Ser Phe Trp Arg Gly Gly Phe Asp Tyr
 1               5                  10

<210> SEQ ID NO 132
<211> LENGTH: 20
<212> TYPE: PRT
<213> ORGANISM: Artificial Sequence
<220> FEATURE:
<223> OTHER INFORMATION: CDR-H3 of anti-Ang2 antibody

<400> SEQUENCE: 132

Ala Arg Pro Thr Ile Asp Lys Tyr Thr Leu Arg Gly Tyr Tyr Ser Tyr
 1               5                  10                  15

Gly Met Asp Val
            20

<210> SEQ ID NO 133
<211> LENGTH: 13
<212> TYPE: PRT
<213> ORGANISM: Artificial Sequence
<220> FEATURE:
<223> OTHER INFORMATION: CDR-L1 of anti-Ang2 antibody

<400> SEQUENCE: 133

Ser Gly Ser Ser Ser Asn Ile Gly Asn Asn Ala Val Asn
 1               5                  10

<210> SEQ ID NO 134
<211> LENGTH: 13
<212> TYPE: PRT
<213> ORGANISM: Artificial Sequence
<220> FEATURE:
<223> OTHER INFORMATION: CDR-L1 of anti-Ang2 antibody

<400> SEQUENCE: 134

Ser Gly Ser Ser Ser Asn Ile Gly Asn Asn Tyr Val Thr
 1               5                  10

<210> SEQ ID NO 135
<211> LENGTH: 13
<212> TYPE: PRT
<213> ORGANISM: Artificial Sequence
<220> FEATURE:
<223> OTHER INFORMATION: CDR-L1 of anti-Ang2 antibody

<400> SEQUENCE: 135

Ser Gly Ser Ser Ser Asn Ile Gly Asn Asn Asp Val Tyr
```

```
1               5                   10

<210> SEQ ID NO 136
<211> LENGTH: 13
<212> TYPE: PRT
<213> ORGANISM: Artificial Sequence
<220> FEATURE:
<223> OTHER INFORMATION: CDR-L1 of anti-Ang2 antibody

<400> SEQUENCE: 136

Thr Gly Ser Ser Ser Asn Ile Gly Asn Asn Asp Val Ser
1               5                   10

<210> SEQ ID NO 137
<211> LENGTH: 13
<212> TYPE: PRT
<213> ORGANISM: Artificial Sequence
<220> FEATURE:
<223> OTHER INFORMATION: CDR-L1 of anti-Ang2 antibody

<400> SEQUENCE: 137

Ser Gly Ser Ser Ser Asn Ile Gly Ser Asn Ala Val Asn
1               5                   10

<210> SEQ ID NO 138
<211> LENGTH: 13
<212> TYPE: PRT
<213> ORGANISM: Artificial Sequence
<220> FEATURE:
<223> OTHER INFORMATION: CDR-L1 of anti-Ang2 antibody

<400> SEQUENCE: 138

Thr Gly Ser Ser Ser Asn Ile Gly Asn Asn Ala Val Ser
1               5                   10

<210> SEQ ID NO 139
<211> LENGTH: 13
<212> TYPE: PRT
<213> ORGANISM: Artificial Sequence
<220> FEATURE:
<223> OTHER INFORMATION: CDR-L1 of anti-Ang2 antibody

<400> SEQUENCE: 139

Ser Gly Ser Ser Ser Asn Ile Gly Ser Asn Tyr Val Asn
1               5                   10

<210> SEQ ID NO 140
<211> LENGTH: 13
<212> TYPE: PRT
<213> ORGANISM: Artificial Sequence
<220> FEATURE:
<223> OTHER INFORMATION: CDR-L1 of anti-Ang2 antibody

<400> SEQUENCE: 140

Thr Gly Ser Ser Ser Asn Ile Gly Ser Asn Tyr Val Ser
1               5                   10

<210> SEQ ID NO 141
<211> LENGTH: 7
<212> TYPE: PRT
<213> ORGANISM: Artificial Sequence
<220> FEATURE:
<223> OTHER INFORMATION: CDR-L2 of anti-Ang2 antibody

<400> SEQUENCE: 141

Ala Asp Ser Asn Arg Pro Ser
1               5
```

```
<210> SEQ ID NO 142
<211> LENGTH: 7
<212> TYPE: PRT
<213> ORGANISM: Artificial Sequence
<220> FEATURE:
<223> OTHER INFORMATION: CDR-L2 of anti-Ang2 antibody

<400> SEQUENCE: 142

Ala Asp Ser His Arg Pro Ser
 1               5

<210> SEQ ID NO 143
<211> LENGTH: 7
<212> TYPE: PRT
<213> ORGANISM: Artificial Sequence
<220> FEATURE:
<223> OTHER INFORMATION: CDR-L2 of anti-Ang2 antibody

<400> SEQUENCE: 143

Ala Asn Ser His Arg Pro Ser
 1               5

<210> SEQ ID NO 144
<211> LENGTH: 7
<212> TYPE: PRT
<213> ORGANISM: Artificial Sequence
<220> FEATURE:
<223> OTHER INFORMATION: CDR-L2 of anti-Ang2 antibody

<400> SEQUENCE: 144

Ser Asp Ser Lys Arg Pro Ser
 1               5

<210> SEQ ID NO 145
<211> LENGTH: 7
<212> TYPE: PRT
<213> ORGANISM: Artificial Sequence
<220> FEATURE:
<223> OTHER INFORMATION: CDR-L2 of anti-Ang2 antibody

<400> SEQUENCE: 145

Ala Asp Ser Asn Arg Pro Ser
 1               5

<210> SEQ ID NO 146
<211> LENGTH: 7
<212> TYPE: PRT
<213> ORGANISM: Artificial Sequence
<220> FEATURE:
<223> OTHER INFORMATION: CDR-L2 of anti-Ang2 antibody

<400> SEQUENCE: 146

Ser Asp Ser Gln Arg Pro Ser
 1               5

<210> SEQ ID NO 147
<211> LENGTH: 7
<212> TYPE: PRT
<213> ORGANISM: Artificial Sequence
<220> FEATURE:
<223> OTHER INFORMATION: CDR-L2 of anti-Ang2 antibody

<400> SEQUENCE: 147

Ser Asp Ser His Arg Pro Ser
 1               5
```

```
<210> SEQ ID NO 148
<211> LENGTH: 7
<212> TYPE: PRT
<213> ORGANISM: Artificial Sequence
<220> FEATURE:
<223> OTHER INFORMATION: CDR-L2 of anti-Ang2 antibody

<400> SEQUENCE: 148

Ser Asp Asn Lys Arg Pro Ser
 1               5

<210> SEQ ID NO 149
<211> LENGTH: 9
<212> TYPE: PRT
<213> ORGANISM: Artificial Sequence
<220> FEATURE:
<223> OTHER INFORMATION: CDR-L3 of anti-Ang2 antibody

<400> SEQUENCE: 149

Gly Ser Trp Asp Tyr Ser Leu Ser Gly
 1               5

<210> SEQ ID NO 150
<211> LENGTH: 9
<212> TYPE: PRT
<213> ORGANISM: Artificial Sequence
<220> FEATURE:
<223> OTHER INFORMATION: CDR-L3 of anti-Ang2 antibody

<400> SEQUENCE: 150

Ala Thr Trp Asp Tyr Ser Leu Ser Gly
 1               5

<210> SEQ ID NO 151
<211> LENGTH: 9
<212> TYPE: PRT
<213> ORGANISM: Artificial Sequence
<220> FEATURE:
<223> OTHER INFORMATION: CDR-L3 of anti-Ang2 antibody

<400> SEQUENCE: 151

Gly Thr Trp Asp Tyr Ser Leu Ser Gly
 1               5

<210> SEQ ID NO 152
<211> LENGTH: 9
<212> TYPE: PRT
<213> ORGANISM: Artificial Sequence
<220> FEATURE:
<223> OTHER INFORMATION: CDR-L3 of anti-Ang2 antibody

<400> SEQUENCE: 152

Gly Ser Trp Asp Tyr Ser Leu Ser Gly
 1               5

<210> SEQ ID NO 153
<211> LENGTH: 9
<212> TYPE: PRT
<213> ORGANISM: Artificial Sequence
<220> FEATURE:
<223> OTHER INFORMATION: CDR-L3 of anti-Ang2 antibody

<400> SEQUENCE: 153

Gly Ser Trp Asp Tyr Ser Leu Ser Gly
 1               5
```

```
<210> SEQ ID NO 154
<211> LENGTH: 9
<212> TYPE: PRT
<213> ORGANISM: Artificial Sequence
<220> FEATURE:
<223> OTHER INFORMATION: CDR-L3 of anti-Ang2 antibody

<400> SEQUENCE: 154

Ala Thr Trp Asp Tyr Ser Leu Ser Ala
 1               5

<210> SEQ ID NO 155
<211> LENGTH: 9
<212> TYPE: PRT
<213> ORGANISM: Artificial Sequence
<220> FEATURE:
<223> OTHER INFORMATION: CDR-L3 of anti-Ang2 antibody

<400> SEQUENCE: 155

Gly Ala Trp Asp Asp Ser Leu Ser Gly
 1               5

<210> SEQ ID NO 156
<211> LENGTH: 9
<212> TYPE: PRT
<213> ORGANISM: Artificial Sequence
<220> FEATURE:
<223> OTHER INFORMATION: CDR-L3 of anti-Ang2 antibody

<400> SEQUENCE: 156

Gly Thr Trp Asp Asp Ser Leu Asn Gly
 1               5

<210> SEQ ID NO 157
<211> LENGTH: 5
<212> TYPE: PRT
<213> ORGANISM: Artificial Sequence
<220> FEATURE:
<223> OTHER INFORMATION: CDR-H1 of anti-Ang2 antibody
<220> FEATURE:
<221> NAME/KEY: UNSURE
<222> LOCATION: (1)
<223> OTHER INFORMATION: Xaa is Asp(D) or Asn(N)
<220> FEATURE:
<221> NAME/KEY: UNSURE
<222> LOCATION: (3)
<223> OTHER INFORMATION: Xaa is Ala(A), Asp(D), or Tyr(Y)

<400> SEQUENCE: 157

Xaa Tyr Xaa Met Ser
 1               5

<210> SEQ ID NO 158
<211> LENGTH: 17
<212> TYPE: PRT
<213> ORGANISM: Artificial Sequence
<220> FEATURE:
<223> OTHER INFORMATION: CDR-H2 of anti-Ang2 antibody
<220> FEATURE:
<221> NAME/KEY: UNSURE
<222> LOCATION: (1)
<223> OTHER INFORMATION: Xaa is Ala(A), Gly(G), or Ser(S)
<220> FEATURE:
<221> NAME/KEY: UNSURE
<222> LOCATION: (3)
<223> OTHER INFORMATION: Xaa is Tyr(Y) or Ser(S)
<220> FEATURE:
<221> NAME/KEY: UNSURE
<222> LOCATION: (4)
<223> OTHER INFORMATION: Xaa is Pro(P), His(H), or Ser(S)
<220> FEATURE:
```

```
<221> NAME/KEY: UNSURE
<222> LOCATION: (5)
<223> OTHER INFORMATION: Xaa is Asp(D), Gly(G), or Ser(S)
<220> FEATURE:
<221> NAME/KEY: UNSURE
<222> LOCATION: (6)
<223> OTHER INFORMATION: Xaa is Ser(S), Gly(G), or Asp(D)
<220> FEATURE:
<221> NAME/KEY: UNSURE
<222> LOCATION: (7)
<223> OTHER INFORMATION: Xaa is Gly(G) or Ser(S)
<220> FEATURE:
<221> NAME/KEY: UNSURE
<222> LOCATION: (8)
<223> OTHER INFORMATION: Xaa is Asn(N) or Ser(S)
<220> FEATURE:
<221> NAME/KEY: UNSURE
<222> LOCATION: (9)
<223> OTHER INFORMATION: Xaa is Lys(K), Ile(I), or Thr(T)

<400> SEQUENCE: 158

Xaa Ile Xaa Xaa Xaa Xaa Xaa Xaa Xaa Tyr Tyr Ala Asp Ser Val Lys
 1               5                  10                  15
Gly

<210> SEQ ID NO 159
<211> LENGTH: 13
<212> TYPE: PRT
<213> ORGANISM: Artificial Sequence
<220> FEATURE:
<223> OTHER INFORMATION: CDR-L1 of anti-Ang2 antibody
<220> FEATURE:
<221> NAME/KEY: UNSURE
<222> LOCATION: (1)
<223> OTHER INFORMATION: Xaa is Ser(S) or Thr(T)
<220> FEATURE:
<221> NAME/KEY: UNSURE
<222> LOCATION: (9)
<223> OTHER INFORMATION: Xaa is Asn(N) or Ser(S)
<220> FEATURE:
<221> NAME/KEY: UNSURE
<222> LOCATION: (11)
<223> OTHER INFORMATION: Xaa is Ala(A), Tyr(Y), or Asp(D)
<220> FEATURE:
<221> NAME/KEY: UNSURE
<222> LOCATION: (13)
<223> OTHER INFORMATION: Xaa is Asn(N), Ser(S), Thr(T), or Tyr(Y)

<400> SEQUENCE: 159

Xaa Gly Ser Ser Ser Asn Ile Gly Xaa Asn Xaa Val Xaa
 1               5                  10

<210> SEQ ID NO 160
<211> LENGTH: 7
<212> TYPE: PRT
<213> ORGANISM: Artificial Sequence
<220> FEATURE:
<223> OTHER INFORMATION: CDR-L2 of anti-Ang2 antibody
<220> FEATURE:
<221> NAME/KEY: UNSURE
<222> LOCATION: (1)
<223> OTHER INFORMATION: Xaa is Ala(A) or Ser(S)
<220> FEATURE:
<221> NAME/KEY: UNSURE
<222> LOCATION: (2)
<223> OTHER INFORMATION: Xaa is Asp(D) or Asn(N)
<220> FEATURE:
<221> NAME/KEY: UNSURE
<222> LOCATION: (3)
<223> OTHER INFORMATION: Xaa is Ser(S) or Asn(N)
<220> FEATURE:
<221> NAME/KEY: UNSURE
<222> LOCATION: (4)
<223> OTHER INFORMATION: Xaa is Asn(N), Lys(K), His(H), or Gln(Q)
```

```
<400> SEQUENCE: 160

Xaa Xaa Xaa Xaa Arg Pro Ser
 1               5

<210> SEQ ID NO 161
<211> LENGTH: 9
<212> TYPE: PRT
<213> ORGANISM: Artificial Sequence
<220> FEATURE:
<223> OTHER INFORMATION: CDR-L3 of anti-Ang2 antibody
<220> FEATURE:
<221> NAME/KEY: UNSURE
<222> LOCATION: (1)
<223> OTHER INFORMATION: Xaa is Gly(G) or Ala(A)
<220> FEATURE:
<221> NAME/KEY: UNSURE
<222> LOCATION: (2)
<223> OTHER INFORMATION: Xaa is Ser(S) or Thr(T)
<220> FEATURE:
<221> NAME/KEY: UNSURE
<222> LOCATION: (5)
<223> OTHER INFORMATION: Xaa is Tyr(Y) or Asp(D)
<220> FEATURE:
<221> NAME/KEY: UNSURE
<222> LOCATION: (8)
<223> OTHER INFORMATION: Xaa is Ser(S) or Asn(N)
<220> FEATURE:
<221> NAME/KEY: UNSURE
<222> LOCATION: (9)
<223> OTHER INFORMATION: Xaa is Gly(G) or Ala(A)

<400> SEQUENCE: 161

Xaa Xaa Trp Asp Xaa Ser Leu Xaa Xaa
 1               5

<210> SEQ ID NO 162
<211> LENGTH: 127
<212> TYPE: PRT
<213> ORGANISM: Artificial Sequence
<220> FEATURE:
<223> OTHER INFORMATION: heavy chain antigen binding region (heavy
      chain variable region) of anti-Ang2 antibody

<400> SEQUENCE: 162

Glu Val Gln Leu Leu Glu Ser Gly Gly Gly Leu Val Gln Thr Gly Gly
 1               5                  10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Ala Ile Tyr Pro Asp Ser Gly Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ser Ser Asp Pro Lys Val Lys Ser Gly Tyr Tyr Asp Asp
            100                 105                 110

Gly Met Asp Val Trp Gly Gln Gly Thr Leu Val Ala Val Ser Ser
        115                 120                 125

<210> SEQ ID NO 163
<211> LENGTH: 121
<212> TYPE: PRT
<213> ORGANISM: Artificial Sequence
```

```
<220> FEATURE:
<223> OTHER INFORMATION: heavy chain antigen binding region(heavy chain
      variable region) of anti-Ang2 antibody

<400> SEQUENCE: 163

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Pro Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Ser Thr Leu Thr Tyr Ala Gly Phe Asp Tyr Trp Gly
            100                 105                 110

Gln Gly Thr Leu Val Thr Val Ser Ser
        115                 120

<210> SEQ ID NO 164
<211> LENGTH: 127
<212> TYPE: PRT
<213> ORGANISM: Artificial Sequence
<220> FEATURE:
<223> OTHER INFORMATION: heavy chain antigen binding region(heavy chain
      variable region) of anti-Ang2 antibody

<400> SEQUENCE: 164

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser Ser Gly Gly Gly Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Gly Ile Gln Pro Ser Pro Pro Ser Met Ser Ser Ala Tyr
            100                 105                 110

Ala Met Asp Val Trp Gly Gln Gly Thr Leu Val Thr Val Ser Ser
        115                 120                 125

<210> SEQ ID NO 165
<211> LENGTH: 127
<212> TYPE: PRT
<213> ORGANISM: Artificial Sequence
<220> FEATURE:
<223> OTHER INFORMATION: heavy chain antigen binding region(heavy
      chain variable region) of anti-Ang2 antibody

<400> SEQUENCE: 165

Glu Val Gln Leu Leu Glu Ser Gly Gly Gly Leu Val Gln Pro Gly Gly
 1               5                  10                  15
```

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
            35                  40                  45

Ser Ser Ile Tyr Pro Asp Asp Gly Asn Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Thr Ser His His Thr Ser Ile Asp Gly Tyr Tyr Tyr Tyr
            100                 105                 110

Gly Met Asp Gly Trp Gly Gln Gly Thr Leu Val Thr Val Ser Ser
            115                 120                 125

<210> SEQ ID NO 166
<211> LENGTH: 127
<212> TYPE: PRT
<213> ORGANISM: Artificial Sequence
<220> FEATURE:
<223> OTHER INFORMATION: heavy chain antigen binding region(heavy chain
      variable region) of anti-Ang2 antibody

<400> SEQUENCE: 166

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Lys Gly Leu Glu Trp Val
            35                  40                  45

Ser Ser Ile Ser His Gly Asp Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ser Gly Ile Gln Glu Ser Pro Pro Thr Tyr Tyr Tyr Tyr
            100                 105                 110

Gly Met Asp Val Trp Gly Gln Gly Thr Leu Val Thr Val Ser Ser
            115                 120                 125

<210> SEQ ID NO 167
<211> LENGTH: 127
<212> TYPE: PRT
<213> ORGANISM: Artificial Sequence
<220> FEATURE:
<223> OTHER INFORMATION: heavy chain antigen binding region(heavy chain
      variable region) of anti-Ang2 antibody

<400> SEQUENCE: 167

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
            35                  40                  45

Ser Ser Ile Tyr Pro Asp Asp Gly Asn Thr Tyr Tyr Ala Asp Ser Val
        50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys His Pro Val Arg Leu Asn Leu His Pro Met Tyr Tyr Tyr Tyr
            100                 105                 110

Gly Met Asp Val Trp Gly Gln Gly Thr Leu Val Thr Val Ser Ser
        115                 120                 125
```

<210> SEQ ID NO 168
<211> LENGTH: 121
<212> TYPE: PRT
<213> ORGANISM: Artificial Sequence
<220> FEATURE:
<223> OTHER INFORMATION: heavy chain antigen binding region(heavy chain variable region) of anti-Ang2 antibody

<400> SEQUENCE: 168

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Asp Met Ser Trp Val Arg Gln Ala Pro Gly Lys Gly Leu Glu Trp Val
         35                  40                  45

Ser Leu Ile Ser Pro Asp Ser Ser Ile Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Leu Ile Ser Phe Trp Arg Gly Gly Phe Tyr Trp Gly
            100                 105                 110

Gln Gly Thr Leu Val Thr Val Ser Ser
        115                 120
```

<210> SEQ ID NO 169
<211> LENGTH: 127
<212> TYPE: PRT
<213> ORGANISM: Artificial Sequence
<220> FEATURE:
<223> OTHER INFORMATION: heavy chain antigen binding region(heavy chain variable region) of anti-Ang2 antibody

<400> SEQUENCE: 169

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Tyr
             20                  25                  30

Asp Met Ser Trp Val Arg Gln Ala Pro Gly Lys Gly Leu Glu Trp Val
         35                  40                  45

Ser Gly Ile Ser Ser Asp Asp Gly Asn Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Pro Thr Ile Asp Lys Tyr Thr Leu Arg Gly Tyr Tyr Ser Tyr
            100                 105                 110
```

Gly Met Asp Val Trp Gly Gln Gly Thr Leu Val Thr Val Ser Ser
            115                 120                 125

<210> SEQ ID NO 170
<211> LENGTH: 111
<212> TYPE: PRT
<213> ORGANISM: Artificial Sequence
<220> FEATURE:
<223> OTHER INFORMATION: light chain antigen binding region(light chain
      variable region) of anti-Ang2 antibody

<400> SEQUENCE: 170

Gln Ser Val Leu Thr Gln Pro Pro Ser Ala Ser Gly Thr Pro Gly Gln
  1               5                  10                  15

Arg Val Thr Ile Ser Cys Ser Gly Ser Ser Asn Ile Gly Asn Asn
             20                  25                  30

Ala Val Asn Trp Tyr Gln Gln Leu Pro Gly Thr Ala Pro Lys Leu Leu
         35                  40                  45

Ile Tyr Ala Asp Ser Asn Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ser Trp Asp Tyr Ser Leu
                 85                  90                  95

Ser Gly Tyr Val Phe Gly Gly Gly Thr Lys Leu Thr Val Leu Gly
            100                 105                 110

<210> SEQ ID NO 171
<211> LENGTH: 111
<212> TYPE: PRT
<213> ORGANISM: Artificial Sequence
<220> FEATURE:
<223> OTHER INFORMATION: light chain antigen binding region(light chain
      variable region) of anti-Ang2 antibody

<400> SEQUENCE: 171

Gln Ser Val Leu Thr Gln Pro Pro Ser Ala Ser Gly Thr Pro Gly Gln
  1               5                  10                  15

Arg Val Thr Ile Ser Cys Ser Gly Ser Ser Asn Ile Gly Asn Asn
             20                  25                  30

Tyr Val Thr Trp Tyr Gln Gln Leu Pro Gly Thr Ala Pro Lys Leu Leu
         35                  40                  45

Ile Tyr Ala Asp Ser His Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Thr Trp Asp Tyr Ser Leu
                 85                  90                  95

Ser Gly Tyr Val Phe Gly Gly Gly Thr Lys Leu Thr Val Leu Gly
            100                 105                 110

<210> SEQ ID NO 172
<211> LENGTH: 111
<212> TYPE: PRT
<213> ORGANISM: Artificial Sequence
<220> FEATURE:
<223> OTHER INFORMATION: light chain antigen binding region(light chain
      variable region) of anti-Ang2 antibody

<400> SEQUENCE: 172

Gln Ser Val Leu Thr Gln Pro Pro Ser Ala Ser Gly Thr Pro Gly Gln

```
                1               5                  10                 15
Arg Val Thr Ile Ser Cys Ser Gly Ser Ser Asn Ile Gly Asn Asn
                     20                 25                 30

Asp Val Tyr Trp Tyr Gln Gln Leu Pro Gly Thr Ala Pro Lys Leu Leu
             35                 40                 45

Ile Tyr Ala Asn Ser His Arg Pro Ser Gly Val Pro Asp Arg Phe Ser
         50                 55                 60

Gly Ser Lys Ser Gly Thr Ser Ala Ser Leu Ala Ile Ser Gly Leu Arg
 65                 70                 75                 80

Ser Glu Asp Glu Ala Asp Tyr Tyr Cys Gly Thr Trp Asp Tyr Ser Leu
                 85                 90                 95

Ser Gly Tyr Val Phe Gly Gly Gly Thr Lys Leu Thr Val Leu Gly
            100                105                110

<210> SEQ ID NO 173
<211> LENGTH: 111
<212> TYPE: PRT
<213> ORGANISM: Artificial Sequence
<220> FEATURE:
<223> OTHER INFORMATION: light chain antigen binding region(light chain
      variable region) of anti-Ang2 antibody

<400> SEQUENCE: 173

Gln Ser Val Leu Thr Gln Pro Pro Ser Ala Ser Gly Thr Pro Gly Gln
 1               5                  10                 15

Arg Val Thr Ile Ser Cys Thr Gly Ser Ser Asn Ile Gly Asn Asn
                     20                 25                 30

Asp Val Ser Trp Tyr Gln Gln Leu Pro Gly Thr Ala Pro Lys Leu Leu
             35                 40                 45

Ile Tyr Ser Asp Ser Lys Arg Pro Ser Gly Val Pro Asp Arg Phe Ser
         50                 55                 60

Gly Ser Lys Ser Gly Thr Ser Ala Ser Leu Ala Ile Ser Gly Leu Arg
 65                 70                 75                 80

Ser Glu Asp Glu Ala Asp Tyr Tyr Cys Gly Ser Trp Asp Tyr Ser Leu
                 85                 90                 95

Ser Gly Tyr Val Phe Gly Gly Gly Thr Lys Leu Thr Val Leu Gly
            100                105                110

<210> SEQ ID NO 174
<211> LENGTH: 111
<212> TYPE: PRT
<213> ORGANISM: Artificial Sequence
<220> FEATURE:
<223> OTHER INFORMATION: light chain antigen binding region(light chain
      variable region) of anti-Ang2 antibody

<400> SEQUENCE: 174

Gln Ser Val Leu Thr Gln Pro Pro Ser Ala Ser Gly Thr Pro Gly Gln
 1               5                  10                 15

Arg Val Thr Ile Ser Cys Ser Gly Ser Ser Asn Ile Gly Ser Asn
                     20                 25                 30

Ala Val Asn Trp Tyr Gln Gln Leu Pro Gly Thr Ala Pro Lys Leu Leu
             35                 40                 45

Ile Tyr Ala Asp Ser Asn Arg Pro Ser Gly Val Pro Asp Arg Phe Ser
         50                 55                 60

Gly Ser Lys Ser Gly Thr Ser Ala Ser Leu Ala Ile Ser Gly Leu Arg
 65                 70                 75                 80

Ser Glu Asp Glu Ala Asp Tyr Tyr Cys Gly Ser Trp Asp Tyr Ser Leu
```

85                  90                  95

Ser Gly Tyr Val Phe Gly Gly Gly Thr Lys Leu Thr Val Leu Gly
            100                 105                 110

<210> SEQ ID NO 175
<211> LENGTH: 111
<212> TYPE: PRT
<213> ORGANISM: Artificial Sequence
<220> FEATURE:
<223> OTHER INFORMATION: light chain antigen binding region(light chain
      variable region) of anti-Ang2 antibody

<400> SEQUENCE: 175

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

Ala Val Ser Trp Tyr Gln Gln Leu Pro Gly Thr Ala Pro Lys Leu Leu
        35                  40                  45

Ile Tyr Ser Asp Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Ala Tyr Val Phe Gly Gly Gly Thr Lys Leu Thr Val Leu Gly
            100                 105                 110

<210> SEQ ID NO 176
<211> LENGTH: 111
<212> TYPE: PRT
<213> ORGANISM: Artificial Sequence
<220> FEATURE:
<223> OTHER INFORMATION: Synthetic light chain antigen binding region
      (light chain variable region) of anti-Ang2 antibody

<400> SEQUENCE: 176

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Asn Trp Tyr Gln Gln Leu Pro Gly Thr Ala Pro Lys Leu Leu
        35                  40                  45

Ile Tyr Ser Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Leu
                85                  90                  95

Ser Gly Tyr Val Phe Gly Gly Gly Thr Lys Leu Thr Val Leu Gly
            100                 105                 110

<210> SEQ ID NO 177
<211> LENGTH: 111
<212> TYPE: PRT
<213> ORGANISM: Artificial Sequence
<220> FEATURE:
<223> OTHER INFORMATION: light chain antigen binding region(light chain
      variable region) of anti-Ang2 antibody

<400> SEQUENCE: 177

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ser Asn
            20                  25                  30

Tyr Val Ser Trp Tyr Gln Gln Leu Pro Gly Thr Ala Pro Lys Leu Leu
            35                  40                  45

Ile Tyr Ser Asp Asn Lys Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Ser Leu
                85                  90                  95

Asn Gly Tyr Val Phe Gly Gly Gly Thr Lys Leu Thr Val Leu Gly
            100                 105                 110

<210> SEQ ID NO 178
<211> LENGTH: 5
<212> TYPE: PRT
<213> ORGANISM: Artificial Sequence
<220> FEATURE:
<223> OTHER INFORMATION: CDR-H1 of anti-Ang2 antibody

<400> SEQUENCE: 178

Ser Tyr Trp Leu Glu
1               5

<210> SEQ ID NO 179
<211> LENGTH: 5
<212> TYPE: PRT
<213> ORGANISM: Artificial Sequence
<220> FEATURE:
<223> OTHER INFORMATION: CDR-H1 of anti-Ang2 antibody

<400> SEQUENCE: 179

Asp Pro Tyr Ile His
1               5

<210> SEQ ID NO 180
<211> LENGTH: 5
<212> TYPE: PRT
<213> ORGANISM: Artificial Sequence
<220> FEATURE:
<223> OTHER INFORMATION: CDR-H1 of anti-Ang2 antibody

<400> SEQUENCE: 180

Asp Tyr Tyr Met Lys
1               5

<210> SEQ ID NO 181
<211> LENGTH: 5
<212> TYPE: PRT
<213> ORGANISM: Artificial Sequence
<220> FEATURE:
<223> OTHER INFORMATION: CDR-H1 of anti-Ang2 antibody

<400> SEQUENCE: 181

Asn Tyr Gly Met Asn
1               5

<210> SEQ ID NO 182
<211> LENGTH: 17
<212> TYPE: PRT
<213> ORGANISM: Artificial Sequence

```
<220> FEATURE:
<223> OTHER INFORMATION: CDR-H2 of anti-Ang2 antibody

<400> SEQUENCE: 182

Glu Ile Leu Pro Gly Ser Gly Ser Thr Asn Tyr Asn Glu Lys Phe Arg
 1               5                  10                  15
Gly

<210> SEQ ID NO 183
<211> LENGTH: 17
<212> TYPE: PRT
<213> ORGANISM: Artificial Sequence
<220> FEATURE:
<223> OTHER INFORMATION: CDR-H2 of anti-Ang2 antibody

<400> SEQUENCE: 183

Arg Ile Asp Pro Ala Asn Gly Asn Thr Lys Tyr Asp Pro Lys Phe Gln
 1               5                  10                  15
Gly

<210> SEQ ID NO 184
<211> LENGTH: 17
<212> TYPE: PRT
<213> ORGANISM: Artificial Sequence
<220> FEATURE:
<223> OTHER INFORMATION: CDR-H2 of anti-Ang2 antibody

<400> SEQUENCE: 184

Glu Ile Asn Pro Lys Asn Gly Asp Thr Phe Tyr Asn Gln Ile Phe Lys
 1               5                  10                  15
Gly

<210> SEQ ID NO 185
<211> LENGTH: 17
<212> TYPE: PRT
<213> ORGANISM: Artificial Sequence
<220> FEATURE:
<223> OTHER INFORMATION: CDR-H2 of anti-Ang2 antibody

<400> SEQUENCE: 185

Trp Ile Asn Thr Tyr Thr Gly Glu Pro Thr Tyr Ala Asp Asp Phe Lys
 1               5                  10                  15
Gly

<210> SEQ ID NO 186
<211> LENGTH: 12
<212> TYPE: PRT
<213> ORGANISM: Artificial Sequence
<220> FEATURE:
<223> OTHER INFORMATION: CDR-H3 of anti-Ang2 antibody

<400> SEQUENCE: 186

Gly Asn His Asn Ser Tyr Tyr Tyr Ala Met Asp Tyr
 1               5                  10

<210> SEQ ID NO 187
<211> LENGTH: 9
<212> TYPE: PRT
<213> ORGANISM: Artificial Sequence
<220> FEATURE:
<223> OTHER INFORMATION: CDR-H3 of anti-Ang2 antibody

<400> SEQUENCE: 187

Arg Trp Asp Gly Gly Gly Phe Asp Tyr
```

```
1               5

<210> SEQ ID NO 188
<211> LENGTH: 11
<212> TYPE: PRT
<213> ORGANISM: Artificial Sequence
<220> FEATURE:
<223> OTHER INFORMATION: CDR-H3 of anti-Ang2 antibody

<400> SEQUENCE: 188

Glu Asn Asp Tyr Asp Val Gly Phe Phe Asp Tyr
1               5                   10

<210> SEQ ID NO 189
<211> LENGTH: 9
<212> TYPE: PRT
<213> ORGANISM: Artificial Sequence
<220> FEATURE:
<223> OTHER INFORMATION: CDR-H3 of anti-Ang2 antibody

<400> SEQUENCE: 189

Asp His Asp Gly Tyr Leu Met Asp Tyr
1               5

<210> SEQ ID NO 190
<211> LENGTH: 15
<212> TYPE: PRT
<213> ORGANISM: Artificial Sequence
<220> FEATURE:
<223> OTHER INFORMATION: CDR-L1 of anti-Ang2 antibody

<400> SEQUENCE: 190

Arg Ala Ser Glu Ser Val Asp Ser Tyr Gly Asn Ser Phe Met His
1               5                   10                  15

<210> SEQ ID NO 191
<211> LENGTH: 11
<212> TYPE: PRT
<213> ORGANISM: Artificial Sequence
<220> FEATURE:
<223> OTHER INFORMATION: CDR-L1 of anti-Ang2 antibody

<400> SEQUENCE: 191

Arg Ala Ser Gln Asp Ile Ser Asn Tyr Leu Asn
1               5                   10

<210> SEQ ID NO 192
<211> LENGTH: 11
<212> TYPE: PRT
<213> ORGANISM: Artificial Sequence
<220> FEATURE:
<223> OTHER INFORMATION: CDR-L1 of anti-Ang2 antibody

<400> SEQUENCE: 192

Lys Ala Ser Gln Ser Val Ser Asn Asp Val Ala
1               5                   10

<210> SEQ ID NO 193
<211> LENGTH: 11
<212> TYPE: PRT
<213> ORGANISM: Artificial Sequence
<220> FEATURE:
<223> OTHER INFORMATION: CDR-L1 of anti-Ang2 antibody

<400> SEQUENCE: 193

Ser Thr Ser Gln Gly Ile Ser Asn Tyr Leu Asn
1               5                   10
```

```
<210> SEQ ID NO 194
<211> LENGTH: 7
<212> TYPE: PRT
<213> ORGANISM: Artificial Sequence
<220> FEATURE:
<223> OTHER INFORMATION: CDR-L2 of anti-Ang2 antibody

<400> SEQUENCE: 194

Arg Ala Ser Asn Leu Asp Ser
  1               5

<210> SEQ ID NO 195
<211> LENGTH: 7
<212> TYPE: PRT
<213> ORGANISM: Artificial Sequence
<220> FEATURE:
<223> OTHER INFORMATION: CDR-L2 of anti-Ang2 antibody

<400> SEQUENCE: 195

Tyr Thr Ser Arg Leu His Ser
  1               5

<210> SEQ ID NO 196
<211> LENGTH: 7
<212> TYPE: PRT
<213> ORGANISM: Artificial Sequence
<220> FEATURE:
<223> OTHER INFORMATION: CDR-L2 of anti-Ang2 antibody

<400> SEQUENCE: 196

Tyr Ala Ser Asn Arg Tyr Pro
  1               5

<210> SEQ ID NO 197
<211> LENGTH: 7
<212> TYPE: PRT
<213> ORGANISM: Artificial Sequence
<220> FEATURE:
<223> OTHER INFORMATION: CDR-L2 of anti-Ang2 antibody

<400> SEQUENCE: 197

Tyr Thr Ser Ser Leu His Ser
  1               5

<210> SEQ ID NO 198
<211> LENGTH: 9
<212> TYPE: PRT
<213> ORGANISM: Artificial Sequence
<220> FEATURE:
<223> OTHER INFORMATION: CDR-L3 of anti-Ang2 antibody

<400> SEQUENCE: 198

Gln Gln Ser Asn Glu Asp Pro Leu Thr
  1               5

<210> SEQ ID NO 199
<211> LENGTH: 9
<212> TYPE: PRT
<213> ORGANISM: Artificial Sequence
<220> FEATURE:
<223> OTHER INFORMATION: CDR-L3 of anti-Ang2 antibody

<400> SEQUENCE: 199

Gln Gln Gly Asn Thr Leu Pro Trp Thr
  1               5
```

```
<210> SEQ ID NO 200
<211> LENGTH: 9
<212> TYPE: PRT
<213> ORGANISM: Artificial Sequence
<220> FEATURE:
<223> OTHER INFORMATION: CDR-L3 of anti-Ang2 antibody

<400> SEQUENCE: 200

Gln Gln Asp Tyr Thr Ser Pro Trp Thr
 1               5

<210> SEQ ID NO 201
<211> LENGTH: 9
<212> TYPE: PRT
<213> ORGANISM: Artificial Sequence
<220> FEATURE:
<223> OTHER INFORMATION: CDR-L3 of anti-Ang2 antibody

<400> SEQUENCE: 201

Gln Gln Tyr Ser Lys Leu Pro Tyr Thr
 1               5

<210> SEQ ID NO 202
<211> LENGTH: 7
<212> TYPE: PRT
<213> ORGANISM: Artificial Sequence
<220> FEATURE:
<223> OTHER INFORMATION: CDR-L2 of anti-Ang2 antibody
<220> FEATURE:
<221> NAME/KEY: UNSURE
<222> LOCATION: (1)
<223> OTHER INFORMATION: Xaa is Arg(R) or Tyr(Y)
<220> FEATURE:
<221> NAME/KEY: UNSURE
<222> LOCATION: (2)
<223> OTHER INFORMATION: Xaa is Ala(A) or Thr(T)
<220> FEATURE:
<221> NAME/KEY: UNSURE
<222> LOCATION: (4)
<223> OTHER INFORMATION: Xaa is Asn(N), Arg(R), or Ser(S)
<220> FEATURE:
<221> NAME/KEY: UNSURE
<222> LOCATION: (5)
<223> OTHER INFORMATION: Xaa is Leu(L) or Arg(R)
<220> FEATURE:
<221> NAME/KEY: UNSURE
<222> LOCATION: (6)
<223> OTHER INFORMATION: Xaa is Asp(D), His(H), or Tyr(Y)
<220> FEATURE:
<221> NAME/KEY: UNSURE
<222> LOCATION: (7)
<223> OTHER INFORMATION: Xaa is Ser(S) or Pro(P)

<400> SEQUENCE: 202

Xaa Xaa Ser Xaa Xaa Xaa Xaa
 1               5

<210> SEQ ID NO 203
<211> LENGTH: 9
<212> TYPE: PRT
<213> ORGANISM: Artificial Sequence
<220> FEATURE:
<223> OTHER INFORMATION: CDR-L3 of anti-Ang2 antibody
<220> FEATURE:
<221> NAME/KEY: UNSURE
<222> LOCATION: (3)
<223> OTHER INFORMATION: Xaa is Ser(S), Gly(G), Asp(D) or Tyr(Y)
<220> FEATURE:
<221> NAME/KEY: UNSURE
<222> LOCATION: (4)
<223> OTHER INFORMATION: Xaa is Asn(N), Tyr(Y), or Ser(S)
<220> FEATURE:
```

```
<221> NAME/KEY: UNSURE
<222> LOCATION: (5)
<223> OTHER INFORMATION: Xaa is Glu(E), Thr(T), or Lys(K)
<220> FEATURE:
<221> NAME/KEY: UNSURE
<222> LOCATION: (6)
<223> OTHER INFORMATION: Xaa is Asp(D), Ser(S), or Leu(L)
<220> FEATURE:
<221> NAME/KEY: UNSURE
<222> LOCATION: (8)
<223> OTHER INFORMATION: Xaa is Leu(L), Trp(W), or Tyr(Y)

<400> SEQUENCE: 203

Gln Gln Xaa Xaa Xaa Xaa Pro Xaa Thr
  1               5

<210> SEQ ID NO 204
<211> LENGTH: 121
<212> TYPE: PRT
<213> ORGANISM: Artificial Sequence
<220> FEATURE:
<223> OTHER INFORMATION: heavy chain antigen binding region(heavy
      chain variable region) of anti-Ang2 antibody

<400> SEQUENCE: 204

Gln Val Gln Leu Gln Gln Ser Gly Ala Glu Leu Met Lys Pro Gly Ala
  1               5                  10                  15

Ser Val Lys Ile Ser Cys Lys Ala Thr Asp Tyr Thr Phe Ser Ser Tyr
             20                  25                  30

Trp Leu Glu Trp Leu Ile Gln Arg Pro Gly His Gly Leu Glu Trp Ile
         35                  40                  45

Gly Glu Ile Leu Pro Gly Ser Gly Ser Thr Asn Tyr Asn Glu Lys Phe
     50                  55                  60

Arg Gly Lys Ala Thr Phe Thr Glu Asp Thr Ser Ser Asn Thr Ala Tyr
 65                  70                  75                  80

Met Gln Leu Ser Ser Leu Thr Ser Glu Asp Ser Ala Val Tyr Tyr Cys
                 85                  90                  95

Ala Arg Gly Asn His Asn Ser Tyr Tyr Tyr Ala Met Asp Tyr Trp Gly
            100                 105                 110

Gln Gly Thr Ser Val Thr Val Ser Ser
        115                 120

<210> SEQ ID NO 205
<211> LENGTH: 111
<212> TYPE: PRT
<213> ORGANISM: Artificial Sequence
<220> FEATURE:
<223> OTHER INFORMATION: light chain antigen binding region(light chain
      variable region) of anti-Ang2 antibody

<400> SEQUENCE: 205

Asp Ile Val Leu Thr Gln Ser Pro Ala Ser Leu Ala Val Ser Leu Gly
  1               5                  10                  15

Gln Arg Ala Thr Ile Ser Cys Arg Ala Ser Glu Ser Val Asp Ser Tyr
             20                  25                  30

Gly Asn Ser Phe Met His Trp Tyr Gln Gln Lys Pro Gly Gln Pro Pro
         35                  40                  45

Lys Leu Leu Ile Tyr Arg Ala Ser Asn Leu Asp Ser Gly Ile Pro Ala
     50                  55                  60

Arg Phe Ser Gly Ser Gly Ser Arg Thr Asp Phe Thr Leu Thr Ile Asn
 65                  70                  75                  80

Pro Val Glu Ala Asp Asp Val Ala Thr Tyr Tyr Cys Gln Gln Ser Asn
```

```
                    85                  90                  95

Glu Asp Pro Leu Thr Phe Gly Ala Gly Thr Lys Leu Glu Leu Lys
                100                 105                 110

<210> SEQ ID NO 206
<211> LENGTH: 118
<212> TYPE: PRT
<213> ORGANISM: Artificial Sequence
<220> FEATURE:
<223> OTHER INFORMATION: heavy chain antigen binding region(heavy chain
      variable region) of anti-Ang2 antibody

<400> SEQUENCE: 206

Glu Val Gln Leu Gln Gln Ser Gly Ala Glu Leu Val Lys Pro Gly Ala
  1               5                  10                  15

Ser Val Lys Leu Ser Cys Thr Ala Ser Gly Phe Asn Ile Lys Asp Pro
                 20                  25                  30

Tyr Ile His Trp Val Lys Gln Arg Pro Glu Gln Gly Leu Glu Trp Ile
             35                  40                  45

Gly Arg Ile Asp Pro Ala Asn Gly Asn Thr Lys Tyr Asp Pro Lys Phe
         50                  55                  60

Gln Gly Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Val Arg Arg Trp Asp Gly Gly Phe Asp Tyr Trp Gly Gln Gly Thr
            100                 105                 110

Ser Val Thr Val Ser Ser
        115

<210> SEQ ID NO 207
<211> LENGTH: 107
<212> TYPE: PRT
<213> ORGANISM: Artificial Sequence
<220> FEATURE:
<223> OTHER INFORMATION: light chain antigen binding region(light chain
      variable region) of anti-Ang2 antibody

<400> SEQUENCE: 207

Asp Ile Gln Met Thr Gln Thr Thr Ser Ser Leu Ser Ala Ser Leu Gly
  1               5                  10                  15

Asp Arg Val Thr Ile Ser Cys Arg Ala Ser Gln Asp Ile Ser Asn Tyr
                 20                  25                  30

Leu Asn Trp Tyr Gln Gln Lys Pro Asp Gly Thr Val Lys Leu Leu Ile
             35                  40                  45

Tyr Tyr Thr Ser Arg Leu His Ser Gly Val Pro Ser Arg Phe Ser Gly
         50                  55                  60

Ser Gly Ser Gly Thr Asp Tyr Ser Leu Thr Ile Thr Asn Leu Glu Gln
 65                  70                  75                  80

Glu Asp Ile Ala Thr Tyr Phe Cys Gln Gln Gly Asn Thr Leu Pro Trp
                 85                  90                  95

Thr Phe Gly Gly Gly Thr Lys Leu Glu Ile Lys
            100                 105

<210> SEQ ID NO 208
<211> LENGTH: 120
<212> TYPE: PRT
<213> ORGANISM: Artificial Sequence
<220> FEATURE:
<223> OTHER INFORMATION: heavy chain antigen binding region(heavy chain
``` variable region) of anti-Ang2 antibody

<400> SEQUENCE: 208

Glu Val Gln Leu Gln Gln Ser Gly Pro Glu Leu Val Lys Pro Gly Asp
1               5                   10                  15

Ser Val Lys Met Ser Cys Lys Ala Ser Gly Tyr Thr Phe Thr Asp Tyr
            20                  25                  30

Tyr Met Lys Trp Val Arg Gln Ser His Gly Lys Ser Leu Gln Trp Val
        35                  40                  45

Gly Glu Ile Asn Pro Lys Asn Gly Asp Thr Phe Tyr Asn Gln Ile Phe
    50                  55                  60

Lys Gly Lys Ala Thr Leu Thr Val Asp Lys Ser Ser Thr Ala Tyr
65                  70                  75                  80

Met Gln Leu Thr Ser Leu Thr Ser Glu Asp Ser Ala Val Tyr Tyr Cys
                85                  90                  95

Thr Arg Glu Asn Asp Tyr Asp Val Gly Phe Phe Asp Tyr Trp Gly Gln
            100                 105                 110

Gly Thr Ser Val Thr Val Ser Ser
        115                 120

<210> SEQ ID NO 209
<211> LENGTH: 107
<212> TYPE: PRT
<213> ORGANISM: Artificial Sequence
<220> FEATURE:
<223> OTHER INFORMATION: light chain antigen binding region(light chain
      variable region) of anti-Ang2 antibody

<400> SEQUENCE: 209

Thr Ile Val Met Thr Gln Thr Pro Lys Phe Leu Leu Val Ser Ala Gly
1               5                   10                  15

Asp Arg Ile Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Pro Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Thr Ser Pro Trp
                85                  90                  95

Thr Phe Gly Gly Gly Thr Glu Leu Glu Ile Lys
            100                 105

<210> SEQ ID NO 210
<211> LENGTH: 118
<212> TYPE: PRT
<213> ORGANISM: Artificial Sequence
<220> FEATURE:
<223> OTHER INFORMATION: heavy chain antigen binding region(heavy chain
      variable region) of anti-Ang2 antibody

<400> SEQUENCE: 210

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

```
Gly Trp Ile Asn Thr Tyr Thr Gly Glu Pro Thr Tyr Ala Asp Asp Phe
     50                  55                  60

Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
             85                  90                  95

Ala Arg Asp His Asp Gly Tyr Leu Met Asp Tyr Trp Gly Gln Gly Thr
                100                 105                 110

Ser Val Thr Val Ser Ser
            115

<210> SEQ ID NO 211
<211> LENGTH: 107
<212> TYPE: PRT
<213> ORGANISM: Artificial Sequence
<220> FEATURE:
<223> OTHER INFORMATION: light chain antigen binding region(light chain
      variable region) of anti-Ang2 antibody

<400> SEQUENCE: 211

Asp Ile Gln Met Thr Gln Thr Thr Ser Ser Leu Ser Ala Ser Leu Gly
 1               5                  10                  15

Asp Arg Val Thr Ile Ser Cys Ser Thr Ser Gln Gly Ile Ser Asn Tyr
             20                  25                  30

Leu Asn Trp Tyr Gln Gln Lys Pro Asp Gly Thr Val Lys Leu Leu Ile
         35                  40                  45

Phe Tyr Thr Ser Ser Leu His Ser Gly Val Pro Ser Arg Phe Ser Gly
     50                  55                  60

Ser Gly Ser Gly Thr Asp Tyr Ser Leu Thr Ile Ser Asn Leu Glu Pro
 65                  70                  75                  80

Glu Asp Ile Ala Thr Tyr Tyr Cys Gln Gln Tyr Ser Lys Leu Pro Tyr
                 85                  90                  95

Thr Phe Gly Gly Gly Thr Lys Leu Glu Ile Lys
            100                 105

<210> SEQ ID NO 212
<211> LENGTH: 114
<212> TYPE: PRT
<213> ORGANISM: Artificial Sequence
<220> FEATURE:
<223> OTHER INFORMATION: light chain variable region of anti c-Met
      antibody

<400> SEQUENCE: 212

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
             20                  25                  30

Gly Asn Gln Asn Asn Tyr Leu Ala Trp Tyr Gln Gln Lys Pro Gly Lys
         35                  40                  45

Ala Pro Lys Met Leu Ile Ile Trp Ala Ser Thr Arg Val Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95
```

```
Ser Tyr Ser Arg Pro Tyr Thr Phe Gly Gln Gly Thr Lys Val Glu Ile
            100                 105                 110

Lys Arg
```

COMBINATION THERAPY USING ANTI-C-MET ANTIBODY AND ANTI-ANG-2 ANTIBODY

CROSS-REFERENCE TO RELATED APPLICATIONS

This application claims the benefit of Korean Patent Application No. 10-2013-0036506 filed on Apr. 3, 2013 with the Korean Intellectual Property Office, the entire disclosure of which is hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 176, 999 Bytes ASCII (Text) file named "716331Sequence-Listing_revised_2" created Apr. 12, 2016.

BACKGROUND OF THE INVENTION

1. Field

Provided is a pharmaceutical composition for combination therapy for an angiogenesis-associated disease, including a combination of an anti-c-Met antibody and an anti-Ang-2 antibody as an active ingredient.

2. Description of the Related Art

Angiogenesis is a physiological process through which new blood vessels form from pre-existing vessels. This is a normal and vital process in growth and development, as well as in wound healing and in the formation of granulation tissue. However, it is also a fundamental step in the transition of tumors from a benign state to a malignant state, in the onset of various other diseases including age-related macular degeneration and diabetic retinopathy, and in driving psoriasis, rheumatoid arthritis, and chronic inflammation.

Particularly, angiogenesis plays a critical role in the growth and metastasis of tumors, leading to the use of angiogenesis inhibitors in the treatment of cancer. In fact, extensive and intensive research on angiogenesis has been conducted by advanced countries and multinational pharmaceutical companies to develop cancer therapeutics with this new concept. Many therapeutic targets have been disclosed by the research. Among them are angiopoietins, protein growth factors promoting vasculature development and post-natal angiogenesis. There are now four identified angiopoietins: Ang-1, Ang-2, Ang-3 and Ang-4.

Ang-2 is known as an antagonist ligand for Tie-2, a vascular endothelial cell-specific receptor tyrosine kinase (RTK), used to block Tie-2-mediated cell signaling. This ligand competes with the agonist ligand Ang-1 for binding to Tie-2, interfering with the Ang-1-Tie-2-mediated signaling which contributes to the stability of endothelial cells, and thereby promoting angiogenesis through the dynamic rearrangement of blood vessels.

Because angiogenesis plays an essential role in tumor growth, inhibition of Tie-2-dependent Ang-2 function is expected to prevent the progression of cancer. In practice, active research has been conducted using Ang-2-specific antibodies in an attempt to prevent the progression of cancer.

However, a recent report indicates that, in the presence of angiogenesis inhibitors such as anti-Ag2 antibodies, cancer cells are rather prone to metastasis as a result of the mechanism by which cancer cells avoid a rapid hypoxic condition (Nat Rev Clin Oncol. 2011 Mar. 1; 8(4): 210-21). Thus, a technique for inhibiting angiogenesis even in a hypoxic condition is needed to prevent side effects.

BRIEF SUMMARY OF THE INVENTION

Provided herein is a method for inhibiting angiogenesis in a subject comprising administering to the subject an anti-c-Met antibody or an antigen-binding fragment thereof, and an anti-Ang-2 antibody or an antigen-binding fragment thereof, in combination simultaneously or sequentially. Related methods and compositions also are provided.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Figure 1:
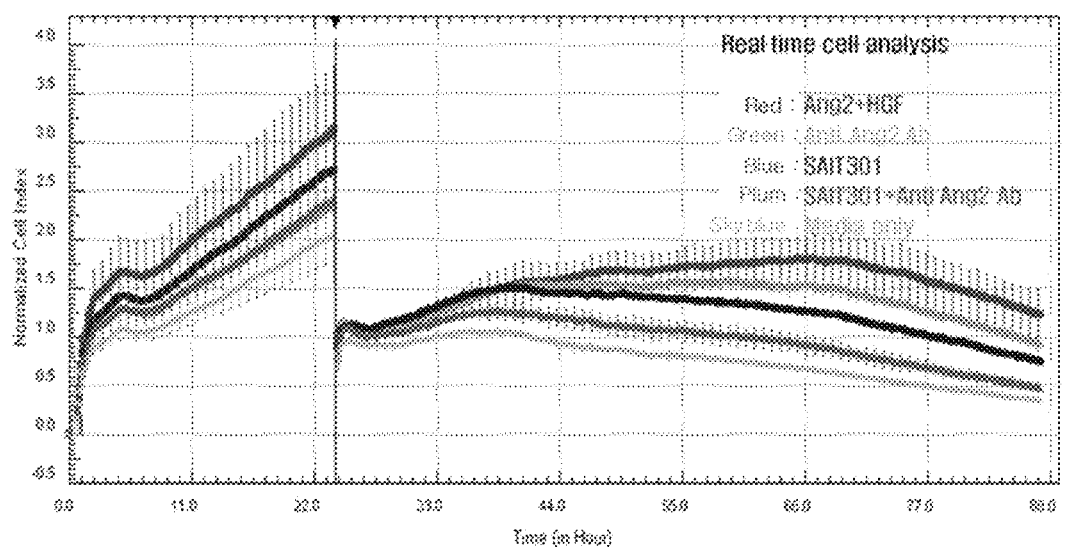
FIG. 1 is a graph of normalized cell index plotted against time, showing inhibitory activities of an anti-c-Met antibody (SAIT301) and an anti-Ang-2 antibody (SAIT-ANG-2-AB-4-H10; Tables 9~11), when administered alone or in combination, against the growth of cancer cells, as measured by real-time cell analysis.

An anti-c-Met antibody and an anti-Ang-2 antibody suppress the growth and metastasis of cancer and inhibit angiogenesis. Without wishing to be bound by any particular theory or mechanism of action, it is believed that the anti-c-Met antibody and an anti-Ang-2 antibody act by interfering with the migration of vascular endothelial cells, thereby exerting a significant synergistic prophylactic and therapeutic effect on various angiogenesis-related diseases including cancer and cancer metastasis, compared to either of the two antibodies individually.

It is believed that the combination therapy can not only effectively solve the problem associated with the conventional anti-Ang-2 antibody therapy, that is, the problem of promoting the metastasis of cancer due to the hypoxia-induced up-regulation of Ang-2, but also exhibits a synergistic effect on the prevention and treatment of various angiogenesis-related diseases including cancer and cancer metastasis.

In addition, the combination therapy may allow for use of the antibodies at a lower dose than the total dose of single antibody therapy, thus reducing side effects and increasing the patient's convenience.

One embodiment provides a pharmaceutical composition for combination therapy for an angiogenesis-related disease, including a combination of an anti-c-Met antibody or an antigen-binding fragment thereof, and an anti-Ang-2 antibody or an antigen-binding fragment thereof, as an active ingredient.

The pharmaceutical composition may be suppressive of both growth and metastasis of cancer cells. In addition, the pharmaceutical composition inhibits the migration of vascular and lymphatic endothelial cells. The combination therapy of the two antibodies exhibits an excellent dual effect of suppressing the growth and migration of cancer cells and inhibiting angiogenesis.

In an embodiment, the pharmaceutical composition for combination therapy may be formulated into a mixed form of an anti-c-Met antibody or an antigen-binding fragment thereof, and an anti-Ang-2 antibody or an antigen-binding fragment thereof, to simultaneously administer the antibodies at a predetermined dose.

In another embodiment, the pharmaceutical composition for combination therapy may be formulated into a dosage form in which an anti-c-Met antibody or an antigen-binding fragment thereof, and an anti-Ang-2 antibody or an antigen-binding fragment thereof, exist as separate preparations which can be administered simultaneously or sequentially. In this regard, the pharmaceutical composition for combination therapy may be divided into a first pharmaceutical composition including an effective amount of an anti-c-Met antibody as an active ingredient and a second pharmaceutical composition including an effective amount of an anti-Ang-2 antibody as an active ingredient, which can be administered simultaneously or sequentially. For sequential administration, any order of administration of the first and second compositions may be used.

Another embodiment provides a kit for the prevention and/or treatment of an angiogenesis-related disease, including an effective amount of an anti-c-Met antibody or an antigen-binding fragment thereof as an active ingredient (e.g., in a first container), a second pharmaceutical composition including an effective amount of an anti-Ang-2 antibody or an antigen-binding fragment thereof as an active ingredient (e.g., in a second container), and a package vessel (e.g., a container or package housing, containing, enveloping, or otherwise linking or associating the two separate formulations).

Another embodiment provides a method for treating an angiogenesis-related disease, including administering an effective amount of an anti-c-Met antibody or an antigen-binding fragment thereof, and an effective amount of an anti-Ang-2 antibody or an antigen-binding fragment thereof, in combination, to a subject in need thereof. This method may further comprise identifying a patient in need of the prevention and/or treatment of an angiogenesis-related disease ahead of the administering step.

In another embodiment, the administering may be conducted by administering a mixture including an effective amount of an anti-c-Met antibody and an effective amount of an anti-Ang-2 antibody. In yet another embodiment, the administering may be conducted by sequentially administering an effective amount of an anti-c-Met antibody and an effective amount of an anti-Ang-2 antibody in that order or in a reverse order.

The subject to be administered with the pharmaceutical composition may be a mammal including primates such as humans, monkeys, etc., and rodents such as mice and rats, with a preference for humans.

Examples of the angiogenesis-related disease include, but are not limited to, angiogenesis, cancer, cancer metastasis, eye diseases such as retinopathy of prematurity, macular degeneration (e.g., age-related macular degeneration), diabetic retinopathy, neovascular glaucoma, inflammatory diseases such as psoriasis, asthma, rheumatoid arthritis, pneumonia, chronic inflammation, infectious diseases, hypertension, arteriosclerosis, kidney-related disorders, and sepsis.

In addition, the cancer may be a solid cancer or a blood cancer. Examples of the cancer include, but are not limited to, squamous cell carcinoma, small cell lung cancer, non-small cell lung cancer, adenocarcinoma of the lung, squamous cell cancer of the lung, peritoneal cancer, skin cancer, skin or intraocular melanoma, rectal cancer, perianal cancer, esophageal cancer, small intestine cancer, adeno-endocrine carcinoma, parathyroid cancer, adrenal cancer, soft tissue sarcoma, urethral cancer, chronic or acute leukemia, lymphocytic lymphoma, hepatocyte cancer, stomach cancer, pancreatic cancer, glioblastoma, cervical cancer, ovarian cancer, hepatic cancer, bladder cancer, hepatoma, breast cancer, colon cancer, large intestine cancer, endometrial cancer or uterine cancer, salivary gland tumor, renal cancer, prostate cancer, vulvar cancer, thyroid cancer, head and neck cancer, brain cancer, and osteosarcoma.

As used herein, the term "pharmaceutically effective dose," "effective dose," or "effective amount" refers to a sufficient amount of the active ingredient to obtain a desired effect, that is, to suppress the growth and metastasis of cancer cells with the concomitant inhibition of angiogenesis. The effective amount may vary depending on various factors including a desired effect, the kind and severity of the disorder or symptom being treated, the state of a patient, the route of administration, the type of formulation, etc.

Unless otherwise stated, the anti-c-Met antibody and the anti-Ang-2 antibody which are used in the combination therapy are respective antibodies themselves or antigen-binding fragments thereof. The anti-c-Met antibody may recognize a certain site of c-Met, for example, the SEMA domain, as an epitope. So long as it binds to c-Met to induce the internalization and degradation of c-Met, any antibody or an antigen-binding fragment thereof may be used.

The term, "c-Met" or "c-Met protein", refers to a receptor tyrosine kinase binding to hepatocyte growth factor. The c-Met proteins may be derived from any species, for example, those derived from primates such as human c-Met (e.g., NP_000236) and monkey c-Met (e.g., *Macaca mulatta*, NP_001162100), or those derived from rodents such as mouse c-Met (e.g., NP_032617.2) and rat c-Met (e.g., NP_113705.1). The proteins include, for example, a polypeptide encoded by the nucleotide sequence deposited under GenBank Accession Number NM_000245, or a protein encoded by the polypeptide sequence deposited under GenBank Accession Number NM_000236, or extracellular domains thereof. The receptor tyrosine kinase c-Met is involved in several mechanisms including cancer incidence, cancer metastasis, cancer cell migration, cancer cell penetration, angiogenesis, etc.

c-Met, a receptor for hepatocyte growth factor (HGF), may be divided into three portions: extracellular, transmembrane, and intracellular. The extracellular portion is composed of an α-subunit and a β-subunit which are linked to each other through a disulfide bond, and contains a SEMA domain responsible for binding HGF, a PSI domain (plexin-semaphorins-integrin homology domain) and an IPT domain (immunoglobulin-like fold shared by plexins and transcriptional factors domain). The SEMA domain of c-Met protein may comprise the amino acid sequence of SEQ ID NO: 79, and is an extracellular domain that functions to bind HGF. A specific region of the SEMA domain, that is, a region having the amino acid sequence of SEQ ID NO: 71, which corresponds to a range from amino acid residues 106 to 124 of the amino acid sequence of the SEMA domain (SEQ ID NO: 79) of c-Met protein, is a loop region between the second and the third propellers within the epitopes of the SEMA domain. The region acts as one possible epitope for the specific anti-c-Met antibody of the present disclosure.

The term "epitope" as used herein, refers to an antigenic determinant, a part of an antigen recognized by an antibody. In one embodiment, the epitope may be a region including 5 or more contiguous (consecutive or non-consecutive) amino acid residues within the SEMA domain (SEQ ID NO: 79) of c-Met protein, for instance, 5 to 19 contiguous amino acid residues within the amino acid sequence of SEQ ID NO: 71. For example, the epitope may be a polypeptide having 5 to 19 contiguous amino acids selected from among partial combinations of the amino acid sequence of SEQ ID NO: 71, wherein the polypeptide essentially includes the amino sequence of SEQ ID NO: 73 (EEPSQ) serving as an essential element for the epitope. For example, the epitope may be a polypeptide comprising, consisting essentially of, or consisting of the amino acid sequence of SEQ ID NO: 71, SEQ ID NO: 72, or SEQ ID NO: 73.

The epitope having the amino acid sequence of SEQ ID NO: 72 corresponds to the outermost part of the loop between the second and third propellers within the SEMA domain of a c-Met protein. The epitope having the amino acid sequence of SEQ ID NO: 73 (EEPSQ) is a site to which the antibody or antigen-binding fragment according to one exemplary embodiment most specifically binds.

Thus, the anti-c-Met antibody may specifically bind to an epitope which has 5 to 19 contiguous amino acids selected from among partial combinations of the amino acid sequence of SEQ ID NO: 71, including SEQ ID NO: 73 as an essential element. For example, the anti-c-Met antibody may specifically bind to an epitope including the amino acid sequence of SEQ ID NO: 71, SEQ ID NO: 72, or SEQ ID NO: 73.

In one embodiment, the anti-c-Met antibody may be an antibody or an antigen-binding fragment thereof, which includes:

at least one heavy chain complementarity determining region (CDR) selected from the group consisting of (a) a CDR-H1 having the amino acid sequence of SEQ ID NO: 4; (b) a CDR-H2 having the amino acid sequence of SEQ ID NO: 5, SEQ ID NO: 2, or an amino acid sequence having 8-19 consecutive amino acids including amino acid residues from the $3^{rd}$ to $10^{th}$ positions of SEQ ID NO: 2; and (c) a CDR-H3 having the amino acid sequence of SEQ ID NO: 6, SEQ ID NO: 85, or an amino acid sequence having 6-13 consecutive amino acids including amino acid residues from the $1^{st}$ to $6^{th}$ positions of SEQ ID NO: 85, or a heavy chain variable region including the at least one heavy chain complementarity determining region;

at least one light chain complementarity determining region (CDR) selected from the group consisting of (a) a CDR-L1 having the amino acid sequence of SEQ ID NO: 7; (b) a CDR-L2 having the amino acid sequence of SEQ ID NO: 8, and (c) a CDR-L3 having the amino acid sequence of SEQ ID NO: 9, SEQ ID NO: 86, or an amino acid sequence having 9-17 consecutive amino acids including amino acid residues from the $1^{st}$ to $9^{th}$ positions of SEQ ID NO: 89, or a light chain variable region including the at least one light chain complementarity determining region, a combination of the at least one heavy chain complementarity determining region and the at least one light chain complementarity determining region; or a combination of the heavy chain variable region and the light chain variable region.

Herein, the amino acid sequences of SEQ ID NOS: 4 to 9 are respectively represented by the following Formulas I to VI, below:

$Xaa_1$-$Xaa_2$-Tyr-Tyr-Met-Ser (SEQ ID NO: 4), Formula I wherein $Xaa_1$ is absent or Pro or Ser, and $Xaa_2$ is Glu or Asp, Arg-Asn-$Xaa_3$-$Xaa_4$-Asn-Gly-$Xaa_5$-Thr (SEQ ID NO: 5), Formula II wherein $Xaa_3$ is Asn or Lys, $Xaa_4$ is Ala or Val, and $Xaa_5$ is Asn or Thr, Asp-Asn-Trp-Leu-$Xaa_6$-Tyr (SEQ ID NO: 6), Formula III wherein $Xaa_6$ is Ser or Thr, Lys-Ser-Ser-$Xaa_7$-Ser-Leu-Leu-Ala-$Xaa_8$-Gly-Asn-$Xaa_9$-$Xaa_{10}$-Asn-Tyr-Leu-Ala (SEQ ID NO: 7) Formula IV wherein $Xaa_7$ is His, Arg, Gln, or Lys, $Xaa_8$ is Ser or Trp, $Xaa_9$ is His or Gln, and $Xaa_{10}$ is Lys or Asn, Trp-$Xaa_{11}$-Ser-$Xaa_{12}$-Arg-Val-$Xaa_{13}$ (SEQ ID NO: 8) Formula V wherein $Xaa_{11}$ is Ala or Gly, $Xaa_{12}$ is Thr or Lys, and $Xaa_{13}$ is Ser or Pro, and $Xaa_{14}$-Gln-Ser-Tyr-Ser-$Xaa_{15}$-Pro-$Xaa_{16}$-Thr (SEQ ID NO: 9) Formula VI wherein $Xaa_{14}$ is Gly, Ala, or Gln, $Xaa_{15}$ is Arg, His, Ser, Ala, Gly, or Lys, and $Xaa_{16}$ is Leu, Tyr, Phe, or Met.

In one embodiment, the CDR-H1 may have an amino acid sequence selected from the group consisting of SEQ ID NOS: 1, 22, 23, and 24. The CDR-H2 may have an amino acid sequence selected from the group consisting of SEQ ID NOS: 2, 25, and 26. The CDR-H3 may have an amino acid sequence selected from the group consisting of SEQ ID NOS: 3, 27, 28, and 85.

The CDR-L1 may have an amino acid sequence selected from the group consisting of SEQ ID NOS: 10, 29, 30, 31, 32, 33, and 106. The CDR-L2 may have an amino acid sequence selected from the group consisting of SEQ ID NOS: 11, 34, 35, and 36. The CDR-L3 may have an amino acid sequence selected from the group consisting of SEQ ID NOS: 12, 13, 14, 15, 16, 37, 86, and 89.

In another embodiment, the antibody or the antigen-binding fragment may include a heavy variable region including a polypeptide (CDR-H1) having an amino acid sequence selected from the group consisting of SEQ ID NOS: 1, 22, 23, and 24, a polypeptide (CDR-H2) having an amino acid sequence selected from the group consisting of SEQ ID NOS: 2, 25, and 26, and a polypeptide (CDR-H3) having an amino acid sequence selected from the group consisting of SEQ ID NOS: 3, 27, 28, and 85; and a light variable region including a polypeptide (CDR-L1) having an amino acid sequence selected from the group consisting of SEQ ID NOS: 10, 29, 30, 31, 32, 33 and 106, a polypeptide (CDR-L2) having an amino acid sequence selected from the group consisting of SEQ ID NOS: 11, 34, 35, and 36, and a polypeptide (CDR-L3) having an amino acid sequence selected from the group consisting of SEQ ID NOS 12, 13, 14, 15, 16, 37, 86, and 89.

Animal-derived antibodies produced by immunizing non-immune animals with a desired antigen generally invoke immunogenicity when injected into humans for the purpose of medical treatment, and thus chimeric antibodies have been developed to inhibit such immunogenicity. Chimeric antibodies are prepared by replacing constant regions of animal-derived antibodies that cause an anti-isotype response with constant regions of human antibodies by genetic engineering. Chimeric antibodies are considerably improved in an anti-isotype response compared to animal-derived antibodies, but animal-derived amino acids still have variable regions, so that chimeric antibodies have side effects with respect to a potential anti-idiotype response. Humanized antibodies have been developed to reduce such side effects. Humanized antibodies are produced by grafting complementarity determining regions (CDR) which serve an important role in antigen binding in variable regions of chimeric antibodies into a human antibody framework.

An important aspect to consider in CDR grafting to produce humanized antibodies is choosing the optimized human antibodies for accepting CDRs of animal-derived antibodies. Antibody databases, analysis of a crystal structure, and technology for molecule modeling are used. However, even when the CDRs of animal-derived antibodies are grafted to the most optimized human antibody framework, amino acids positioned in a framework of the animal-derived CDRs affecting antigen binding are present. Therefore, in many cases, antigen binding affinity is not maintained, and thus application of additional antibody engineering technology for recovering the antigen binding affinity is necessary.

The anti c-Met antibodies may be mouse-derived antibodies, mouse-human chimeric antibodies, humanized antibodies, or human antibodies. The antibodies or antigen-binding fragments thereof may be isolated from a living body.

An intact antibody includes two full-length light chains and two full-length heavy chains, in which each light chain is linked to a heavy chain by disulfide bonds. The antibody has a heavy chain constant region and a light chain constant region. The heavy chain constant region is of a gamma (γ), mu (μ), alpha (α), delta (δ), or epsilon (ε) type, which may be further categorized as gamma 1 (γ1), gamma 2(γ2), gamma 3(γ3), gamma 4(γ4), alpha 1(α1), or alpha 2(α2). The light chain constant region is of either a kappa (κ) or lambda (λ) type.

As used herein, the term "heavy chain" refers to full-length heavy chain, and fragments thereof, including a variable region $V_H$ that includes amino acid sequences sufficient to provide specificity to antigens, and three constant regions, $C_{H1}$, $C_{H2}$, and $C_{H3}$, and a hinge. The term "light chain" refers to a full-length light chain and fragments thereof, including a variable region $V_L$ that includes amino acid sequences sufficient to provide specificity to antigens, and a constant region $C_L$.

The term "complementarity determining region (CDR)" refers to an amino acid sequence found in a hyper variable region of a heavy chain or a light chain of immunoglobulin. The heavy and light chains may respectively include three CDRs (CDRH1, CDRH2, and CDRH3; and CDRL1, CDRL2, and CDRL3). The CDR may provide contact residues that play an important role in the binding of antibodies to antigens or epitopes. The terms "specifically binding" and "specifically recognized" are well known to one of ordinary skill in the art, and indicate that an antibody and an antigen specifically interact with each other to lead to an immunological activity.

The term "antigen binding fragment" refers to a fragment of a full immunoglobulin structure including parts of the polypeptide including an antigen-binding region capable of binding to an antigen. In a particular embodiment, the antigen binding fragment may be selected from the group consisting of scFv, (scFv)$_2$, Fab, Fab', and F (ab')$_2$, but is not be limited thereto.

Out of the antigen binding fragments, Fab is a structure having variable regions of a light chain and a heavy chain, a constant region of the light chain, and the first constant region ($C_{H1}$) of the heavy chain, and it has one antigen binding site.

Fab' is different from Fab in that it has a hinge region including one or more cysteine residues at the C-terminal of heavy chain $C_{H1}$ domain. An F(ab')$_2$ antibody is formed through disulfide bond of the cysteine residues at the hinge region of Fab'.

An F(ab')$_2$ antibody is formed through disulfide bond of the cysteine residues at the hinge region of Fab'.

Fv is a minimal antibody piece having only a heavy chain variable region and light chain variable region, and a recombinant technique for producing the Fv fragment is well known in the pertinent art.

Two-chain Fv may have a structure in which the heavy chain variable region is linked to the light chain variable region by a non-covalent bond, and single-chain Fv (scFv) may generally have a dimer structure as in the two-chain Fv in which the variable region of a heavy chain and the variable region of a light chain are covalently linked via a peptide linker or they are directly linked to each other at the C-terminal thereof. The peptide linker may be the same as described above, for example, those having an amino acid length of 1 to 100, 2 to 50, particularly 5 to 25, and any kinds of amino acids may be included without any restrictions.

The antigen binding fragments may be obtained using proteases (for example, a whole antibody is digested with papain to obtain Fab fragments, and is digested with pepsin to obtain F(ab')$_2$ fragments), and may be prepared by a genetic recombinant technique.

The term "hinge region," as used herein, refers to a region between CH1 and CH2 domains within the heavy chain of an antibody which functions to provide flexibility for the antigen-binding site.

When an animal antibody undergoes a chimerization process, the IgG1 hinge of animal origin may be replaced with a human IgG1 hinge or IgG2 hinge while the disulfide bridges between two heavy chains are reduced from three to two in number. In addition, an animal-derived IgG1 hinge is shorter than a human IgG1 hinge. Accordingly, the rigidity of the hinge is changed. Thus, a modification of the hinge region may bring about an improvement in the antigen binding efficiency of the humanized antibody. The modification of the hinge region through amino acid deletion, addition, or substitution is well-known to those skilled in the art.

In one exemplary embodiment, the anti-c-Met antibody or an antigen-binding fragment thereof may be modified by the deletion, insertion, addition, or substitution of at least one amino acid residue on the amino acid sequence of the hinge region so that it exhibits enhanced antigen-binding efficiency. For example, the antibody may include a hinge region having the amino acid sequence of SEQ ID NO: 100(U7-HC6), 101(U6-HC7), 102(U3-HC9), 103(U6-HC8), or 104(U8-HC5), or a hinge region having the amino acid sequence of SEQ ID NO: 105 (non-modified human hinge). The hinge region may have the amino acid sequence of SEQ ID NO: 100 or 101.

In one embodiment of the anti-c-Met antibody or antigen-binding fragment, the variable domain of the heavy chain has the amino acid sequence of SEQ ID NO: 17, 74, 87, 90, 91, 92, 93, or 94 and the variable domain of the light chain has the amino acid sequence of SEQ ID NO: 18, 19, 20, 21, 75, 88, 95, 96, 97, 98, 99, or 107.

In one embodiment, the anti-c-Met antibody may be a monoclonal antibody. The monoclonal antibody may be produced by the hybridoma cell line deposited with Accession No. KCLRF-BP-00220, which binds specifically to the extracellular region of c-Met protein (refer to Korean Patent Publication No. 2011-0017698, the entire disclosures of which are incorporated herein by reference). The anti-c-Met antibody may include all the antibodies defined in Korean Patent Publication No. 2011-0017698.

In the anti-c-Met antibody, the rest portion of the light chain and the heavy chain portion excluding the CDRs, the light chain variable region, and the heavy chain variable region as defined above, that is the light chain constant region and the heavy chain constant region, may be those from any subtype of immunoglobulin (e.g., IgG1, IgG2, and the like).

By way of further example, the anti-c-Met antibody or the antibody fragment may include:

a heavy chain having the amino acid sequence selected from the group consisting of the amino acid sequence of SEQ ID NO: 62 (wherein the amino acid sequence from amino acid residues from the $1^{st}$ to $17^{th}$ positions is a signal peptide), or the amino acid sequence from the $18^{th}$ to $462^{nd}$ positions of SEQ ID NO: 62, the amino acid sequence of SEQ ID NO: 64 (wherein the amino acid sequence from the $1^{st}$ to $17^{th}$ positions is a signal peptide), the amino acid sequence from the $18^{th}$ to $461^{st}$ positions of SEQ ID NO: 64, the amino acid sequence of SEQ ID NO: (wherein the amino acid sequence from the $1^{st}$ to $17^{th}$ positions is a signal peptide), and the amino acid sequence from the $18^{th}$ to $460^{th}$ positions of SEQ ID NO: 66; and a light chain having the amino acid sequence selected from the group consisting of the amino acid sequence of SEQ ID NO: 68 (wherein the amino acid sequence from the $1^{st}$ to $20^{th}$ positions is a signal peptide), the amino acid sequence from the $21^{st}$ to $240^{th}$ positions of SEQ ID NO: 68, the amino acid sequence of SEQ ID NO: 70 (wherein the amino acid sequence from the $1^{st}$ to $20^{th}$ positions is a signal peptide), the amino acid sequence from the $21^{st}$ to $240^{th}$ positions of SEQ ID NO: 70, and the amino acid sequence of SEQ ID NO: 108.

For example, the anti-c-Met antibody may be selected from the group consisting of:

an antibody including a heavy chain having the amino acid sequence of SEQ ID NO: 62 or the amino acid sequence from the $18^{th}$ to $462^{nd}$ positions of SEQ ID NO: 62 and a light chain having the amino acid sequence of SEQ ID NO: 68 or the amino acid sequence from the $21^{st}$ to $240^{th}$ positions of SEQ ID NO: 68;

an antibody including a heavy chain having the amino acid sequence of SEQ ID NO: 64 or the amino acid sequence from the $18^{th}$ to $461^{st}$ positions of SEQ ID NO: 64 and a light chain having the amino acid sequence of SEQ ID NO: 68 or the amino acid sequence from the $21^{st}$ to $240^{th}$ positions of SEQ ID NO: 68;

an antibody including a heavy chain having the amino acid sequence of SEQ ID NO: 66 or the amino acid sequence from the $18^{th}$ to $460^{th}$ positions of SEQ ID NO: 66 and a light chain having the amino acid sequence of SEQ ID NO: 68 or the amino acid sequence from the $21^{st}$ to $240^{th}$ positions of SEQ ID NO: 68;

an antibody including a heavy chain having the amino acid sequence of SEQ ID NO: 62 or the amino acid sequence from the $18^{th}$ to $462^{nd}$ positions of SEQ ID NO: 62 and a light chain having the amino acid sequence of SEQ ID NO: 70 or the amino acid sequence from the $21^{st}$ to $240^{th}$ positions of SEQ ID NO: 70;

an antibody including a heavy chain having the amino acid sequence of SEQ ID NO: 64 or the amino acid sequence from the $18^{th}$ to $461^{st}$ positions of SEQ ID NO: 64 and a light chain having the amino acid sequence of SEQ ID NO: 70 or the amino acid sequence from the $21^{st}$ to $240^{th}$ positions of SEQ ID NO: 70;

an antibody including a heavy chain having the amino acid sequence of SEQ ID NO: 66 or the amino acid sequence from the $18^{th}$ to $460^{th}$ positions of SEQ ID NO: 66 and a light chain having the amino acid sequence of SEQ ID NO: 70 or the amino acid sequence from the $21^{st}$ to $240^{th}$ positions of SEQ ID NO: 70;

an antibody including a heavy chain having the amino acid sequence of SEQ ID NO: 62 or the amino acid sequence from the $18^{th}$ to $462^{nd}$ positions of SEQ ID NO: 62 and a light chain having the amino acid sequence of SEQ ID NO: 108;

an antibody including a heavy chain having the amino acid sequence of SEQ ID NO: 64 or the amino acid sequence from the $18^{th}$ to $461^{st}$ positions of SEQ ID NO: 64 and a light chain having the amino acid sequence of SEQ ID NO: 108; and an antibody including a heavy chain having the amino acid sequence of SEQ ID NO: 66 or the amino acid sequence from the $18^{th}$ to $460^{th}$ positions of SEQ ID NO: 66 and a light chain having the amino acid sequence of SEQ ID NO: 108.

The polypeptide of SEQ ID NO: 70 is a light chain including human kappa (K) constant region, and the polypeptide with the amino acid sequence of SEQ ID NO: 68 is a polypeptide obtained by replacing histidine at position 62 (corresponding to position 36 of SEQ ID NO: 68 according to kabat numbering) of the polypeptide with the amino acid sequence of SEQ ID NO: 70 with tyrosine. The production yield of the antibodies may be increased by the replacement. The polypeptide with the amino acid sequence of SEQ ID NO: 108 is a polypeptide obtained by replacing serine at position 32 (position 27e according to kabat numbering in the amino acid sequence from amino acid residues 21 to 240 of SEQ ID NO: 68; positioned within CDR-L1) with tryptophan. By such replacement, antibodies and antibody fragments including such sequences exhibits increased activities, such as c-Met biding affinity, c-Met degradation activity, Akt phosphorylation inhibition, and the like.

In another exemplary embodiment, the anti c-Met antibody may include a light chain complementarity determining region having the amino acid sequence of SEQ ID NO: 106, a light chain variable region having the amino acid sequence of SEQ ID NO: 107, or a light chain having the amino acid sequence of SEQ ID NO: 108.

The anti-Ang-2 antibody used in the combination therapy, unless stated otherwise, means the antibody itself (e.g., a full or complete antibody) or an antigen-binding fragment thereof.

The Ang-2, which the antibody provided according to one embodiment targets, may originate from mammals including primates, such as humans, monkeys, etc., and rodents, such as rats, mice, etc. For example, it may be human Ang-2 (Accession No. 015123), rhesus Ang-2 (e.g., NCBI Accession No. Q8MIK6), mouse Ang-2 (Accession No. NP_031452), or rat Ang-2 (e.g., NCBI Accession No. O35462) which originate, as implied by their names, from humans, monkeys, mice, and rats, respectively.

According to one embodiment, the anti-Ang-2 antibody may be a mouse antibody, a mouse-human chimeric antibody, or a humanized antibody.

In another embodiment, no particular limitations are imparted to the anti-Ang-2 antibody if it specifically binds to Ang-2. Any anti-Ang-2 antibody, whether already commercially available or under development, may be used. For example, the monoclonal antibodies MEDI3617 (MedImmune), 3.19.3 (AstraZeneca), REGN910 (Regeneron), and Ab536 (Roche), which are all in phase 1 trials, and the peptibodies AMG386 (Ang-1/2 targeting peptibody, Amgen), AMG780 (Ang-2 targeting peptibody, Amgen), CVX-060 (Pfizer), which are all in the form of Fc- or IgG-fused Ang-2 blocking peptides, may be used.

In another embodiment, the anti-Ang-2 antibody may contain a paratope, that is, an antigen-binding site including:

at least one heavy chain complementarity determining region (CDR) selected from the group consisting of three CDRs which have the amino acid sequence of SEQ ID NO: 157 (CDR-H1), the amino acid sequence of SEQ ID NO: 158 (CDR-H2), and the amino acid sequence of one of SEQ ID NOs: 125 to 130 (CDR-H3), respectively; and/or at least one light chain complementarity determining region (CDR) selected from the group consisting of three CDRs which have the amino acid sequence of SEQ ID NO: 159 (CDR-L1), the amino acid sequence of SEQ ID NO: 160 (CDR-L2), and the amino acid sequence of SEQ ID NO: 161 (CDR-L3), respectively:

X1-Y-X2-M-S (SEQ ID NO: 157)
wherein
X1 is aspartic acid (D), serine (S), or asparagine (N), and
X2 is alanine (A), aspartic acid (D), or tyrosine (Y);
X3-I-X4-X5-X6-X7-X8-X9-X10-Y-Y-A-D-S-V-K-G (SEQ ID NO: 158)
wherein
X3 is alanine (A), glycine (G), leucine (L), or serine (S),
X4 is tyrosine (Y) or serine (S),
X5 is proline (P), histidine (H), or serine (S),
X6 is aspartic acid (D), glycine (G), or serine (S),
X7 is serine (S), glycine (G), or aspartic acid (D),
X8 is glycine (G) or serine (S),
X9 is asparagine (N) or serine (S), and
X10 is lysine (K), isoleucine (I), or threonine (T);
X11-G-S-S-S-N-I-G-X12-N-X13-V-X14 (SEQ ID NO: 159)
wherein
X11 is serine (S) or threonine (T),
X12 is asparagine (N) or serine (S),
X13 is alanine (A), tyrosine (Y), or aspartic acid (D), and
X14 is asparagine (N), serine (S), threonine (T), or tyrosine (Y);
X15-X16-X17-X18-R-P-S (SEQ ID NO: 160)
wherein
X15 is alanine (A), or serine (S),
X16 is aspartic acid (D) or asparagine (N),
X17 is serine (S) or asparagine (N),
X18 is asparagine (N), lysine (K), histidine (H), or glutamine (Q); and
X19-X20-W-D-X21-S-L-X22-X23 (SEQ ID NO: 161)
wherein
X19 is glycine (G) or alanine (A),
X20 is serine (S), alanine (A), or threonine (T),
X21 is tyrosine (Y) or aspartic acid (D),
X22 is serine (S) or asparagines (N), and
X23 is glycine (G) or alanine (A).

For example, the antigen-binding site of the anti-Ang-2 antibody may include at least one heavy chain complementarity determining region (CDR) selected from the group consisting of a polypeptide having an amino acid sequence selected from among SEQ ID NOs: 109 to 116 (CDR-H1), a polypeptide having an amino acid sequence selected from among SEQ ID NOs: 117 to 124 (CDR-H2), and a polypeptide having an amino acid sequence selected from among SEQ ID NOs: 125 to 132 (CDR-H3); and/or at least one light chain complementarity determining region (CDR) selected from the group consisting of a polypeptide having an amino acid sequence selected from among SEQ ID NOs: 133 to 140 (CDR-L1), a polypeptide having an amino acid sequence selected from among SEQ ID NOs: 141 to 148 (CDR-L2), and a polypeptide having an amino acid sequence selected from among SEQ ID NOs: 149 to 156 (CDR-L3).

For example, the antigen-binding site of the anti-Ang-2 antibody may be composed of a heavy chain complementarity determining region having an amino acid sequence selected from among SEQ ID NOs: 162 to 169, and/or a light chain complementarity determining region having an amino acid sequence selected from among SEQ ID NOs: 170 to 177.

Amino acid sequences of the antigen-binding sites of the anti-Ang-2 antibody are summarized in Tables 1 to 3, below.

TABLE 1

Heavy chain CDR

| CDRH1-KABAT | CDRH2-KABAT | CDRH3-KABAT |
|---|---|---|
| DYAMS (SEQ ID NO: 109) | AIYPDSGNKYYADSVKG (SEQ ID NO: 117) | ARHSSDPKVKSGYYDD GMDV (SEQ ID NO: 125) |
| DYYMS (SEQ ID NO: 110) | GIYPSGGSTYYADSVKG (SEQ ID NO: 118) | ARDPSTLTYAGFDY (SEQ ID NO: 126) |
| NYAMS (SEQ ID NO: 111) | AISSGGGNIYYADSVKG (SEQ ID NO: 119) | AKSGIQPSPPSMSSAY AMDV (SEQ ID NO: 127) |
| DYAMS (SEQ ID NO: 112) | SIYPDDGNTYYADSVKG (SEQ ID NO: 120) | ARHTSHHTSIDGYYYY GMDG (SEQ ID NO: 128) |
| DYDMS (SEQ ID NO: 113) | SISHGDSNKYYADSVKG (SEQ ID NO: 121) | AKSSGIQESPPTYYYY GMDV (SEQ ID NO: 129) |
| DYAMS (SEQ ID NO: 114) | SIYPDDGNTYYADSVKG (SEQ ID NO: 122) | AKHPVRLNLHPMYYYY GMDV (SEQ ID NO: 130) |
| SYDMS (SEQ ID NO: 115) | LISPDSSSIYYADSVKG (SEQ ID NO: 123) | AKDLISFWRGGFDY (SEQ ID NO: 131) |
| DYDMS (SEQ ID NO: 116) | GISSDDGNTYYADSVKG (SEQ ID NO: 124) | ARPTIDKYTLRGYYSY GMDV (SEQ ID NO: 132) |

TABLE 2

Light chain CDR

| CDRL1-KABAT | CDRL2-KABAT | CDRL3-KABAT |
|---|---|---|
| SGSSSNIGNNAVN (SEQ ID NO: 133) | ADSNRPS (SEQ ID NO: 141) | GSWDYSLSG (SEQ ID NO: 149) |
| SGSSSNIGNNYVT (SEQ ID NO: 134) | ADSHRPS (SEQ ID NO: 142) | ATWDYSLSG (SEQ ID NO: 150) |

TABLE 2 -continued

| Light chain CDR | | |
|---|---|---|
| CDRL1-KABAT | CDRL2-KABAT | CDRL3-KABAT |
| SGSSSNIGNNDVY (SEQ ID NO: 135) | ANSHRPS (SEQ ID NO: 143) | GTWDYSLSG (SEQ ID NO: 151) |
| TGSSSNIGNNDVS (SEQ ID NO: 136) | SDSKRPS (SEQ ID NO: 144) | GSWDYSLSG (SEQ ID NO: 152) |
| SGSSSNIGSNAVN (SEQ ID NO: 137) | ADSNRPS (SEQ ID NO: 145) | GSWDYSLSG (SEQ ID NO: 153) |
| TGSSSNIGNNAVS (SEQ ID NO: 138) | SDSQRPS (SEQ ID NO: 146) | ATWDYSLSA (SEQ ID NO: 154) |
| SGSSSNIGSNYVN (SEQ ID NO: 139) | SDSHRPS (SEQ ID NO: 147) | GAWDDSLSG (SEQ ID NO: 155) |
| TGSSSNIGSNYVS (SEQ ID NO: 140) | SDNKRPS (SEQ ID NO: 148) | GTWDDSLNG (SEQ ID NO: 156) |

| Heavy chain binding region | Light chain binding region |
|---|---|
| EVQLLESGGGLVQTGGSLRLSCAAS GFTFSDYAMSWVRQAPGKGLEWVS AIYPDSGNKYYADSVKGRFTISRDN SKNTLYLQMNSLRAEDTAVYYCARH SSDPKVKSGYYDDGMDVWGQGTL VAVSS (SEQ ID NO: 162) | QSVLTQPPSASGTPGQRVTISCSGS SSNIGNNAVNWYQQLPGTAPKLLIYA DSNRPSGVPDRFSGSKSGTSASLAI SGLRSEDEADYYCGSWDYSLSGYV FGGGTKLTVLG (SEQ ID NO: 170) |
| EVQLLESGGGLVQPGGSLRLSCAAS GFTFSDYYMSWVRQAPGKGLEWVS GIYPSGGSTYYADSVKGRFTISRDNS KNTLYLQMNSLRAEDTAVYYCARDP STLTYAGFDYWGQGTLVTVSS (SEQ ID NO: 163) | QSVLTQPPSASGTPGQRVTISCSGS SSNIGNNYVTWYQQLPGTAPKLLIYA DSHRPSGVPDRFSGSKSGTSASLAI SGLRSEDEADYYCATWDYSLSGYV FGGGTKLTVLG (SEQ ID NO: 171) |
| EVQLLESGGGLVQPGGSLRLSCAAS GFTFSNYAMSWVRQAPGKGLEWVS AISSGGGNIYYADSVKGRFTISRDNS KNTLYLQMNSLRAEDTAVYYCAKSG IQPSPPSMSSAYAMDVWGQGTLVT VSS (SEQ ID NO: 164) | QSVLTQPPSASGTPGQRVTISCSGS SSNIGNNDVYWYQQLPGTAPKLLIYA NSHRPSGVPDRFSGSKSGTSASLAI SGLRSEDEADYYCGTWDYSLSGYV FGGGTKLTVLG (SEQ ID NO: 172) |
| EVQLLESGGGLVQPGGSLRLSCAAS GFTFSDYAMSWVRQAPGKGLEWVS SIYPDDGNTYYADSVKGRFTISRDNS KNTLYLQMNSLRAEDTAVYYCARHT SHHTSIDGYYYGMDGWGQGTLVT VSS (SEQ ID NO: 165) | QSVLTQPPSASGTPGQRVTISCTGS SSNIGNNDVSWYQQLPGTAPKLLIYS DSKRPSGVPDRFSGSKSGTSASLAI SGLRSEDEADYYCGSWDYSLSGYV FGGGTKLTVLG (SEQ ID NO: 173) |
| EVQLLESGGGLVQPGGSLRLSCAAS GFTFSDYDMSWVRQAPGKGLEWVS SISHGDSNKYYADSVKGRFTISRDN SKNTLYLQMNSLRAEDTAVYYCAKS SGIQESPPTYYYYGMDVWGQGTLVT VSS (SEQ ID NO: 166) | QSVLTQPPSASGTPGQRVTISCSGS SSNIGSNAVNWYQQLPGTAPKLLIYA DSNRPSGVPDRFSGSKSGTSASLAI SGLRSEDEADYYCGSWDYSLSGYV FGGGTKLTVLG (SEQ ID NO: 174) |
| EVQLLESGGGLVQTGGSLRLSCAAS GFTFSDYAMSWVRQAPGKGLEWVS SIYPDDGNTYYADSVKGRFTISRDNS KNTLYLQMNSLRAEDTAVYYCAKHP VRLNLHPMYYYYGMDVWGQGTLVT VSS (SEQ ID NO: 167) | QSVLTQPPSASGTPGQRVTISCTGS SSNIGNNAVSWYQQLPGTAPKLLIYS DSQRPSGVPDRFSGSKSGTSASLAI SGLRSEDEADYYCATWDYSLSAYVF GGGTKLTVLG (SEQ ID NO: 175) |
| EVQLLESGGGLVQPGGSLRLSCAAS GFTFSSYDMSWVRQAPGKGLEWVS LISPDSSSIYYADSVKGRFTISRDNSK NTLYLQMNSLRAEDTAVYYCAKDLIS FWRGGFDYWGQGTLVTVSS (SEQ ID NO: 168) | QSVLTQPPSASGTPGQRVTISCSGS SSNIGSNYVNWYQQLPGTAPKLLIYS DSHRPSGVPDRFSGSKSGTSASLAI SGLRSEDEADYYCGAWDDSLSGYV FGGGTKLTVLG (SEQ ID NO: 176) |

| Heavy chain binding region | Light chain binding region |
|---|---|
| EVQLLESGGGLVQPGGSLRLSCAAS<br>GFTFSDYDMSWVRQAPGKGLEWVS<br>GISSDDGNTYYADSVKGRFTISRDN<br>SKNTLYLQMNSLRAEDTAVYYCARP<br>TIDKYTLRGYYSYGMDVWGQGTLVT<br>VSS (SEQ ID NO: 169) | QSVLTQPPSASGTPGQRVTISCTGS<br>SSNIGSNYVSWYQQLPGTAPKLLIYS<br>DNKRPSGVPDRFSGSKSGTSASLAI<br>SGLRSEDEADYYCGTWDDSLNGYV<br>FGGGTKLTVLG (SEQ ID NO: 177) |

In another embodiment, the antigen-binding site of the anti-Ang-2 antibody may include:

at least one heavy chain complementarity determining region selected from the group consisting of three CDRs having an amino acid sequence selected from among SEQ ID NOs: 178 to 181 (CDR-H1), a polypeptide having an amino acid sequence selected from among SEQ ID NOs: 182 to 185 (CDR-H2), and a polypeptide having an amino acid sequence selected from among SEQ ID NOs: 186 to 189 (CDR-H3); and/or at least one light chain complementarity determining region selected from the group consisting of a polypeptide having an amino acid sequence selected from among SEQ ID NOs: 190 to 193 (CDR-L1), a polypeptide having an amino acid sequence of SEQ ID NO: 202 (CDR-L2), and a polypeptide having an amino acid sequence of SEQ ID NO: 203 (CDR-L3):

$X_1$-$X_2$-S-$X_3$-$X_4$-$X_5$-$X_6$ (SEQ ID NO: 202)

wherein $X_1$ is arginine (R) or tyrosine (Y), $X_2$ is alanine (A) or threonine (T), $X_3$ is asparagine (N), arginine (R), or serine (S), $X_4$ is leucine (L) or arginine (R), $X_5$ is aspartic acid (D), histidine (H), or tyrosine (Y), and $X_6$ is serine (S) or proline (P); and

Q-Q-$X_7$-$X_8$-$X_9$-$X_{10}$-P-$X_{11}$-T (SEQ ID NO: 203)

wherein $X_7$ is serine (S), glycine (G), aspartic acid (D), or tyrosine (Y), $X_8$ is asparagines (N), tyrosine (Y), or serine (S), $X_9$ is glutamic acid (E), threonine (T), or lysine (K), $X_{10}$ is aspartic acid (D), serine (S), or leucine (L), and $X_{11}$ is leucine (L), tryptophan (W), or tyrosine (Y).

For example, the antigen-binding site of the anti-Ang-2 antibody may include at least one heavy chain complementarity determining region selected from the group consisting of a polypeptide having an amino acid sequence selected from among SEQ ID NOs: 178 to 181 (CDR-H1), a polypeptide having an amino acid sequence selected from among SEQ ID NOs: 182 to SEQ ID NO: 185 (CDR-H2), and a polypeptide having an amino acid sequence selected from among SEQ ID NOs: 186 to 189 (CDR-H3); and/or at least one light chain complementarity determining region selected from the group consisting of a polypeptide having an amino acid sequence selected from among SEQ ID NOs: 190 to SEQ ID NO: 193 (CDR-L1), a polypeptide having an amino acid sequence selected from among SEQ ID NOs: 194 to 197 (CDR-L2), and a polypeptide having an amino acid sequence selected from among SEQ ID NOs: 198 to 201 (CDR-L3).

In one embodiment, the antigen-binding site of the anti-Ang-2 antibody may include a heavy chain complementarity determining region having an amino acid sequence selected from the group consisting of SEQ ID NO: 204, SEQ ID NO: 206, SEQ ID NO: 208, and SEQ ID NO: 210, and/or a light chain complementarity determining region having an amino acid sequence selected from the group consisting of SEQ ID NO: 205, SEQ ID NO: 207, SEQ ID NO: 209, and SEQ ID NO: 211.

Amino acid sequences of the antigen-binding site of the anti-Ang-2 antibody are summarized in Tables 4 to 6, below.

Table 4 indicates amino acid sequences of heavy chain CDR of anti-Ang-2 antibodies, Table 5 indicates amino acid sequences of light chain CDR of anti-Ang-2 antibodies, and Table 6 indicates amino acid sequences of heavy chain binding region and light chain binding region of anti-Ang-2 antibodies.

TABLE 4

Heavy chain CDR

| CDRH1-KABAT | CDRH2-KABAT | CDRH3-KABAT |
|---|---|---|
| SYWLE<br>(SEQ ID NO: 178) | EILPGSGSTNYNEKFRG<br>(SEQ ID NO: 182) | GNHNSYYYAMDY<br>(SEQ ID NO: 186) |
| DPYIH<br>(SEQ ID NO: 179) | RIDPANGNTKYDPKFQG<br>(SEQ ID NO: 183) | RWDGGGFDY<br>(SEQ ID NO: 187) |
| DYYMK<br>(SEQ ID NO: 180) | EINPKNGDTFYNQIFKG<br>(SEQ ID NO: 184) | ENDYDVGFFDY<br>(SEQ ID NO: 188) |
| NYGMN<br>(SEQ ID NO: 181) | WINTYTGEPTYADDFKG<br>(SEQ ID NO: 185) | DHDGYLMDY<br>(SEQ ID NO: 189) |

TABLE 5

Light chain CDR

| CDRL1-KABAT | CDRL2-KABAT | CDRL3-KABAT |
|---|---|---|
| RASESVDSYGNSFMH<br>(SEQ ID NO: 190) | RASNLDS<br>(SEQ ID NO: 194) | QQSNEDPLT<br>(SEQ ID NO: 198) |
| RASQDISNYLN<br>(SEQ ID NO: 191) | YTSRLHS<br>(SEQ ID NO: 195) | QQGNTLPWT<br>(SEQ ID NO: 199) |
| KASQSVSNDVA<br>(SEQ ID NO: 192) | YASNRYP<br>(SEQ ID NO: 196) | QQDYTSPWT<br>(SEQ ID NO: 200) |
| STSQGISNYLN<br>(SEQ ID NO: 193) | YTSSLHS<br>(SEQ ID NO: 197) | QQYSKLPYT<br>(SEQ ID NO: 201) |

TABLE 6

| Heavy chain binding region | Light chain binding region |
|---|---|
| QVQLQQSGAELMKPGASVKISCKATDYT FSSYWLEWLIQRPGHGLEWIGEILPGSG STNYNEKFRGKATFTEDTSSNTAYMQLS SLTSEDSAVYYCARGNHNSYYYAMDYW GQGTSVTVSS (SEQ ID NO: 204) | DIVLTQSPASLAVSLGQRATISCRASESV DSYGNSFMHWYQQKPGQPPKLLIYRAS NLDSGIPARFSGSGSRTDFTLTINPVEAD DVATYYCQQSNEDPLTFGAGTKLELK (SEQ ID NO: 205) |
| EVQLQQSGAELVKPGASVKLSCTASGFN IKDPYIHWVKQRPEQGLEWIGRIDPANG NTKYDPKFQGKATITADTSSNTAYLQLSS LTSEDTAVYYCVRRWDGGGFDYWGQG TSVTVSS (SEQ ID NO: 206) | DIQMTQTTSSLSASLGDRVTISCRASQDI SNYLNWYQQKPDGTVKLLIYYTSRLHSG VPSRFSGSGSGTDYSLTITNLEQEDIATY FCQQGNTLPWTFGGGTKLEIK (SEQ ID NO: 207) |
| EVQLQQSGPELVKPGDSVKMSCKASGY TFTDYYMKWVRQSHGKSLQWVGEINPK NGDTFYNQIFKGKATLTVDKSSSTAYMQ LTSLTSEDSAVYYCTRENDYDVGFFDYW GQGTSVTVSS (SEQ ID NO: 208) | TIVMTQTPKFLLVSAGDRITITCKASQSVS NDVAWYQQKPGQSPKLLIYYASNRYPG VPDRFTGSGYGTDFTFTISTVQAEDLAV YFCQQDYTSPWTFGGGTELEIK (SEQ ID NO: 209) |
| QIQLVQSGPELKKPGETVKISCKASGYTF TNYGMNWVKQAPGKGLKWMGWINTYT GEPTYADDFKGRFAFSLETSASTAYLQIN NLKNEDTATYFCARDHDGYLMDYWGQ GTSVTVSS (SEQ ID NO: 210) | DIQMTQTTSSLSASLGDRVTISCSTSQGI SNYLNWYQQKPDGTVKLLIFYTSSLHSG VPSRFSGSGSGTDYSLTISNLEPEDIATY YCQQYSKLPYTFGGGTKLEIK (SEQ ID NO: 211) |

According to a method that is well known to those skilled in the art, the pharmaceutical composition including the anti-c-Met antibody and the anti-Ang-2 antibody may be formulated, together with pharmaceutically acceptable carriers and/or excipients, into unit dose forms, or may be included within a multiple dose package. In this regard, the formulation may be in a liquid form of a solution in an oily or aqueous medium, a suspension, a syrup, or an emulsion, or in a solid form of an extract, a powder, a granule, a tablet, or a capsule, and may further include a dispersant or a stabilizer.

In addition, the pharmaceutical composition including an anti-c-Met antibody and an anti-Ang-2 antibody may be administered as a single therapeutic or in combination with a different therapeutic. In this case, the pharmaceutical composition may be administered sequentially or simultaneously with a conventional therapeutic.

Including an antibody or an antigen-binding fragment, the composition may be formulated as an immunoliposome. An antibody-containing liposome may be prepared using a method known in the art, or a combination thereof. A liposome is a lipid composition which may comprise phosphatidylcholine, cholesterol, and polyethylene glycol-derivated phosphatidylethanolamine, etc., and may be prepared, for example, by a reverse phase evaporation method. For example, Fab' fragments of an antibody may be conjugated to the liposome through a thiol-disulfide exchange reaction. A chemical drug, such as doxorubicin, may be further included in the liposome.

The composition including an effective amount of an anti-c-Met antibody and an effective amount of an anti-Ang-2 antibody in mixture, or in separate first and second compositions, respectively, may further include pharmaceutically acceptable carriers, diluents, and/or excipients.

Any pharmaceutically acceptable carrier that is typically used for formulating drugs may be available for the pharmaceutical composition including the antibodies in mixture or separately. Examples of the carrier include lactose, dextrose, sucrose, sorbitol, mannitol, starch, gum acacia, calcium phosphate, alginates, gelatin, calcium silicate, microcrystalline cellulose, polyvinylpyrrolidone, cellulose, water, syrup, methyl cellulose, methylhydroxy benzoate, propylhydroxy benzoate, talc, magnesium stearate, and mineral oil, but are not limited thereto. In addition to the carrier, the pharmaceutical composition may include at least one selected from among a diluent, an excipient, a lubricant, a wetting agent, a sweetener, a flavor enhancer, an emulsifier, a suspension agent, and a preservative.

The pharmaceutical composition may be administered orally or parenterally. Parenteral administration may include intravenous injection, subcutaneous injection, muscular injection, intraperitoneal injection, endothelial administration, local administration, intranasal administration, intrapulmonary administration, and rectal administration. Since oral administration leads to digestion of proteins or peptides, the composition may be coated or otherwise formulated to prevent digestion of the antibody or antigen-binding fragment thereof. In addition, the composition may be administered by a device capable of targeting the active material to a target cell.

A suitable dose of the pharmaceutical composition may vary depending on various factors including dosage forms of the formulation, administration method, a patient's age, weight, gender, health state, and diet, the time of administration, the time interval of administration, the route of administration, the rate of excretion, and sensitivity to the drug. For example, a suitable dose of the anti-c-Met antibody may range from about 0.01 to about 100 mg/kg, or from about 0.2 to about 10 mg/kg, while the anti-Ang-2 antibody or an antigen-binding fragment thereof may be administered at a dose of from about 0.001 to about 1000 mg/kg, or at a dose of from about 0.01 to about 100 mg/kg, or at a dose of from about 0.1 to about 50 mg/kg, or at a dose of from about 0.1 to about 20 mg/kg. The effective dose of the pharmaceutical composition may be formulated into a unit dose form or a separate dose form, or may be included within a multiple dose package. The anti-c-Met antibody and the anti-Ang-2 antibody may be packaged at respective unit doses in the kit.

An administration interval of combination therapy, which is defined as a term from one combination therapy to a subsequent one, may be on the order of from about 24 hrs to about 30 days, or on the order of about 7 days to about 14 days, but is not limited thereto. When the combination therapy is conducted by administering the first pharmaceutical composition including an effective amount of the anti-c-Met antibody and the second pharmaceutical composition including an effective amount of the anti-Ang-2 antibody, the first and second pharmaceutical compositions may be administered simultaneously or at regular intervals of 1 to 60 min, for example, 1 to 10 min, in that order or in a reverse order.

Exhibiting a preventive effect on the cancer aggravation attributed to migration, invasion, and metastasis of cancer cells as well as an inhibitory activity against the growth of cancer cells, the pharmaceutical composition of a combination therapy in accordance with the present invention is very effectively applicable to the prevention and treatment of both primary cancer and metastatic cancer, and various angiogenesis-related diseases.

In the combination therapy, the anti-c-Met antibody synergizes with the anti-Ang-2 antibody in suppressing the growth and metastasis of cancer, with the concomitant inhibition of angiogenesis, by interfering with the migration of vascular endothelial cells, thereby exerting a significantly high prophylactic and therapeutic effect on various angiogenesis-related diseases including cancer and cancer metastasis, compared to either of the two antibodies individually, or to conventional antibodies.

One or more embodiments will now be described in further detail with reference to the following examples. However, these examples are for the illustrative purposes only and are not intended to limit the scope of the invention.

Reference Example 1

Construction of Anti-1-Met Antibody 1.1. Production of "AbF46", a Mouse Antibody to c-Met
1.1.1. Immunization of Mouse To obtain immunized mice necessary for the development of a hybridoma cell line, each of five BALB/c mice (Japan SLC, Inc.), 4 to 6 weeks old, was intraperitoneally injected with a mixture of 100 µg of human c-Met/Fc fusion protein (R&D Systems) and one volume of complete Freund's adjuvant. Two weeks after the injection, a second intraperitoneal injection was conducted on the same mice with a mixture of 50 µg of human c-Met/Fc protein and one volume of incomplete Freund's adjuvant. One week after the second immunization, the immune response was finally boosted. Three days later, blood was taken from the tails of the mice and the sera were 1/1000 diluted in PBS and used to examine a titer of antibody to c-Met by ELISA. Mice found to have a sufficient antibody titer were selected for use in the cell fusion process.

1.1.2. Cell Fusion and Production of Hybridoma

Three days before cell fusion, BALB/c mice (Japan SLC, Inc.) were immunized with an intraperitoneal injection of a mixture of 50 µg of human c-Met/Fc fusion protein and one volume of PBS. The immunized mice were anesthetized before excising the spleen from the left half of the body. The spleen was meshed to separate splenocytes which were then suspended in a culture medium (DMEM, GIBCO, Invitrogen). The cell suspension was centrifuged to recover the cell layer. The splenocytes thus obtained ($1 \times 10^8$ cells) were mixed with myeloma cells (Sp2/0) ($1 \times 10^8$ cells), followed by spinning to give a cell pellet. The cell pellet was slowly suspended, treated with 45% polyethylene glycol (PEG) (1 mL) in DMEM for 1 min at 37° C., and supplemented with 1 mL of DMEM. To the cells was added 10 mL of DMEM over 10 min, after which incubation was conducted in a water bath at 37° C. for 5 min. Then the cell volume was adjusted to 50 mL before centrifugation. The cell pellet thus formed was resuspended at a density of $1\sim2\times10^5$ cells/mL in a selection medium (HAT medium) and 0.1 mL of the cell suspension was allocated to each well of 96-well plates which were then incubated at 37° C. in a $CO_2$ incubator to establish a hybridoma cell population.

1.1.3. Selection of Hybridoma Cells Producing Monoclonal Antibodies to c-Met Protein From the hybridoma cell population established in Reference Example 1.1.2, hybridoma cells which showed a specific response to c-Met protein were screened by ELISA using human c-Met/Fc fusion protein and human Fc protein as antigens.

Human c-Met/Fc fusion protein was seeded in an amount of 50 µL (2 µg/mL)/well to microtiter plates and allowed to adhere to the surface of each well. The antibody that remained unbound was removed by washing. For use in selecting the antibodies that do not bind c-Met but recognize Fc, human Fc protein was attached to the plate surface in the same manner.

The hybridoma cell culture obtained in Reference Example 1.1.2 was added in an amount of 50 µL to each well of the plates and incubated for 1 hour. The cells remaining unreacted were washed out with a sufficient amount of Tris-buffered saline and Tween 20 (TBST). Goat anti-mouse IgG-horseradish peroxidase (HRP) was added to the plates and incubated for 1 hour at room temperature. The plates were washed with a sufficient amount of TBST, followed by reacting the peroxidase with a substrate (OPD). Absorbance at 450 nm was measured on an ELISA reader.

Hybridoma cell lines which secrete antibodies that specifically and strongly bind to human c-Met but not human Fc were selected repeatedly. From the hybridoma cell lines obtained by repeated selection, a single clone producing a monoclonal antibody was finally separated by limiting dilution. The single clone of the hybridoma cell line producing the monoclonal antibody was deposited with the Korean Cell Line Research Foundation, an international depository authority located at Yungun-Dong, Jongno-Gu, Seoul, Korea, on Oct. 9, 2009, with Accession No. KCLRF-BP-00220 according to the Budapest Treaty (refer to Korean Patent Laid-Open Publication No. 2011-0047698).

1.1.4. Production and Purification of Monoclonal Antibody

The hybridoma cell line obtained in Reference Example 1.1.3 was cultured in a serum-free medium, and the monoclonal antibody (AbF46) was produced and purified from the cell culture.

First, the hybridoma cells cultured in 50 mL of a medium (DMEM) supplemented with 10% (v/v) FBS were centrifuged and the cell pellet was washed twice or more with 20 mL of PBS to remove the FBS therefrom. Then, the cells were resuspended in 50 mL of DMEM and incubated for 3 days at 37° C. in a $CO_2$ incubator.

After the cells were removed by centrifugation, the supernatant was stored at 4° C. before use or immediately used for the separation and purification of the antibody. An AKTA system (GE Healthcare) equipped with an affinity column (Protein G agarose column; Pharmacia, USA) was used to purify the antibody from 50 to 300 mL of the supernatant, followed by concentration with a filter (Amicon). The antibody in PBS was stored before use in the following examples.

1.2. Construction of chAbF46, a Chimeric Antibody to c-Met

A mouse antibody is apt to elicit immunogenicity in humans. To solve this problem, chAbF46, a chimeric antibody, was constructed from the mouse antibody AbF46 produced in Experimental Example 1.1.4 by replacing the constant region, but not the variable region responsible for antibody specificity, with an amino sequence of the human IgG1 antibody.

For this purpose, a gene was designed to include the nucleotide sequence of "EcoRI-signal sequence-VH-NheI-CH-TGA-XhoI" (SEQ ID NO: 38), coding for a heavy chain and the nucleotide sequence of "EcoRI-signal sequence-VL-BsiWI-CL-TGA-XhoI" (SEQ ID NO: 39), coding for a light chain and was synthesized. Then, a DNA fragment having the heavy chain nucleotide sequence (SEQ ID NO: 38) and a DNA fragment having the light chain nucleotide sequence (SEQ ID NO: 39) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen), and a pcDNA™ 3.3-TOPO TA Cloning Kit (Cat no. 8300-01), respectively.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. One day prior to transient expression, the cells were suspended at a concentration of $5 \times 10^5$ cells/ml, and after 24 hours, when the cell number reached $1 \times 10^6$ cells/ml, transient expression was initiated. A transfection was performed by a liposomal reagent method using Freestyle™ MAX reagent (invitrogen), wherein in a 15 ml tube, the DNA was provided in the mixture ratio of 1:1 (heavy chain DNA:light chain DNA) in a 15 ml tube and mixed with 2 ml of OptiPro™ SFM (invtrogen) (A), and in another 15 ml tube, 100 ul (microliter) of Freestyle™ MAX reagent and 2 ml of OptiPro™ SFM were mixed (B), followed by mixing (A) and (B) together and incubating for 15 minutes. The obtained mixture was slowly mixed with the cells provided one day prior to transient expression initiation. After completing the transfection, the cells were incubated in 130 rpm incubator for 5 days under the conditions of 37° C., 80% humidity, and 8% $CO_2$.

Afterwards, the cells were incubated in DMEM supplemented with 10% (v/v) FBS for 5 hours at 37° C. under a 5% $CO_2$ condition and then in FBS-free DMEM for 48 hours at 37° C. under a 5% $CO_2$ condition.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a chimeric antibody AbF46 (hereinafter referred to as "chAbF46").

1.3. Construction of Humanized Antibody huAbF46 from Chimeric Antibody chAbF46

1.3.1. Heavy Chain Humanization

To design two domains H1-heavy and H3-heavy, human germline genes which share the highest identity/homology with the VH gene of the mouse antibody AbF46 purified in Reference Example 1.2 were analyzed. An Ig BLAST (www.ncbi.nlm.nih.gov/igblast/) result revealed that VH3-71 has an identity/identity/homology of 83% at the amino acid level. CDR-H1, CDR-H2, and CDR-H3 of the mouse antibody AbF46 were defined according to Kabat numbering. A design was made to introduce the CDR of the mouse antibody AbF46 into the framework of VH3-71. Hereupon, back mutations to the amino acid sequence of the mouse AbF46 were conducted at positions 30 (S→T), 48 (V→L), 73 (D→N), and 78 (T→L). Then, H1 was further mutated at positions 83 (R→K) and 84 (A→T) to finally establish H1-heavy (SEQ ID NO: 40) and H3-heavy (SEQ ID NO: 41).

For use in designing H4-heavy, human antibody frameworks were analyzed by a BLAST search. The result revealed that the VH3 subtype, known to be most stable, is very similar in framework and sequence to the mouse antibody AbF46. CDR-H1, CDR-H2, and CDR-H3 of the mouse antibody AbF46 were defined according to Kabat numbering and introduced into the VH3 subtype to construct H4-heavy (SEQ ID NO: 42).

1.3.2. Light Chain Humanization

To design two domains H1-light (SEQ ID NO: 43) and H2-light (SEQ ID NO: 44), human germline genes which share the highest identity/homology with the VH gene of the mouse antibody AbF46 were analyzed. An Ig BLAST search result revealed that VK4-1 has an identity/homology of 75% at the amino acid level. CDR-L1, CDR-L2, and CDR-L3 of the mouse antibody AbF46 were defined according to Kabat numbering. A design was made to introduce the CDR of the mouse antibody AbF46 into the framework of VK4-1. Hereupon, back mutations to the amino acid sequence of the mouse AbF46 were conducted at positions 36 (Y→H), 46 (L→M), and 49 (Y→I). Only one back mutation was conducted at position 49 (Y→I) on H2-light.

To design H3-light (SEQ ID NO: 45), human germline genes which share the highest identity/homology with the VL gene of the mouse antibody AbF46 were analyzed by a search for BLAST. As a result, VK2-40 was selected. VL and VK2-40 of the mouse antibody AbF46 were found to have a identity/homology of 61% at an amino acid level. CDR-L1, CDR-L2, and CDR-L3 of the mouse antibody were defined according to Kabat numbering and introduced into the framework of VK4-1. Back mutations were conducted at positions 36 (Y→H), 46 (L→M), and 49 (Y→I) on H3-light.

For use in designing H4-light (SEQ ID NO: 46), human antibody frameworks were analyzed. A Blast search revealed that the Vk1 subtype, known to be the most stable, is very similar in framework and sequence to the mouse antibody AbF46. CDR-L1, CDR-L2, and CDR-L3 of the mouse antibody AbF46 were defined according to Kabat numbering and introduced into the Vk1 subtype. Hereupon, back mutations were conducted at positions 36 (Y→H), 46 (L→M), and 49 (Y→I) on H4-light.

Thereafter, DNA fragments comprising the heavy chain nucleotide sequences (H1-heavy: SEQ ID NO: 47, H3-heavy: SEQ ID NO: 48, H4-heavy: SEQ ID NO: 49) and DNA fragments comprising the light chain nucleotide sequences (H1-light: SEQ ID NO: 50, H2-light: SEQ ID NO: 51, H3-light: SEQ ID NO: 52, H4-light: SEQ ID NO: 53) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen) and a pcDNA™ 3.3-TOPO TA Cloning Kit (Cat no. 8300-01), respectively, so as to construct recombinant vectors for expressing a humanized antibody.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. One day prior to the transient expression, the cells were suspended at a concentration of 5×10⁵ cells/ml, and after 24 hours, when the cell number reached to 1×10⁶ cells/ml, the transient expression was initiated. A transfection was performed by a liposomal reagent method using Freestyle™ MAX reagent (invitrogen), wherein the DNA was provided in the mixture ratio of 1:1 (heavy chain DNA:light chain DNA) in a 15 ml tube and mixed with 2 ml of OptiPro™ SFM (invtrogen) (A), and in another 15 ml tube, 100 ul (microliter) of Freestyle™ MAX reagent and 2 ml of OptiPro™ SFM were mixed (B), followed by mixing (A) and (B) together and incubating for 15 minutes. The obtained mixture was slowly mixed with the cells provided one day prior to transient expression initiation. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a humanized antibody AbF46 (hereinafter referred to as "huAbF46"). The humanized antibody huAbF46 used in the following examples included a combination of H4-heavy (SEQ ID NO: 42) and H4-light (SEQ ID NO: 46).

1.4. Construction of scFV Library of huAbF46 Antibody

For use in constructing an scFv of the huAbF46 antibody from the heavy and light chain variable regions of the huAbF46 antibody, a gene was designed to have the structure of "VH-linker-VL" for both the heavy and the light chain variable region, with the linker having the amino acid sequence "GLGGLGGGGSGGGGSGGSSGVGS"(SEQ ID NO: 54). A polynucleotide sequence (SEQ ID NO: 55) encoding the designed scFv of huAbF46 was synthesized in Bioneer and an expression vector for the synthesized polynucleotide comprised the nucleotide sequence of SEQ ID NO: 56.

After expression, the product was found to exhibit specificity to c-Met.

1.5. Construction of Library Genes for Affinity Maturation 1.5.1. Selection of Target CDRs and Synthesis of Primers The affinity maturation of huAbF46 was achieved. First, six complementary determining regions (CDRs) were defined according to Kabat numbering. The CDRs are given in Table 7, below.

TABLE 7

| CDR | Amino Acid Sequence |
| --- | --- |
| CDR-H1 | DYYMS (SEQ ID NO: 1) |
| CDR-H2 | FIRNKANGYTTEYSASVKG (SEQ ID NO: 2) |
| CDR-H3 | DNWFAY (SEQ ID NO: 3) |
| CDR-L1 | KSSQSLLASGNQNNYLA (SEQ ID NO: 10) |
| CDR-L2 | WASTRVS (SEQ ID NO: 11) |
| CDR-L3 | QQSYSAPLT (SEQ ID NO: 12) |

For the purpose of introducing random sequences into the CDRs of the antibody, primers were designed as follows. Conventionally, N codons were utilized to introduce bases at the same ratio (25% A, 25% G, 25% C, 25% T) into desired sites of mutation. In this experiment, the introduction of random bases into the CDRs of huAbF46 was conducted in such a manner that, of the three nucleotides per codon in the wild-type polynucleotide encoding each CDR, 85% of the first nucleotide was conserved while the other three nucleotides were introduced at the same percentage (each 5%); 85% of the second nucleotide was conserved while the other three nucleotides were introduced into the rest (15%) of the second nucleotide at the same percentage (each 5%); and G, C and T were introduced into the third nucleotide at the same percentage (33% G, 33% C, 33% T).

1.5.2. Construction of a Library of huAbF46 Antibodies and Affinity for c-Met

The construction of antibody gene libraries through the introduction of random sequences was carried out using the primers synthesized in the same manner as in Reference Example 1.5.1. Two PCR products were obtained using a polynucleotide covering the scFV of huAbF46 as a template, and were subjected to overlap extension PCR to give scFv library genes for huAbF46 antibodies in which only desired CDRs were mutated. Libraries targeting each of the six CDRs prepared from the scFV library genes were constructed.

The affinity for c-Met of each library was compared to that of the wildtype. Most libraries were lower in affinity for c-Met, compared to the wild-type. The affinity for c-Met was retained in some mutants.

1.6. Selection of Antibody with Improved Affinity from Libraries

After maturation of the affinity of the constructed libraries for c-Met, the nucleotide sequence of scFv from each clone was analyzed. The nucleotide sequences thus obtained are summarized in Table 8 and were converted into IgG forms. Four antibodies which were respectively produced from clones L3-1, L3-2, L3-3, and L3-5 were used in the subsequent experiments.

TABLE 8

| Clone | Library constructed | CDR Sequence |
| --- | --- | --- |
| H11-4 | CDR-H1 | PEYYMS (SEQ ID NO: 22) |
| YC151 | CDR-H1 | PDYYMS (SEQ ID NO: 23) |
| YC193 | CDR-H1 | SDYYMS (SEQ ID NO: 24) |
| YC244 | CDR-H2 | RNNANGNT (SEQ ID NO: 25) |
| YC321 | CDR-H2 | RNKVNGYT (SEQ ID NO: 26) |
| YC354 | CDR-H3 | DNWLSY (SEQ ID NO: 27) |
| YC374 | CDR-H3 | DNWLTY (SEQ ID NO: 28) |
| L1-1 | CDR-L1 | KSSHSLLASGNQNNYLA (SEQ ID NO: 29) |
| L1-3 | CDR-L1 | KSSRSLLSSGNHKNYLA (SEQ ID NO: 30) |
| L1-4 | CDR-L1 | KSSKSLLASGNQNNYLA (SEQ ID NO: 31) |
| L1-12 | CDR-L1 | KSSRSLLASGNQNNYLA (SEQ ID NO: 32) |

TABLE 8 -continued

| Clone | Library constructed | CDR Sequence |
|---|---|---|
| L1-22 | CDR-L1 | KSSHSLLASGNQNNYLA (SEQ ID NO: 33) |
| L2-9 | CDR-L2 | WASKRVS (SEQ ID NO: 34) |
| L2-12 | CDR-L2 | WGSTRVS (SEQ ID NO: 35) |
| L2-16 | CDR-L2 | WGSTRVP (SEQ ID NO: 36) |
| L3-1 | CDR-L3 | QQSYSRPYT (SEQ ID NO: 13) |
| L3-2 | CDR-L3 | GQSYSRPLT (SEQ ID NO: 14) |
| L3-3 | CDR-L3 | AQSYSHPFS (SEQ ID NO: 15) |
| L3-5 | CDR-L3 | QQSYSRPFT (SEQ ID NO: 16) |
| L3-32 | CDR-L3 | QQSYSKPFT (SEQ ID NO: 37) |

1.7. Conversion of Selected Antibodies into IgG

Respective polynucleotides encoding heavy chains of the four selected antibodies were designed to have the structure of "EcoRI-signal sequence-VH-NheI—CH-XhoI" (SEQ ID NO: 38). The heavy chains of huAbF46 antibodies were used as they were because their amino acids were not changed during affinity maturation. In the case of the hinge region, however, the U6-HC7 hinge (SEQ ID NO: 57) was employed instead of the hinge of human IgG1. Genes were also designed to have the structure of "EcoRI-signal sequence-VL-BsiWI-CL-XhoI" for the light chain. Polypeptides encoding light chain variable regions of the four antibodies which were selected after the affinity maturation were synthesized in Bioneer. Then, a DNA fragment having the heavy chain nucleotide sequence (SEQ ID NO: 38) and DNA fragments having the light chain nucleotide sequences (DNA fragment including L3-1-derived CDR-L3: SEQ ID NO: 58, DNA fragment including L3-2-derived CDR-L3: SEQ ID NO: 59, DNA fragment including L3-3-derived CDR-L3: SEQ ID NO: 60, and DNA fragment including L3-5-derived CDR-L3: SEQ ID NO: 61) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen) and a pcDNA™ 3.3-TOPO TA Cloning Kit (Cat no. 8300-01), respectively, so as to construct recombinant vectors for expressing affinity-matured antibodies.

Each of the constructed vectors was amplified using Qiagen Maxiprep kit (Cat no. 12662), and a transient expression was performed using the Freestyle™ MAX 293 Expression System (invitrogen). 293 F cells were used for the expression and cultured in FreeStyle™ 293 Expression Medium in a suspension culture manner. One day prior to transient expression, the cells were suspended at a concentration of $5\times10^5$ cells/ml, and after 24 hours, when the cell number reached to $1\times10^6$ cells/ml, the transient expression was initiated. A transfection was performed by a liposomal reagent method using Freestyle™ MAX reagent (invitrogen), wherein the DNA was provided in the mixture ratio of 1:1 (heavy chain DNA:light chain DNA) in a 15 ml tube and mixed with 2 ml of OptiPro™ SFM (invtrogen) (A), and in another 15 ml tube, 100 ul (microliter) of Freestyle™ MAX reagent and 2 ml of OptiPro™ SFM were mixed (B), followed by mixing (A) and (B) together and incubating for 15 minutes. The obtained mixture was slowly mixed with the cells provided one day before the transient expression.

After completing the transfection, the cells were incubated in a 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify four affinity-matured antibodies (hereinafter referred to as "huAbF46-H4-A1 (L3-1 origin), huAbF46-H4-A2 (L3-2 origin), huAbF46-H4-A3 (L3-3 origin), and huAbF46-H4-A5 (L3-5 origin)," respectively).

1.8. Construction of Constant Region- and/or Hinge Region-Substituted huAbF46-H4-A1

Among the four antibodies selected in Reference Example 1.7, huAbF46-H4-A1 was found to be the highest in affinity for c-Met and the lowest in Akt phosphorylation and c-Met degradation degree. In the antibody, the hinge region, or the constant region and the hinge region, were substituted.

The antibody huAbF46-H4-A1 (U6-HC7) was composed of a heavy chain including the heavy chain variable region of huAbF46-H4-A1, U6-HC7 hinge, and the constant region of human IgG1 constant region, and a light chain including the light chain variable region of huAbF46-H4-A1 and human kappa constant region. The antibody huAbF46-H4-A1 (IgG2 hinge) was composed of a heavy chain including a heavy chain variable region, a human IgG2 hinge region, and a human IgG1 constant region, and a light chain including the light chain variable region of huAbF46-H4-A1 and a human kappa constant region. The antibody huAbF46-H4-A1 (IgG2 Fc) was composed of the heavy chain variable region of huAbF46-H4-A1, a human IgG2 hinge region, and a human IgG2 constant region, and a light chain including the light variable region of huAbF46-H4-A1 and a human kappa constant region. Hereupon, the histidine residue at position 36 on the human kappa constant region of the light chain was changed to tyrosine in all of the three antibodies to increase antibody production.

For use in constructing the three antibodies, a polynucleotide (SEQ ID NO: 63) encoding a polypeptide (SEQ ID NO: 62) composed of the heavy chain variable region of huAbF46-H4-A1, a U6-HC7 hinge region, and a human IgG1 constant region, a polynucleotide (SEQ ID NO: 65) encoding a polypeptide (SEQ ID NO: 64) composed of the heavy chain variable region of huAbF46-H4-A1, a human IgG2 hinge region, and a human IgG1 region, a polynucleotide (SEQ ID NO: 67) encoding a polypeptide (SEQ ID NO: 66) composed of the heavy chain variable region of huAbF46-H4-A1, a human IgG2 region, and a human IgG2 constant region, and a polynucleotide (SEQ ID NO: 69) encoding a polypeptide (SEQ ID NO: 68) composed of the light chain variable region of huAbF46-H4-A1, with a tyrosine residue instead of histidine at position 36, and a human kappa constant region were synthesized in Bioneer. Then, the DNA fragments having heavy chain nucleotide sequences were inserted into a pOptiVEC™-TOPO TA Cloning Kit enclosed in an OptiCHO™ Antibody Express Kit (Cat no. 12762-019, Invitrogen) while DNA fragments having light chain nucleotide sequences were inserted into a pcDNA™ 3.3-TOPO TA Cloning Kit (Cat no. 8300-01) so as to construct vectors for expressing the antibodies.

Each of the constructed vectors was amplified using Qiagen Maxiprep kit (Cat no. 12662), and a transient expression was performed using the Freestyle™ MAX 293 Expression System (invitrogen). 293 F cells were used for the expression and cultured in FreeStyle™ 293 Expression Medium in a suspension culture manner. One day prior to transient expression, the cells were suspended at a concentration of $5 \times 10^5$ cells/ml, and after 24 hours, when the cell number reached to $1 \times 10^6$ cells/ml, the transient expression was initiated. A transfection was performed by a liposomal reagent method using Freestyle™ MAX reagent (invitrogen), wherein the DNA was provided in the mixture ratio of 1:1 (heavy chain DNA:light chain DNA) in a 15 ml tube, and mixed with 2 ml of OptiPro™ SFM (invtrogen) (A), and in another 15 ml tube, 100 ul (microliter) of Freestyle™ MAX reagent and 2 ml of OptiPro™ SFM were mixed (B), followed by mixing (A) and (B) together and incubating for 15 minutes. The obtained mixture was slowly mixed with the cells provided one day prior to transient expression initiation. After completing the transfection, the cells were incubated in a 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with IgG elution buffer (Thermo Scientific, 21004). The buffer was exchanged with PBS to finally purify three antibodies (huAbF46-H4-A1 (U6-HC7), huAbF46-H4-A1 (IgG2 hinge), and huAbF46-H4-A1 (IgG2 Fc)). Among the three antibodies, huAbF46-H4-A1 (IgG2 Fc) was representatively selected for the following examples, and is referred to as SAIT301.

Reference Example 2

Production of Anti-Ang-2 Antibody 2.1. Production and Affinity of Phage-Derived Anti-Ang-2 Antibody 2.1.1. Production of Anti-Ang-2 Antibody Fully human Ang-2 antibodies were prepared against a human Ang-2 polypeptide (R&D Systems; Human Ang-2; Accession No. O15123 (hAng-2); SEQ ID NO: 84) using a phage display scFv library (obtained from the Ewha University Industry Academic Cooperation Foundation) according to the following protocol.

The Ang-2 polypeptide was plated at a concentration of about 10 µg/ml, about 1 µg/ml, and about 0.1 µg/ml into Maxisorp Immunotubes for the $1^{st}$ $2^{nd}$, and $3^{rd}$ rounds of panning through which antibodies to Ang-2 were enriched, respectively. In this regard, first, the surface of each immunotube was blocked with about 3% (v/v) milk in PBS. Separately, about $1 \times 10^{12}$ phage particles taken from the same phage display scFv library were blocked by incubation with about 0.5 ml of 3% (v/v) skim milk in PBS at 37° C. for 1 hr. Subsequently, the phages blocked with skim milk were added to Ang-2-plated immunotubes, followed by incubation at room temperature for 1 hr to allow the phages to bind to the Ang-2.

Thereafter, the phages were washed three to five times with PBS and about 0.1% (v/v) Tween 20 before eluting the bound phages with 100 mM triethanolamine. For use in the next screening step, the eluted phages were infected into and amplified in *E. coli* ER2537 cells (New England Biolabs, USA). This panning procedure was performed three times with the Ang-2 polypeptide plated at a concentration of about 10 µg/ml, about 1 µg/ml, and about 0.1 µg/ml into Maxisorp immunotubes. Approximately 600 Ang-2-bound scFv clones that recognized human Ang-2 (Accession No. O15123) and mouse Ang-2 (Accession No. NP_031452Ang-2Ang-2) were identified using ELISA (Enzyme-Linked ImmunoSorbent Assay) as described below.

2.1.2. Selection of Anti-Ang-2 Antibody-Producing Clones and Antibody Purification From approximately 600 Ang-2-bound scFv clones obtained in Reference Example 2.1.1, 70 clones producing an anti-Ang-2 antibody were selected on the basis of affinity for Ang-2 using an ELISA format. In detail, a selection was made of the clones with high ELISA OD values from Ang-2-bound clones able to inhibit interaction with Tie-2. Then, each of the selected clones was grown to the extent of $OD_{600}=1$ in an SB medium containing ampicillin. After induction with 1 mM IPTG (isopropyl-β-D-thiogalactopyranoside), periplasm fractions were harvested, and anti-Ang-2 monoclonal antibodies were partially purified from the fractions.

2.1.3. Anti-Ang-2 Human Antibody Gene Cloning

From each of the selected antibody-producing *E. coli* clones which were stored in respectively glycerol stocks, heavy chain and light chain variable region genes of the monoclonal antibody produced from each clone were amplified using a thermocycler (GeneAmp PCR System 9700, Applied Biosystems).

PCR Conditions:
94° C., 5 min;
30 cycles of 94° C., 1 min; 55°, 1 min; and 72° C., 2 min;
72° C., 6 min;
Cooling to 4° C.

```
Primers:
pC3X-f: 3'-GCACGACAGGTTTCCCGAC-5', pC3X-b: 3'-AACCATCGATAGCAGCACCG-5'.
```

The PCR products thus obtained were purified using a QIAquick Multiwell PCR Purification Kit (Qiagen) according to the manufacturer's instructions.

After being cloned, the PCR products were base sequenced using a well-known method. The CDR sequences were identified and are given in Tables 9 and 10.

Table 9 indicates amino acid sequences of heavy chain CDR of anti-Ang-2 antibodies, and Table 10 indicates amino acid sequences of light chain CDR of anti-Ang-2 antibodies.

TABLE 9

| | Heavy chain CDR | | |
|---|---|---|---|
| Antibody | CDRH1-KABAT | CDRH2-KABAT | CDRH3-KABAT |
| SAIT-ANG-2-AB-2-E6 | DYAMS (SEQ ID NO: 109) | AIYPDSGNKYYADSVKG (SEQ ID NO: 117) | ARHSSDPKVKSGYYDDGMDV (SEQ ID NO: 125) |

TABLE 9-continued

| | Heavy chain CDR | | |
|---|---|---|---|
| Antibody | CDRH1-KABAT | CDRH2-KABAT | CDRH3-KABAT |
| SAIT-ANG-2-AB-8-A5 | DYYMS (SEQ ID NO: 110) | GIYPSGGSTYYADSVKG (SEQ ID NO: 118) | ARDPSTLTYAGFDY (SEQ ID NO: 126) |
| SAIT-ANG-2-AB-7-C9 | NYAMS (SEQ ID NO: 111) | AISSGGGNIYYADSVKG (SEQ ID NO: 119) | AKSGIQPSPPSMSSAYAMDV (SEQ ID NO: 127) |
| SAIT-ANG-2-AB-4-C11 | DYAMS (SEQ ID NO: 112) | SIYPDDGNTYYADSVKG (SEQ ID NO: 120) | ARHTSHHTSIDGYYYYGMDG (SEQ ID NO: 128) |
| SAIT-ANG-2-AB-4-F5 | DYDMS (SEQ ID NO: 113) | SISHGDSNKYYADSVKG (SEQ ID NO: 121) | AKSSGIQESPPTYYYYGMDV (SEQ ID NO: 129) |
| SAIT-ANG-2-AB-4-F11 | DYAMS (SEQ ID NO: 114) | SIYPDDGNTYYADSVKG (SEQ ID NO: 122) | AKHPVRLNLHPMYYYYGMDV (SEQ ID NO: 130) |
| SAIT-ANG-2-AB-4-H10 | SYDMS (SEQ ID NO: 115) | LISPDSSSIYYADSVKG (SEQ ID NO: 123) | AKDLISFWRGGFDY (SEQ ID NO: 131) |
| SAIT-ANG-2-AB-3-D3 | DYDMS (SEQ ID NO: 116) | GISSDDGNTYYADSVKG (SEQ ID NO: 124) | ARPTIDKYTLRGYYSYGMDV (SEQ ID NO: 132) |

TABLE 10

| | Light chain CDR | | |
|---|---|---|---|
| Antibody | CDRL1-KABAT | CDRL2-KABAT | CDRL3-KABAT |
| SAIT-ANG-2-AB-2-E6 | SGSSSNIGNNAVN (SEQ ID NO: 133) | ADSNRPS (SEQ ID NO: 141) | GSWDYSLSG (SEQ ID NO: 149) |
| SAIT-ANG-2-AB-8-A5 | SGSSSNIGNNYVT (SEQ ID NO: 134) | ADSHRPS (SEQ ID NO: 142) | ATWDYSLSG (SEQ ID NO: 150) |
| SAIT-ANG-2-AB-7-C9 | SGSSSNIGNNDVY (SEQ ID NO: 135) | ANSHRPS (SEQ ID NO: 143) | GTWDYSLSG (SEQ ID NO: 151) |
| SAIT-ANG-2-AB-4-C11 | TGSSSNIGNNDVS (SEQ ID NO: 136) | SDSKRPS (SEQ ID NO: 144) | GSWDYSLSG (SEQ ID NO: 152) |
| SAIT-ANG-2-AB-4-F5 | SGSSSNIGNNAVN (SEQ ID NO: 137) | ADSNRPS (SEQ ID NO: 145) | GSWDYSLSG (SEQ ID NO: 153) |
| SAIT-ANG-2-AB-4-F11 | TGSSSNIGNNAVS (SEQ ID NO: 138) | SDSQRPS (SEQ ID NO: 146) | ATWDYSLSA (SEQ ID NO: 154) |
| SAIT-ANG-2-AB-4-H10 | SGSSSNIGSNYVN (SEQ ID NO: 139) | SDSHRPS (SEQ ID NO: 147) | GAWDDSLSG (SEQ ID NO: 155) |
| SAIT-ANG-2-AB-3-D3 | TGSSSNIGSNYVS (SEQ ID NO: 140) | SDNKRPS (SEQ ID NO: 148) | GTWDDSLNG (SEQ ID NO: 156) |

2.1.4. Expression and Purification of Complete Antibody

The heavy chain and light chain variable regions (refer to Table 11, below) obtained in Reference Example 2.1.3 were cloned into respective vectors. The heavy chain variable regions were inserted into the pOPTI-VAC vector (Invitrogen) having a CMV (cytomegalovirus) promoter, and the constant region and Fc region of human IgG1. For the light chain variable regions, the pFUSE2-CLIg-h12 vector (InvivoGen) having a constant region of human IgG1 was employed.

In detail, the heavy chains and their vectors were treated with the restriction enzymes EcoRI (NEB) and NheI (NEB), while the light chains and their vectors were treated with the restriction enzymes EcoRI (NEB) and AvrII (NEB), followed by ligating the chains to their vectors in the presence of T4 DNA ligase (New England Biolabs) to construct recombinant expression vectors carrying desired heavy chain or light chain variable regions of human antibodies.

The heavy chain vectors and the light chain vectors were co-transfected into 293-F cells (Invitrogen) which were then cultured at 37° C. in a serum-free 293-f expression medium (Invitrogen). The culture media were collected at day 5 after transfection, and were found to contain human antibodies composed of heavy chains and light chains having the variable region sequences given in Tables 9 and 10, as analyzed by SDS-PAGE. After removing cell debris and impurities from the culture media by centrifugation at 1000×g for 10 min, antibodies were purified by affinity chromatography using protein A (GE-Healthcare) with high affinity to the Fc region.

Base sequences of the heavy chain and light chain variable regions of the purified antibodies were analyzed, and are given in Table 11, below. Note that letters in bold in each cell represent CDR1, CDR2, and CDR3 respectively, in the order.

| Antibody | Amino acid sequence of heavy chain variable region | Amino acid sequence of light chain variable region |
| --- | --- | --- |
| SAIT-ANG-2-AB-2-E6 | EVQLLESGGGLVQTGGSLRL SCAASGFTFSDYAMSWVRQA PGKGLEWVSAIYPDSGNKYY ADSVKGRFTISRDNSKNTLYL QMNSLRAEDTAVYYCARHSS DPKVKSGYYDDGMDVWGQG TLVAVSS (SEQ ID NO: 162) | QSVLTQPPSASGTPGQRVTIS CSGSSSNIGNNAVNWYQQLP GTAPKLLIYADSNRPSGVPDR FSGSKSGTSASLAISGLRSED EADYYCGSWDYSLSGYVFG GGTKLTVLG (SEQ ID NO: 170) |
| SAIT-ANG-2-AB-8-A5 | EVQLLESGGGLVQPGGSLRL SCAASGFTFSDYYMSWVRQA PGKGLEWVSGIYPSGGSTYY ADSVKGRFTISRDNSKNTLYL QMNSLRAEDTAVYYCARDPS TLTYAGFDYWGQGTLVTVSS (SEQ ID NO: 163) | QSVLTQPPSASGTPGQRVTIS CSGSSSNIGNNYVTWYQQLP GTAPKLLIYADSHRPSGVPDR FSGSKSGTSASLAISGLRSED EADYYCATWDYSLSGYVFG GGTKLTVLG (SEQ ID NO: 171) |
| SAIT-ANG-2-AB-7-C9 | EVQLLESGGGLVQPGGSLRL SCAASGFTFSNYAMSWVRQA PGKGLEWVSAISSGGGNIYYA DSVKGRFTISRDNSKNTLYLQ MNSLRAEDTAVYYCAKSGIQ PSPPSMSSAYAMDVWGQGT LVTVSS (SEQ ID NO: 164) | QSVLTQPPSASGTPGQRVTIS CSGSSSNIGNNDVYWYQQLP GTAPKLLIYANSHRPSGVPDR FSGSKSGTSASLAISGLRSED EADYYCGTWDYSLSGYVFG GGTKLTVLG (SEQ ID NO: 172) |
| SAIT-ANG-2-AB-4-C11 | EVQLLESGGGLVQPGGSLRL SCAASGFTFSDYAMSWVRQA PGKGLEWVSSIYPDDGNTYY ADSVKGRFTISRDNSKNTLYL QMNSLRAEDTAVYYCARHTS HHTSIDGYYYYGMDGWGQG TLVTVSS (SEQ ID NO: 165) | QSVLTQPPSASGTPGQRVTIS CTGSSSNIGNNDVSWYQQLP GTAPKLLIYSDSKRPSGVPDR FSGSKSGTSASLAISGLRSED EADYYCGSWDYSLSGYVFG GGTKLTVLG (SEQ ID NO: 173) |
| SAIT-ANG-2-AB-4-F5 | EVQLLESGGGLVQPGGSLRL SCAASGFTFSDYDMSWVRQA PGKGLEWVSSISHGDSNKYY ADSVKGRFTISRDNSKNTLYL QMNSLRAEDTAVYYCAKSSG IQESPPTYYYYGMDVWGQGT LVTVSS (SEQ ID NO: 166) | QSVLTQPPSASGTPGQRVTIS CSGSSSNIGSNAVNWYQQLP GTAPKLLIYADSNRPSGVPDR FSGSKSGTSASLAISGLRSED EADYYCGSWDYSLSGYVFG GGTKLTVLG (SEQ ID NO: 174) |
| SAIT-ANG-2-AB-4-F11 | EVQLLESGGGLVQTGGSLRL SCAASGFTFSDYAMSWVRQA PGKGLEWVSSIYPDDGNTYY ADSVKGRFTISRDNSKNTLYL QMNSLRAEDTAVYYCAKHPV RLNLHPMYYYYGMDVWGQG TLVTVSS (SEQ ID NO: 167) | QSVLTQPPSASGTPGQRVTIS CTGSSSNIGNNAVSVVYQQLP GTAPKLLIYSDSQRPSGVPDR FSGSKSGTSASLAISGLRSED EADYYCATWDYSLSAYVFGG GTKLTVLG (SEQ ID NO: 175) |
| SAIT-ANG-2-AB-4-H10 | EVQLLESGGGLVQPGGSLRL SCAASGFTFSSYDMSWVRQA PGKGLEWVSLISPDSSSIYYA DSVKGRFTISRDNSKNTLYLQ MNSLRAEDTAVYYCAKDLISF WRGGFDYWGQGTLVTVSS (SEQ ID NO: 168) | QSVLTQPPSASGTPGQRVTIS CSGSSSNIGSNYVNWYQQLP GTAPKLLIYSDSHRPSGVPDR FSGSKSGTSASLAISGLRSED EADYYCGAWDDSLSGYVFG GGTKLTVLG (SEQ ID NO: 176) |
| SAIT-ANG-2-AB-3-D3 | EVQLLESGGGLVQPGGSLRL SCAASGFTFSDYDMSWVRQA PGKGLEWVSGISSDDGNTYY ADSVKGRFTISRDNSKNTLYL QMNSLRAEDTAVYYCARPTID KYTLRGYYSYGMDVWGQG LVTVSS (SEQ ID NO: 169) | QSVLTQPPSASGTPGQRVTIS CTGSSSNIGSNYVSWYQQLP GTAPKLLIYSDNKRPSGVPDR FSGSKSGTSASLAISGLRSED EADYYCGTWDDSLNGYVFG GGTKLTVLG (SEQ ID NO: 177) |

2.2. Production and Affinity of Mice-Derived Anti-Ang-2 Antibody

2.2.1. Production of Anti-Ang-2 antibody

In order to produce anti-Ang-2 antibodies, human Ang-2 protein (R&D Systems) was administered, together with an adjuvant, into 5-week-old BALB/c mice to induce an immune response, and the mice were used to construct hybridomas producing monoclonal antibodies according to the method of Schwaber et al. (Schwaber, J. and Cohen, E. P., "Human×Mouse Somatic Cell Hybrid Clones Secreting Immunoglobulins of Both Parental Types," Nature, 244 (1973), 444-447).

Mice were sufficiently immunized to develop a hybridoma cell line. In this regard, first, human Ang-2 protein (R&D Systems) was intraperitoneally injected at a dose of 100 μg/mouse, together with complete Freund's adjuvant in the same amount, into 5 BALB/c mice (Japan SLC, Inc.) with an age of 4~6 weeks. After two weeks, the antigen (half of the primary dose) in combination with an incomplete Freund's adjuvant was administered into the mice by intraperitoneal injection. A final booster injection was administered one week after the second injection. Three days later, blood was taken from the tail, and the sera were 1/1000 diluted in PBS and used to measure titers of antibodies to Ang-1 using ELISA. Mice with high antibody titers were selected to conduct cell fusion.

Three days before a cell fusion experiment, 100 μg of human Ang-2 protein (R&D systems) in 50 μg of PBS was intraperitoneally injected into the BALB/c mice (Japan SLC, Inc.). After the immunized mice were anesthetized, the spleen was excised from the left side of the body, and ground through a mesh to separate cells. The homogenates were suspended in a culture medium (DMEM, HyClone), followed by centrifugation to form a cell layer. The splenocytes thus obtained were mixed at a population of $1 \times 10^8$ cells with $1 \times 10^7$ myeloma (Sp2/0) cells, and centrifuged. A resultant cell pellet was slowly dispersed, incubated at 37° C. for 1 min with 1 ml of 45% polyethylene glycol (PEG 1500) in a culture medium (DMEM), and added with 1 ml of a culture medium (DMEM). Subsequently, 10 ml of a culture medium (DMEM) was added to the dispersion over 1 min which was then incubated at 37° C. for 5 min in water and diluted to a total volume of 50 ml before centrifugation. The cell pellets were resuspended at a density of $1\sim2 \times 10^5$ cells/ml in a selective medium (HAT medium), plated in a volume of 0.1 ml/well into 96-well plates, and grown in a 37° C. $CO_2$ incubator to form hybridoma cell lines.

2.2.2. Selection of Anti-Ang-2 Antibody Producing Clones and Purification of Antibody From the antibody-producing hybridomas, 95 hybridomas which produced anti-Ang-2 monoclonal antibodies were selected on the basis of affinity for Amg-2 using a typical ELISA format.

In this regard, the hybridoma cell lines prepared in Reference Example 2.2.1 were screened for specific affinity for Ang-2 by ELISA using the Ang-2 protein as an antigen.

Human Ang-2 was added at a concentration of 100 ng/well to microtiter plates and allowed to adhere to the surface of the plates. The plates were washed to remove the antigen that remained non-adherent. Then, 50 μl of the hybridoma cell culture of Reference Example 2.2.1 was added to each well and incubated for 1 hr, followed by washing the plates with a sufficient volume of phosphate buffered saline-Tween 20 (TBST) to remove proteins that remained unbound. The plates were reacted with the secondary antibody goat anti-mouse IgG-HRP (horseradish peroxidase) at room temperature for 1 hr, and washed sufficiently with TBST. A substrate for peroxidase (OPD) was added to the plates, and absorbance at 450 nm was read using an ELISA reader to select hybridoma cell lines that produced antibodies with high selective affinity for human Ang-2 protein. The hybridoma cell lines selected were recloned by limiting dilution to finally establish 58 clones producing monoclonal antibodies.

After each of the established hybridomas was cultured in DMEM (Dulbecco's Modified Eagle's Medium), anti-Ang-2 monoclonal antibodies were purified from the cell culture using protein G-affinity chromatography.

First, the hybridoma cells grown in 50 ml of culture medium (DMEM) supplemented with 10% (v/v) FBS were separated as pellets by centrifugation, and the cell pellets were washed two or more times with 20 ml of PBS to remove FBS. Then, the cells were resuspended in 50 ml of DMEM and incubated for 3 days in a 37° C. $CO_2$ incubator. The culture medium into which the antibodies were secreted was separated from the cells by centrifugation, and stored at 4° C. until use or were immediately used. In this case, antibodies were purified from 50 to 300 ml of the culture medium using a AKTA purification system (GE Healthcare) equipped with an affinity column (protein G agarose column; Pharmacia, USA), and the purified antibodies were concentrated via centrifugation using a filter (Amicon) and incubated in PBS before storage until a subsequent experiment.

2.2.3. Assay for Inhibitory Activity Against Ang-2:Tie-2 Binding

To examine whether the Ang-2 antibodies prepared in Reference Example 2.2.2 served as neutralization antibodies inhibitory of the binding of Ang-2 to Tie-2, an Ang-2:Tie-2 binding competition ELISA was conducted.

A 96-well MaxiSorp™ flat-bottom plate (Nunc) was coated with 4 μg/ml hTie-2-Fc (R&D Systems, Inc.), a recombinant protein in which Tie-2 is fused with the Fc of human IgG1. Then, the plates were washed five times with 0.05% (v/v) Tween-20 in PBS, and blocked at room temperature for 2 hrs with 1% (v/v) BSA (bovine serum albumin; Sigma) in PBS.

For Ang-2:Tie-2 competition ELISA, each of the anti-Ang-2 antibodies prepared in Reference Example 2.2.2 was added at various concentrations of from about 400 nM to about 0.01 nM, together with 1% (v/v) BSA and 400 ng/ml FLAG-tagged hAng-2, to each well coated with the hTie-2/Fc fusion protein, followed by incubation at room temperature for 2 hrs. The plates were washed 5 times with PBST. An HRP-conjugated anti-FLAG antibody (Sigma) was diluted 1:5,000 in PBS containing 1% (v/v) BSA, and the dilution was added in an amount of 100 μl to each well and reacted at room temperature for 1 hr, after which the plates were washed five times with PBST. Subsequently, color development was induced with 100 μl of a TMB substrate (Cell Signaling) in each well for 3 min before adding 100 μl of a stop buffer (Cell Signaling) to each well. Optical density at 450 nm ($OD_{450}$) values were measured on a plate reader (Molecular Devices).

From the measurements, 50% inhibition concentrations ($IC_{50}$) of the antibodies against angiopoietin-2:Tie-2 binding were determined, indicating that the anti-Ang-2 antibodies are able to neutralize the binding of Ang-2 to Tie-2. The results are summarized in Table 12, below.

TABLE 12

| Antibody | 50% Inhibition concentration against Ang-2: Tie-2 binding ($IC_{50}$, nM) |
|---|---|
| SAIT-ANG-2-AB-m1A10 | 1.34 |
| SAIT-ANG-2-AB-m1B6 | 2.89 |
| SAIT-ANG-2-AB-m3E2 | 0.55 |
| SAIT-ANG-2-AB-m8D3 | 0.99 |

2.2.4. Affinity Measurement of Anti-Ang-2 Antibody to hAng-2, and hAng-1

The anti-Ang-2 antibodies were assayed for affinity for antigens using BIAcore T100, a surface plasmon resonance (SPR) device (GE Healthcare). The SPR device takes advantage of the phenomenon that light traveling on a chip on the surface of a metal varies in reflectivity depending on the condition of the chip, that is, a matter applied to the chip. When an antigen or antibody is applied to a chip coated with a corresponding antibody or antigen, the light incident on the surface of the metal is reflected at different angles. From these changes, Kd between the antigen and the antibody can be calculated.

An anti-His antibody was immobilized to the degree of 8,000 response units (RU) on a CM5 sensor chip (GE Healthcare) using a pH 5.0 acetate solution and an amine coupling kit (GE Healthcare). Recombinant hAng-2 protein (C-His, R&D Systems) was flowed into this immobilized antibody at a concentration of 6 μg/ml to capture the antibody at 100~200 RU. In this regard, the antibodies obtained in Reference Example 2.2.2 were serially diluted by half each time starting from 100 nM before application. Then, the antigen/antibody affinity was measured by binding each antibody with the antigen captured by the sensor chip (on) and dissociating the antibody from the antigen (off) (using 10 mM NaOH). Kd values were calculated from the measurements. The same experiment was conducted with hAng-1. The results are given in Table 13, below.

TABLE 13

| Antibody | hAng-2 (Kd, nM) | hAng-1 (Kd, nM) |
|---|---|---|
| SAIT-ANG-2-AB-m1A10 | 4.2 | No binding |
| SAIT-ANG-2-AB-m1B6 | 2.3 | No binding |
| SAIT-ANG-2-AB-m3E2 | 1.3 | No binding |
| SAIT-ANG-2-AB-m8D3 | 4.0 | No binding |

2.2.5. Gene Cloning of Anti-Ang-2 Antibody

From each of the antibody-producing hybridomas ($2 \times 10^6$ cells), total RNA was isolated using an RNeasy mini kit (Qiagen). While the total RNA served as a template, gene coding for heavy chain and light chain variable regions of the monoclonal antibody produced from each hybridoma were amplified using a OneStep RT-PCR kit (Qiagen) and a Mouse Ig-Primer Set (Novagen) in a thermocycler (GeneAmp PCR System 9700, Applied Biosystems) according to the following programs: 94° C., 5 min; [50° C., 30 min, 95° C., 15 min], 35 cycles of [94° C., 1 min, 50° C., 1 min, 72° C., 2 min]; 72° C., 6 min; cooling to 4° C.

Base sequencing analysis was performed on each of the resulting PCR products to identify a CDR sequence, a heavy chain variable region, and a light chain variable region for each antibody. CDR sequences, heavy chain variable regions, and light chain variable regions of the antibodies are shown in Tables 14 (heavy chain CDR), 15 (light chain CDR), and 16 (heavy chain and light chain variable regions).

TABLE 14

| | Heavy chain CDR | | |
|---|---|---|---|
| Antibody | CDRH1-KABAT | CDRH2-KABAT | CDRH3-KABAT |
| SAIT-ANG-2-AB-m1A10 | SYWLE (SEQ ID NO: 178) | EILPGSGSTNYN EKFRG (SEQ ID NO: 182) | GNHNSYYYAMDY (SEQ ID NO: 186) |
| SAIT-ANG-2-AB-m3E2 | DPYIH (SEQ ID NO: 179) | RIDPANGNTKYD PKFQG (SEQ ID NO: 183) | RWDGGGFDY (SEQ ID NO: 187) |
| SAIT-ANG-2-AB-m8D3 | DYYMK (SEQ ID NO: 180) | EINPKNGDTFYN QIFKG (SEQ ID NO: 184) | ENDYDVGFFDY (SEQ ID NO: 188) |
| SAIT-ANG-m2-AB-1B6 | NYGMN (SEQ ID NO: 181) | WINTYTGEPTYA DDFKG (SEQ ID NO: 185) | DHDGYLMDY (SEQ ID NO: 189) |

TABLE 15

| | Light chain CDR | | |
|---|---|---|---|
| Antibody | CDRL1-KABAT | CDRL2-KABAT | CDRL3-KABAT |
| SAIT-ANG-2-AB-m1A10 | RASESVDSYGNS FMH (SEQ ID NO: 190) | RASNLDS (SEQ ID NO: 194) | QQSNEDPLT (SEQ ID NO: 198) |
| SAIT-ANG-2-AB-m3E2 | RASQDISNYLN (SEQ ID NO: 191) | YTSRLHS (SEQ ID NO: 195) | QQGNTLPWT (SEQ ID NO: 199) |
| SAIT-ANG-2-AB-m8D3 | KASQSVSNDVA (SEQ ID NO: 192) | YASNRYP (SEQ ID NO: 196) | QQDYTSPWT (SEQ ID NO: 200) |
| SAIT-ANG-2-AB-m1B6 | STSQGISNYLN (SEQ ID NO: 193) | YTSSLHS (SEQ ID NO: 197) | QQYSKLPYT (SEQ ID NO: 201) |

TABLE 16

| | Amino acid sequence of heavy chain variable region | Amino acid sequence of light chain variable region |
|---|---|---|
| SAIT-ANG-2-AB-m1A10 | QVQLQQSGAELMKPGASVKISCKAT DYTFSSYWLEWLIQRPGHGLEWIGE ILPGSGSTNYNEKFRGKATFTEDTS SNTAYMQLSSLTSEDSAVYYCARG NHNSYYYAMDYWGQGTSVTVSS (SEQ ID NO: 204) | DIVLTQSPASLAVSLGQRATISCRAS ESVDSYGNSFMHWYQQKPGQPPK LLIYRASNLDSGIPARFSGSGSRTDF TLTINPVEADDVATYYCQQSNEDPL TFGAGTKLELK (SEQ ID NO: 205) |
| SAIT-ANG-2-AB-m3E2 | EVQLQQSGAELVKPGASVKLSCTAS GFNIKDPYIHWVKQRPEQGLEWIGR IDPANGNTKYDPKFQGKATITADTSS NTAYLQLSSLTSEDTAVYYCVRRWD GGGFDYWGQGTSVTVSS (SEQ ID NO: 206) | DIQMTQTTSSLSASLGDRVTISCRAS QDISNYLNWYQQKPDGTVKLLIYYT SRLHSGVPSRFSGSGSGTDYSLTIT NLEQEDIATYFCQQGNTLPWTFGG GTKLEIK (SEQ ID NO: 207) |
| SAIT-ANG-2-AB-m8D3 | EVQLQQSGPELVKPGDSVKMSCKA SGYTFTDYYMKWVRQSHGKSLQW VGEINPKNGDTFYNQIFKGKATLTVD KSSSTAYMQLTSLTSEDSAVYYCTR ENDYDVGFFDYWGQGTSVTVSS (SEQ ID NO: 208) | TIVMTQTPKFLLVSAGDRITITCKASQ SVSNDVAWYQQKPGQSPKLLIYYAS NRYPGVPDRFTGSGYGTDFTFTIST VQAEDLAVYFCQQDYTSPWTFGGG TELEIK (SEQ ID NO: 209) |
| SAIT-ANG-2-AB- | QIQLVQSGPELKKPGETVKISCKAS GYTFTNYGMNWVKQAPGKGLKWM GWINTYTGEPTYADDFKGRFAFSLE | DIQMTQTTSSLSASLGDRVTISCSTS QGISNYLNWYQQKPDGTVKLLIFYT SSLHSGVPSRFSGSGSGTDYSLTIS |

TABLE 16-continued

| | Amino acid sequence of heavy chain variable region | Amino acid sequence of light chain variable region |
|---|---|---|
| m1B6 | TSASTAYLQINNLKNEDTATYFCARD HDGYLMDYWGQGTSVTVSS (SEQ ID NO: 210) | NLEPEDIATYYCQQYSKLPYTFGGG TKLEIK (SEQ ID NO: 211) |

Example 1

Inhibitory Effect of Combination Therapy of Anti-c-Met Antibody and Anti-Ang-2 Antibody on Cancer Cell Growth To examine whether a combination therapy of an anti-Ang-2 antibody (SAIT-ANG-2-AB-4-H10; Tables 9-11) and an anti-c-Met antibody (SAIT301) inhibits the growth of cancer cells, a real-time cell analysis was carried out using an xCelligence system (Roche). In the analyzer xCelligence-RTCA DP system, cells adhering to gold microelectrode sensors lead to an increase in impedance, which is measured in real time by the instrument to count cells. For real-time cell monitoring, an E-plate 16 was employed. Cells (HuVEC, Lonza) were added at a density of 5,000 cells/well, together with the antibody mixture, to the E-plate 16. A cell index profile was drawn from relative impedance measurements read when cells adhered to the bottom, and is given in FIG. 1. In this experiment, respective inhibitors, when used alone or in combination, were analyzed for inhibitory activity against the growth of the cells grown in the presence of 2 g/ml Ang-2 100 ng/ml HG/SF, a ligand for c-Met.

As shown in FIG. 1, the anti-Ang-2 antibody and the anti-c-Met antibody were found to inhibit the growth of cancer cells significantly more effectively when used in combination than alone.

Example 2

Inhibitory Effect of Combination Therapy of Anti-c-Met Antibody and Anti-Ang-2 Antibody on Angiogenesis Through Inhibition of Migration of Vascular and Lymphatic Endothelial Cells The migration of vascular and lymphatic endothelial cells was analyzed using an xCelligence RTCA (real-time cell analyzer, GE Healthcare). The RTCA is a non-invasive cell monitoring system capable of detecting cell responses in real time on the basis of an impedance change. For a cell migration assay, a CIM-plate 16 composed of a lower chamber and an upper chamber (GE Healthcare) was employed. The CIM-plate 16 is designed to have an array of microelectrodes in the upper chamber and to detect a change in impedance which occurs when cells, after seeded, adhere to the electrodes during migration through the micropores. A migration index was obtained from the impedance measurements. Vascular and lymphatic endothelial cells (P3-7) grown in an EGM2 medium were maintained for 6 hrs in an EBM medium supplemented with 1% FBS. After a low-serum FBS-supplemented EBM medium containing 200 ng HGF and 2 µg/ml Ang-2 (R&D Systems) was added, together with SAIT301 and anti-Ang-2, to each well of the lower chamber of CIM-plate 16, the lower chamber was assembled with the upper chamber coated with fibronectin. A serum-free medium was added in an amount of 30 µl/well to the upper chamber, followed by incubation for 1 hr in an incubator to equilibrate the plate with the medium. The CIM-plate was mounted to the device station of the incubator to measure a background value. Vascular and lymphatic endothelial cells resuspended in a serum-free medium was seeded at a density of 40,000 cells/well, left for 15 min to settle, and mounted to the instrument. Cell migration was measured in real time as a cell index. The measurements are shown as migration indices in FIGS. 2 and 3.

Figure 2:
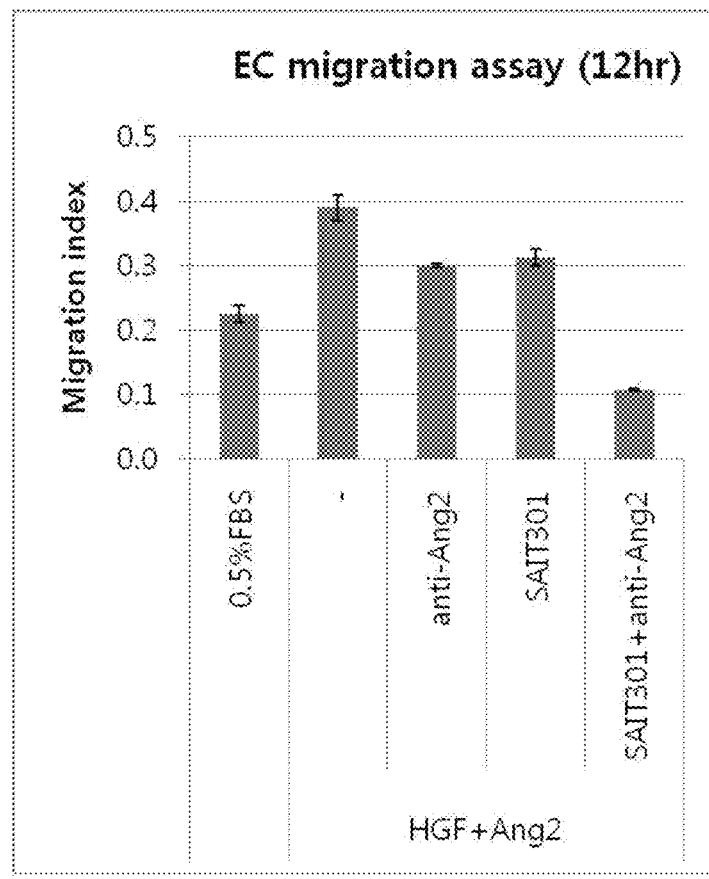
FIG. 2 is a graph of the migration index of cells after exposure to specified agents showing inhibitory activities of an anti-c-Met antibody (SAIT301) and an anti-Ang-2 antibody (SAIT-ANG-2-AB-4-H10), when administered alone or in combination, against the migration of vascular endothelial cells, as measured by real-time cell analysis.
Figure 3:
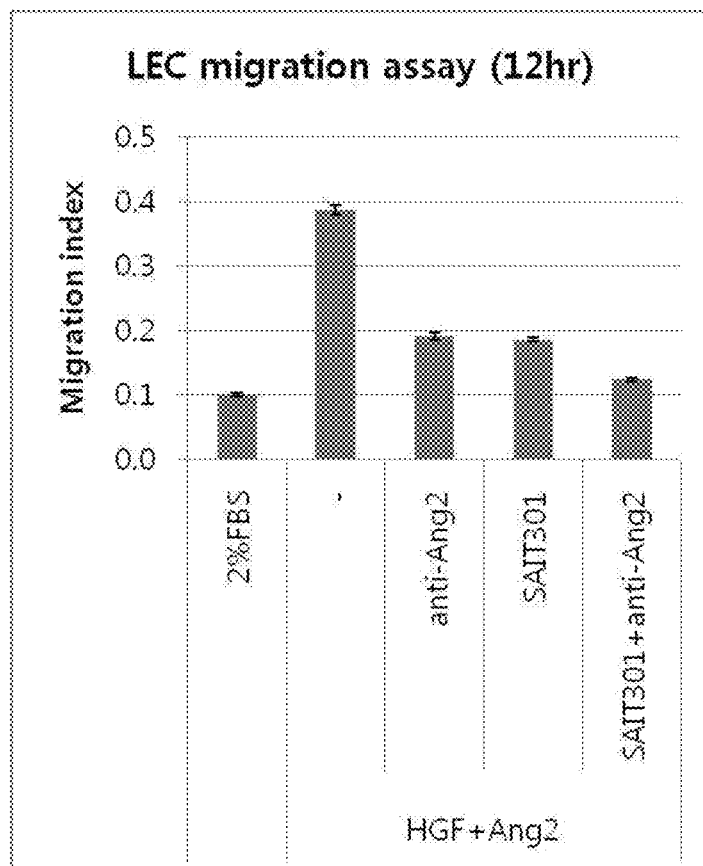
FIG. 3 is a graph of the migration index of cells after exposure to specified agents showing inhibitory activities of an anti-c-Met antibody (SAIT301) and an anti-Ang-2 antibody (SAIT-ANG-2-AB-4-H10), when administered alone or in combination, against the migration of lymphatic endothelial cells, as measured by real-time cell analysis.

As is understood from data of FIGS. 2 and 3, the anti-Ang-2 antibody and the anti-c-Met antibody inhibited the migration of vascular and lymphatic endothelial cells to a greater extent when used in combination than alone.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for inhibiting angiogenesis comprising administering to a subject an anti-c-Met antibody or an antigen-binding fragment thereof, and an anti-Ang-2 antibody or an antigen-binding fragment thereof, in combination simultaneously or sequentially, wherein the anti-c-Met antibody or the antigen-binding fragment thereof comprises a heavy chain variable region comprising a CDR-H1, a CDR-H2, and a CDR-H3, and a light chain variable region comprising a CDR-L1, a CDR-L2, and a CDR-L3, and wherein:

the CDR-H1 has the amino acid sequence of SEQ ID NO: 1,
the CDR-H2 has the amino acid sequence of SEQ ID NO: 2,
the CDR-H3 has the amino acid sequence of SEQ ID NO: 3,
the CDR-L1 has the amino acid sequence of SEQ ID NO: 10,
the CDR-L2 has the amino acid sequence of SEQ ID NO: 11, and
the CDR-L3 has the amino acid sequence of SEQ ID NO: 13, and wherein the anti-Ang-2 antibody or the antigen-binding fragment thereof comprises:

a CDR-H1 having the amino acid sequence of SEQ ID NO: 109, a CDR-H2 having the amino acid sequence of SEQ ID NO: 117, and a CDR-H3 having the amino acid sequence of SEQ ID NO: 125, a CDR-L1 having the amino acid sequence of SEQ ID NO: 133, a CDR-L2 having the amino acid sequence of SEQ ID NOs: 141, and a CDR-L3 having the amino acid sequence of SEQ ID NO: 149;

a CDR-H1 having the amino acid sequence of SEQ ID NO: 110, a CDR-H2 having the amino acid sequence of SEQ ID NO: 118, a CDR-H3 having the amino acid sequence of SEQ ID NO: 126, a CDR-L1 having the amino acid sequence of SEQ ID NO: 134, a CDR-L2 having the amino acid sequence of SEQ ID NO: 142, and a CDR-L3 having the n amino acid sequence of SEQ ID NO: 150;

a CDR-H1 having the amino acid sequence of SEQ ID NO: 111, a CDR-H2 having the amino acid sequence of SEQ ID NO: 119, a CDR-H3 having the amino acid sequence of SEQ ID NO: 127, a CDR-L1 having the amino acid sequence of SEQ ID NO: 135, a CDR-L2 having the amino acid sequence of SEQ ID NO: 143, and a CDR-L3 having the amino acid sequence of SEQ ID NO: 151;

a CDR-H1 having the amino acid sequence of SEQ ID NO: 112, a CDR-H2 having the amino acid sequence of SEQ ID NO: 120, a CDR-H3 having the amino acid sequence of SEQ ID NO: 128, a CDR-L1 having the amino acid sequence of SEQ ID NO: 136, a CDR-L2 having the amino acid sequence of SEQ ID NO: 144, and a CDR-L3 having the amino acid sequence of SEQ ID NO: 152;

a CDR-H1 having the amino acid sequence of SEQ ID NO: 113, a CDR-H2 having the amino acid sequence of SEQ ID NO: 121, a CDR-H3 having the amino acid sequence of SEQ ID NO: 129, a CDR-L1 having the amino acid sequence of SEQ ID NO: 137, a CDR-L2 having the amino acid sequence of SEQ ID NO: 145, and a CDR-L3 having the amino acid sequence of SEQ ID NO: 153;

a CDR-H1 having the amino acid sequence of SEQ ID NO: 114, a CDR-H2 having the amino acid sequence of SEQ ID NO: 122, a CDR-H3 having the amino acid sequence of SEQ ID NO: 130, a CDR-L1 having the amino acid sequence of SEQ ID NO: 138, a CDR-L2 having the amino acid sequence of SEQ ID NO: 146, and a CDR-L3 having the amino acid sequence of SEQ ID NO: 154;

a CDR-H1 having the amino acid sequence of SEQ ID NO: 115, a CDR-H2 having the amino acid sequence of SEQ ID NO: 123, a CDR-H3 having the amino acid sequence of SEQ ID NO: 131, a CDR-L1 having the amino acid sequence of SEQ ID NO: 139, a CDR-L2 having the amino acid sequence of SEQ ID NO: 147, and a CDR-L3 having the amino acid sequence of SEQ ID NO: 155; or a CDR-H1 having the amino acid sequence of SEQ ID NO: 116, a CDR-H2 having the amino acid sequence of SEQ ID NO: 124, a CDR-H3 having the amino acid sequence of SEQ ID NO: 132, a CDR-L1 having the amino acid sequence of SEQ ID NO: 140, a CDR-L2 having the amino acid sequence of SEQ ID NO: 148, and a CDR-L3 having the amino acid sequence of SEQ ID NO: 156.

2. The method according to claim 1, wherein
the heavy chain variable region of the anti-c-Met antibody or fragment thereof has the amino acid sequence of SEQ ID NO: 17, and
the light chain variable region of the anti-c-Met antibody or fragment thereof has the amino acid sequence of SEQ ID NO: 212, or SEQ ID NO: 18.

3. The method according to claim 1, wherein the anti-c-Met antibody or the antigen-binding fragment thereof comprises:

a heavy chain having the amino acid sequence of SEQ ID NO: 62, the amino acid sequence of the $18^{th}$ to $462^{nd}$ positions of SEQ ID NO: 62, the amino acid sequence of SEQ ID NO: 64, the amino acid sequence of the $18^{th}$ to 460 positions of SEQ ID NO: 64, the amino acid sequence of SEQ ID NO: 66, or the amino acid sequence of the $18^{th}$ to $460^{th}$ positions of SEQ ID NO: 66; and a light chain having the amino acid sequence of SEQ ID NO: 68, the amino acid sequence of the $21^{st}$ to $240^{th}$ positions of SEQ ID NO: 68, the amino acid sequence of SEQ ID NO: 70, or the amino acid sequence of the $21^{st}$ to $240^{th}$ positions of SEQ ID NO: 70.

4. The method of claim 1, wherein the anti-Ang-2 antibody or the antigen-binding fragment thereof comprises:

a heavy chain variable region comprising the amino acid sequence of SEQ ID NO: 162, and a light chain variable region comprising the amino acid sequence of SEQ ID NO: 170;

a heavy chain variable region comprising the amino acid sequence of SEQ ID NO: 163, and a light chain variable region comprising the amino acid sequence of SEQ ID NO: 171;

a heavy chain variable region comprising the amino acid sequence of SEQ ID NO: 164, and a light chain variable region comprising the amino acid sequence of SEQ ID NO: 172;

a heavy chain variable region comprising the amino acid sequence of SEQ ID NO: 165, and a light chain variable region comprising the amino acid sequence of SEQ ID NO: 173;

a heavy chain variable region comprising the amino acid sequence of SEQ ID NO: 166, and a light chain variable region comprising the amino acid sequence of SEQ ID NO: 174;

a heavy chain variable region comprising the amino acid sequence of SEQ ID NO: 167, and a light chain variable region comprising the amino acid sequence of SEQ ID NO: 175;

a heavy chain variable region comprising the amino acid sequence of SEQ ID NO: 168, and a light chain variable region comprising the amino acid sequence of SEQ ID NO: 176; or a heavy chain variable region comprising the amino acid sequence of SEQ ID NO: 169, and a light chain variable region comprising the amino acid sequence of SEQ ID NO: 177.

5. The method of claim 1, wherein the subject is afflicted with an angiogenesis-related disease selected from the group consisting of cancer, cancer metastasis, retinopathy of prematurity, macular degeneration, diabetic retinopathy, neovascular glaucoma, psoriasis, asthma, rheumatoid arthritis, pneumonia, chronic inflammation, infection, hypertension, arteriosclerosis, a kidney-related disorder, and sepsis, and the administration of the anti-c-Met antibody or an antigen-binding fragment thereof and the anti-Ang-2 antibody or an antigen-binding fragment thereof treats or prevents the disease.

6. The method of claim 5, wherein the angiogenesis-related disease is cancer.

* * * * *